US012054737B2

(12) United States Patent
Wunderlich et al.

(10) Patent No.: US 12,054,737 B2
(45) Date of Patent: *Aug. 6, 2024

(54) POTENT AND SHORT PROMOTER FOR EXPRESSION OF HETEROLOGOUS GENES

(71) Applicant: Janssen Vaccines & Prevention B.V., Leiden (NL)

(72) Inventors: Kerstin Wunderlich, Kassel (DE); Taco Gilles Uil, Amsterdam (NL); Jort Vellinga, Voorschoten (NL); Barbara Petronella Sanders, Amsterdam (NL); Remko Van Der Vlugt, Zoetermeer (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 349 days.

This patent is subject to a terminal disclaimer.

(21) Appl. No.: 17/302,598

(22) Filed: May 7, 2021

(65) Prior Publication Data

US 2021/0261984 A1 Aug. 26, 2021

Related U.S. Application Data

(62) Division of application No. 15/891,986, filed on Feb. 8, 2018, now Pat. No. 11,034,978.

(30) Foreign Application Priority Data

Feb. 9, 2017 (EP) .................................... 17155338
Mar. 28, 2017 (EP) .................................... 17163245

(51) Int. Cl.
*C12N 15/85* (2006.01)
*C07H 21/04* (2006.01)
*C07K 14/005* (2006.01)
*C12N 15/86* (2006.01)
*C12N 15/861* (2006.01)

(52) U.S. Cl.
CPC .......... *C12N 15/861* (2013.01); *C07K 14/005* (2013.01); *C12N 15/86* (2013.01); *C12N 2710/10343* (2013.01); *C12N 2710/16122* (2013.01); *C12N 2830/002* (2013.01); *C12N 2830/006* (2013.01); *C12N 2830/60* (2013.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil et al. |
| 5,122,458 | A | 6/1992 | Post et al. |
| 5,559,099 | A | 9/1996 | Wickham et al. |
| 5,837,511 | A | 11/1998 | Falck-Pedersen et al. |
| 5,837,520 | A | 11/1998 | Shabram et al. |
| 5,846,782 | A | 12/1998 | Wickham et al. |
| 5,851,806 | A | 12/1998 | Kovesdi et al. |
| 5,891,690 | A | 4/1999 | Massie |
| 5,965,541 | A | 10/1999 | Wickham et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 6,020,191 | A | 2/2000 | Scaria et al. |
| 6,040,174 | A | 3/2000 | Imler et al. |
| 6,083,716 | A | 7/2000 | Wilson et al. |
| 6,113,913 | A | 9/2000 | Brough et al. |
| 6,225,289 | B1 | 5/2001 | Kovesdi et al. |
| 6,261,823 | B1 | 7/2001 | Tang et al. |
| 6,485,958 | B2 | 11/2002 | Blanche et al. |
| 7,326,555 | B2 | 2/2008 | Konz, Jr. et al. |
| 7,407,801 | B2 | 8/2008 | Ostedgaard et al. |
| 7,501,129 | B2 | 3/2009 | Williams et al. |
| 8,932,607 | B2 | 1/2015 | Custers et al. |
| 2009/0181424 | A1 | 7/2009 | Albericio et al. |
| 2012/0190106 | A1 | 7/2012 | Yao |

FOREIGN PATENT DOCUMENTS

| | | | |
|---|---|---|---|
| EP | 853660 | B1 | 1/2003 |
| EP | 1230354 | B1 | 1/2004 |
| EP | 1601776 | B1 | 7/2008 |
| WO | 1999000510 | A1 | 1/1999 |
| WO | 2003/049763 | A1 | 6/2003 |
| WO | 03/061708 | A1 | 7/2003 |
| WO | 03/078592 | A2 | 9/2003 |
| WO | 2003/104467 | A1 | 12/2003 |
| WO | 2004/001032 | A2 | 12/2003 |
| WO | 2004004762 | A1 | 1/2004 |
| WO | 2004020971 | A2 | 3/2004 |
| WO | 2004037294 | A2 | 5/2004 |
| WO | 2004055187 | A1 | 7/2004 |

(Continued)

OTHER PUBLICATIONS

Abbink et al., "Comparative Seroprevalence and Immunogenicity of Six Rare Serotype Recombinant Adenovirus Vaccine Vectors from Subgroups B and D." Journal of Virology, vol. 81, No. 9, pp. 4654-4663 (May 2007).
Addison et al., "Comparison of the Human Versus Murine Cytomegalovirus Immediate Early Gene Promoters for Transgene Expression by Adenoviral Vectors," Journal of General Virology, vol. 78, pp. 1653-1661 (1997).
Altschul et al., "Basic Local Alignment Search Tool," Journal of Molecular Biology, vol. 215, pp. 403-410 (1990).
Barry et al., "Nucleotide Sequence and Molecular Analysis of the Rhesus Cytomegalovirus Immediate-Early Gene and the UL121-117 Open Reading Frames," Virology, vol. 215, No. 0007, pp. 61-72 (1996).

(Continued)

*Primary Examiner* — Celine X Qian
(74) *Attorney, Agent, or Firm* — Ice Miller LLP

(57) ABSTRACT

The invention provides an AoHV-1 promoter for use with plasmid vectors, viral vectors, viruses, and cell lines comprising the AoHV-1 promoter operably linked to a transgene. The invention also provides methods of making and using recombinant plasmid vectors, viral vectors, viruses, and cell lines comprising the AoHV-1 promoter operably linked to a transgene.

15 Claims, 15 Drawing Sheets

Specification includes a Sequence Listing.

(56) References Cited

FOREIGN PATENT DOCUMENTS

| | | | |
|---|---|---|---|
| WO | 2005002620 | A1 | 1/2005 |
| WO | 2005/071093 | A2 | 8/2005 |
| WO | 2005080556 | A2 | 9/2005 |
| WO | 2006053871 | A2 | 5/2006 |
| WO | 2006108707 | A1 | 10/2006 |
| WO | 2006120034 | A1 | 11/2006 |
| WO | 2007073513 | A2 | 6/2007 |
| WO | 2007/104792 | A2 | 9/2007 |
| WO | 2007100908 | A2 | 9/2007 |
| WO | 2007/110409 | A1 | 10/2007 |
| WO | 2009026183 | A1 | 2/2009 |
| WO | 2009117134 | A2 | 9/2009 |
| WO | 2010/085984 | A1 | 8/2010 |
| WO | 2010/086189 | A2 | 8/2010 |
| WO | 2010096561 | A1 | 8/2010 |
| WO | 2011045378 | A1 | 4/2011 |
| WO | 2011045381 | A1 | 4/2011 |
| WO | 2013139911 | A1 | 9/2013 |
| WO | 2013139916 | A1 | 9/2013 |
| WO | 2016166088 | A1 | 10/2016 |

OTHER PUBLICATIONS

Belousova et al., "Circumventing Recombination Events Encountered with Production of a Clinical-Grade Adenoviral Vector with a Double-Expression Cassette," Molecular Pharmacology, vol. 70, No. 5, pp. 1488-1493 (2006).

Chan et al., "Synergistic Interactions Between Overlapping Binding Sites for the Serum Response Factor and ELK-1 Proteins Mediate Both Basal Enhancement and phorbol Ester Responsiveness of Primate Cytomegalovirus Major Immediate-Early Promoters in Monocyte and T-Lymphocyte Cell Types," Journal of Virology, vol. 70, No. 12, pp. 8590-8605 (Dec. 1996).

Chang et al., "Identificaiton of a Large Bent DNA Domain and Binding Sites for Serum Response Factor Adjacent to the NFI Repeat Cluster and Enhancer Region in the Major IE94 Promoter from Simian Cytomegalovirus," Journal of Virology, vol. 67, No. 1, pp. 516-529 (Jan. 1993).

Database EMBL, "Aotine Herpesvirus 1 Strain S34E, Complete Genome," Jun. 7, 2009, 86 pages.

Extended Search Report issued May 2, 2017 in EP Application No. 17155338.1.

Foecking et al., "Powerful and Versatile Enhancer-Promoter Unit for Mammalian Expression Vectors," Gene, vol. 45, pp. 101-105 (1986).

Gao et al., "A Cell Line for High-Yield Production of E1-Deleted Adenovirus Vectors Without the Emergence of Replication-Competent Virus," Human Gene Therapy, vol. 11, pp. 213-219 (Jan. 1, 2000).

Gibson et al., "Enzymatic Assembly of DNA Molecules Up to Several Hundred Kilobases," Nature Methods, vol. 6, No. 5, pp. 343-347 (May 2009).

Gossen et al., "Tight Control of Gene Expression in Mammalian Cells by Tetracycline-Responsive Promoters," Proc. Natl. Acad. Sci., vol. 89, pp. 5547-5551 (Jun. 1992).

Gossen et al., "Transcriptional Activation by Tetracyclines in Mammalian Cells," Science, vol. 268, pp. 1766-1769 (Jun. 23, 1995).

Hansen et al., "Complete Sequence and Genomic Analysis of Rhesus Cytomegalovirus," Journal of Virology, vol. 77, No. 12, pp. 6620-6636 (Jun. 2003).

Havenga et al., "Novel Replication-Incompetent Adenoviral B-Group Vectors: High Vector Stability and Yield in PER. C6 Cells," Journal of General Virology, vol. 87, pp. 2135-2143 (2006).

Heilbronn et al., "Viral Vectors for Gene Transfer: Current Status of Gene Therapeutics," Handbook of Experimental Pharmacology, vol. 197, pp. 143-170 (2010).

Hoganson et al., "Development of a Stable Adenoviral Vector Formulation," Bioprocessing Journal, pp. 43-48 (Mar. 2002).

Holterman et al., "Novel Replication-Incompetent Vector Derived from Adenovirus Type 11 (AD11) for Vaccination and Gene Therapy: Low Seroprevalence and Non-Cross-Reactivity with Ad5," Journal of Virology, vol. 78, No. 23, pp. 13207-13215 (Dec. 2004).

Lemckert et al., "Generation of a Novel Replication-Incompetent Adenoviral Vector Derived from Human Adenovirus Type 49: Manufacture on PER.C6 Cells, Tropism and Immunogenicity," Journal of General Virology, vol. 87, pp. 2891-2899 (2006).

Maziel et al., "The Polypeptides of Adenovirus, " Virology, vol. 36, pp. 115-125, (1968).

Mullick et al., "The Cumate Gene-Switch: A System for Regulated Expression in Mammalian Cells," BMC Biotechnology, vol. 6, No. 43, 18 pages (2006).

Ogun et al., "The Oligomerization Dornain of C4-Binding Protein (C4bp) Acts as an Adjuvant, and the Fusion Protein Comprised of the 19-Kilodallton Merozoite Surface protein 1 Fused with the Murine C4bp Domain Protects Mise against Malaria," Infection and Immunity, vol. 76, No. 8, pp. 3817-3823 (Aug. 2008).

Powel et al., "Viral Expression Cassette Elements to Enhance Transgene Target Specificity and Expression in Gene Therapy," Discovery Medicine, vol. 19, No. 102, pp. 49-57 (Jan. 2015).

Robbins et al., "Viral Vectors for Gene Therapy," Pharmacol. Ther., vol. 80, No. 1, pp. 35-47 (1998).

Rubnitz et al., "The Minimum Amount of Homology Required for Homologous Recombination in Mammalian Cells," Molecular and Cellular Biology, vol. 4., No. 11, pp. 2253-2258 (Nov. 1984).

Schlabach et al., "Synthetic Design of Strong Promoters," PNAS, vol. 107, No. 6, pp. 2538-2543, (Feb. 8, 2010).

Smale, "Core Promoters: Active Contributors to Combinatorial Gene Regulation," Genes and Development, vol. 15, pp. 2503-2508 (2001).

Vogels et al., "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).

Walther et al., "Viral Vectors for Gene Transfer," Drugs, vol. 60, No. 2, pp. 249-271 (Aug. 2000).

Zahn et al., "Ad35 and Ad36 Vaccine Vectors Induce Potent and Cross-Reactive Antibody and T-Cell Responses to Multiple Filovirus Species," PLOS One, vol. 7, No. 12, 13 pages (Dec. 2012).

Int'l Search Report issued Mar. 27, 2018 in Int'l Application No. PCT/EP2018/053201.

Written Opinion issued Mar. 27, 2018 in Int'l Application No. PCT/EP2018/053201.

Fig. 2A

```
                                  20                                40
hCMV         CATCAAGTGT ATCATATGCC AAGTACGCCC CCTATTGACG TCAATGACGG 50
chCMV short  CGCCAATTGC ATCAT----- ---------- CCTATTGTTT TT-------- 27
                    60                     80                     100
hCMV         TAAATGGCCC GCCTGGCATT ATGCCCAGTA CATGACCTTA TGGGACTTTC 100
chCMV short  ---------- ---------- ---------- -------CTA TGGGAATTTC 40
                                 120                   140
hCMV         CTACTTGGCA GTACATCTAC GTATTAGTCA TCGCTATTAC CATGGTGATG 150
chCMV short  CCTATTGGCA GTACATCAAC GTATTAGTAA TGGGGATTTC CA--ATGAC- 87
                   160                    180                    200
hCMV         CGGTTTTGGC AGTACATCAA TGGGCGTGGA TAGCG-GTTT GACTCACGGG 199
chCMV short  ---------T AATACAACGG GCAGTACGCC CAGTACGTAT GACTAATGGG 128
                                 220                   240
hCMV         GATTTCCAAG TCTCCACCCC ATTGACGTCA ATGGGAGTTT GTTTTGGCAC 249
chCMV short  ACTTTCCATA ATCCCGCCCC ATTGACGTCA ATGGGCATCC GTTCTGGCAC 178
                   260                    280                    300
hCMV         CAAAATCAAC GGGACTTTCC AAAATGTCGT AACAACTCCG CCCCATTGAC 299
chCMV short  CAAAATGAAT GGGAATTTCC AATATGAGTC ATAAACCCCG CCCCATTGAC 228
                                 320                   340
hCMV         GCA------- ----AATGGG CGGTAGGCGT GTACGGTGGG AGGTCTATAT 338
chCMV short  GCACATTACA CGTCAATGGG CGGTAGGCGT GCCCTATGGG CGGTCTATAT 278
                   360                    380                    400
hCMV         AAGCAGAGCT CGTTTAGTGA ACCGTCAGAT CGCCTGGAGA CGCCATCCAC 388
chCMV short  AAGCAGAGCC CGTTTAGTGA ACCGTCACTT CGCTTGGAGC CACCGTCCAC 328
                                 420                   440
hCMV         GCTGTTTTGA CCTCCATAGA AGACACCGGG ACCGATCCAG CCTCCGCGGC 438
chCMV short  GCTGTTTGGA GCTCCATAGA AGGAACCGGG ACCCAGCCAG CCTCCGTAGC 378
                   460
hCMV         CGGGAACGGT GCATTGGA-- 456
chCMV short  CGGGAACGGT GCATTGGAAC 398
```

```
                                     20                    40
hCMV          AAATCAATAT TGGCTATTGG CCATTGCATA CGTTGTATCC ATATCATAAT 50
AoHV-1 short  AAATCAATGA C-----TTGG CAA------- ---------- --------GC 20
                        60                    80                   100
hCMV          ATGTACATTT ATATTGGCTC ATGTCCAACA TTACCGCCAT GTTGACATTG 100
AoHV-1 short  ATATACATCC GTCCTGGC-- ---------- ---------- ---------- 38
                                    120                   140
hCMV          ATTATTGACT AGTTATTAAT AGTAATCAAT TACGGGGTCA TTAGTTCATA 150
AoHV-1 short  -------ACC AG-----AAT AGGGGTTAAA TGGGG----- ---------- 61
                       160                   180                   200
hCMV          GCCCATATAT GGAGTTCCGC GTTACATAAC TTACGGTAAA TGGCCCGCCT 200
AoHV-1 short  ---------- ---------- --------AC TTTCCATAAG CCCACCGCCT 83
                                    220                   240
hCMV          GGCTGACCGC CCAACGACCC CCGCCCATTG ACGTCAATAA TGACGTATGT 250
AoHV-1 short  CATTTGGCAC CAAAAAG--- --GGGGATTT CTATTATTAG TCA---ATGT 125
                       260                   280                   300
hCMV          TCCCATAGTA ACGCCAATAG GGACTTTCCA TTGACGTCAA TGGGTGGAGT 300
AoHV-1 short  CCTTG----- --GCCAATAG -------CCA GTGACGTCAA TGGGAACGG- 160
                                    320                   340
hCMV          ATTTACGGTA AACTGCCCAC TTGGCAGTAC ATCAAGTGTA TCATATGCCA 350
AoHV-1 short  ------GGCC AGTTCCCCTT T--------- ---------- ---------- 175
                       360                   380                   400
hCMV          AGTACGCCCC CTATTGACGT CAATGACGGT AAATGGCCCG CCTGGCATTA 400
AoHV-1 short  ------CCCA CCATTACCGG CAATGGTGG- ---------- ---------- 198
                                    420                   440
hCMV          TGCCCAGTAC ATGACCTTAT GGGACTTTCC TACTTGGCAG TACATCTACG 450
AoHV-1 short  ---------- ---------- ---------- ------GTGG GGAAATTCCA 212
                       460                   480                   500
hCMV          TATTAGTCAT CGCTATTACC ATGGTGATGC GGTTTTGGCA GTACATCAAT 500
AoHV-1 short  TATTAGTCAA TGTTCTTG-- ---------- ---------- --GCACCAA- 237
                                    520                   540
hCMV          GGGCGTGGAT AGCGGTTTGA CTCACGGGGA TTTCCAAGTC TCCACCCCAT 550
AoHV-1 short  ---------- ---------A ACCGCGGGGA CTTTC----- -------CAT 256
                       560                   580                   600
hCMV          TGACGTCAAT GGGAGTTTGT TTTGGCACCA AAATCAACGG GACTTTCCAA 600
AoHV-1 short  TGACGTCAGT GGAAAGGGGC GTAACGGGGA GTGACCATGG GCGTTCCCGG 306
                                    620                   640
hCMV          AATGTCGTAA CAACTCCGCC CCATTGACGC AAATGGGCGG TAGGCGTGT- 649
AoHV-1 short  G--------- -----CGGAG TTATGGGCGT TACTGGGCGG TTCGTGGGCG 342
                       660                   680                   700
hCMV          -ACGGTGGGA GGTC------ TATATAAGCA GAGCTCGTTT AGTGAACCGT 692
AoHV-1 short  GACCATGGGC TGTCCTAGGG TATATAAGCA GAGCCCGGTT AGCAGACCGC 392
                                    720                   740
hCMV          CAGATCGCCT GGAGACGCCA TCCACGCTGT TTTGACCTCC ATAGAAGACA 742
AoHV-1 short  CATTCGGCTT CAAGACAGCG TGAGGGAC-C CACGTTCTCC GGACCAGCCA 441
                       760                   780
hCMV          CCGGGACCGA TCCAGCCTCC GCGGCCGGGA ACGGTGCATT GGA 785
AoHV-1 short  CCGGGACCGA GCGGCCTAGC CTAGCCGGGG ACCCTTCACT GG- 483
```

Fig. 2B

| | E1 PCR | E4 PCR1 | E4 PCR2 |
|---|---|---|---|
| P1 | 1353 bp | NA | NA |
| P2 | NA | 508 bp | 205 bp |
| V1 | 1959 bp | 2912 bp | 2609 bp |
| V2 | 1905 bp | 2912 bp | 2609 bp |

POTENT AND SHORT PROMOTER FOR EXPRESSION OF HETEROLOGOUS GENES

CROSS REFERENCE TO RELATED APPLICATIONS

This application is a divisional of U.S. patent application Ser. No. 15/891,986, filed Feb. 8, 2018, which claims priority to EP Application No. 17155338.1, filed on Feb. 9, 2017, and EP Application No. 17163245.8, filed on Mar. 28, 2017. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "004852_82US2_Sequence_Listing" and a creation date of May 6, 2021, and having a size of 51 kB. The sequence listing submitted via EFS-Web is part of the specification and is herein incorporated by reference in its entirety.

TECHNICAL FIELD

The invention relates to the fields of biological research, medicine, and other applications related to heterologous gene expression. More in particular, the invention relates to a potent and short promoter for the expression of a heterologous gene in expression cassettes of plasmids, viral vectors and cell lines which can be used alone or in combination with commonly used promoters such as the hCMV promoter.

BACKGROUND OF THE INVENTION

Recombinant expression vectors are used extensively in a variety of molecular biology applications for the expression of heterologous proteins, including, for example, mammalian gene expression systems for biological research, to produce cell lines for production of viral vectors, and as viral vectors for gene therapy and vaccination. For gene therapy and vaccination applications, vectors, including viral vectors, are used as carriers for a gene or genes of interest to be introduced into cells. For example, viral vectors can be used to express a gene or part thereof encoding a desired antigen to elicit an immune response.

The cis-acting elements that are part of expression vectors can have a great impact on the successful application of plasmids and viral vectors. Promoters are the major cis-acting elements that are placed in the expression cassettes of expression vectors and dictate the overall strength of expression. The promoter initiates the transcription and is therefore an important point of control for the expression of the cloned gene of interest. Promoter sequences commonly used in expression vectors are derived from viruses or eukaryotic gene regulatory sequences.

Some of the commonly used enhancer and promoter sequences in expression vectors and viral vectors are, for example, hCMV, CAG, SV40, mCMV, EF-1α and hPGK promoters. Due to its high potency and moderate size of ca. 0.8 kB, the hCMV promoter is one of the most commonly used of these promoters. The hPGK promoter is characterized by a small size (ca. 0.4 kB), but it is less potent than the hCMV promoter. On the other hand, the CAG promoter consisting of a cytomegalovirus early enhancer element, promoter, first exon and intron of chicken beta-actin gene, and splice acceptor of the rabbit beta-globin gene, can direct very potent gene expression that is comparable to the hCMV promoter, but its large size makes it less suitable in viral vectors where space constraints can be a significant concern, e.g., in adenoviral vectors (AdV), adeno-associated viral vectors (AAV) or lentiviral vectors (LVs).

In certain cases, it's desirable to express at least two antigens from one vector. In situations where two expression cassettes are placed in a vector in order to express two different genes, the size constraints for the expression cassettes in general and the promoter sequences in particular are especially important. In addition to size constraints, when placing two expression cassettes in a vector it is a disadvantage to use identical or even very similar promoter sequences because it can lead to genetic instability of the vector during production. Thus, it is desirable to use relatively small and relatively potent different heterologous promoter sequences that have little to no sequence identity with each other when two expression cassettes are placed in a vector in order to express two different genes.

When making cell lines for production of viral vectors it is also desirable to have a potent promoter with a sequence different from other promoters commonly used in the expression cassettes of the viral vectors, such as the commonly used hCMV promoter. Significant stretches of sequence identity between the genome of the cell line and the vector produced therein can lead to homologous recombination and therefore genetic instability or heterogeneity of the produced vector batches (e.g. Lochmuller et al, 1994), and therefore are preferably avoided (e.g. Fallaux et al, 1998; Murakami et al, 2002). Also for such applications, it would be desirable to use a potent promoter with little or no sequence identity with the commonly used hCMV promoter.

Thus, there remains a need to identify potent promoters, which preferably would be of short size and that would have little to no sequence identity with the hCMV promoter, for use in for instance plasmids, viral vectors and cell lines.

SUMMARY OF THE INVENTION

The present invention provides recombinant nucleic acid molecules comprising the major immediate early promoter region of Aotine herpesvirus-1 (AoHV-1 promoter) and vectors, including, for example, plasmid vectors, viral vectors, recombinant viruses, and recombinant cell lines comprising the AoHV-1 promoter operably linked to a transgene. The present invention also provides recombinant nucleic acid molecules comprising the AoHV-1 promoter operably linked to regulatory sequences that can be used to modulate transcription from the AoHV-1 promoter.

The general and preferred embodiments are defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

In one embodiment, the present invention provides an AoHV-1 promoter, wherein the AoHV-1 promoter is operably linked to a transgene for expression of the transgene with plasmid vectors, viral vectors or recombinant viruses, or in the genome of host cells comprising the AoHV-1 promoter.

In certain embodiments, the invention provides a plasmid vector comprising an AoHV-1 promoter, which plasmid vector comprises less than 1 kb of AoHV-1 DNA.

In certain embodiments, the invention provides an expression cassette, comprising an AoHV-1 promoter operably linked to a transgene, which transgene is heterologous to the AoHV-1 promoter, e.g., wherein the transgene is not operably linked to the AoHV-1 promoter in nature and/or the transgene does not originate from AoHV-1. The expression cassette may for instance be integrated into a plasmid, a vector, a viral genome, a cell line, etc. The invention also provides a method of making such an expression cassette, comprising constructing the expression cassette by recombinant means or by nucleic acid synthesis. The invention also provides a method for expressing a transgene, comprising expressing the transgene from the expression cassette of the invention, e.g. in a recombinant cell line.

In certain embodiments, the present invention provides recombinant cell lines comprising the AoHV-1 promoter, wherein the AoHV-1 promoter is operably linked to a transgene. In certain embodiments, the AoHV-1 promoter operably linked to a transgene may be present in the cell line embodied in e.g. plasmid vectors, viral vectors, or recombinant viruses for expression of the transgene therefrom. In certain embodiments, the AoHV-1 promoter operably linked to a transgene is integrated into the genome of the recombinant cell line, to express the transgene therefrom. In certain embodiments, the transgene is integrated into the genome of the cell line and encodes a tetracycline repressor (TetR) protein. In certain embodiments thereof, said cell line is a PER.C6 cell line.

In another embodiment, the present invention also provides a method for expressing a transgene in a cell, the method comprising providing a cell with a recombinant vector comprising the AoHV-1 promoter operably linked to a transgene.

In certain embodiments the invention also provides a method for producing a protein of interest, wherein the AoHV-1 promoter is operably linked to a transgene encoding the protein of interest, the method comprising providing a cell comprising an AoHV-1 protein operably linked to a nucleic acid sequence encoding the protein of interest, and expressing the protein of interest from the cell. In certain embodiments the method further comprises harvesting the protein of interest, e.g. from the cells or from culture medium or from the cells and culture medium. In certain embodiments, the method further comprises purifying the protein of interest. Preferably, the protein of interest is a protein that is not encoded by Aotine herpesvirus-1 in nature, i.e. it is a heterologous protein.

In certain embodiments, the present invention provides the AoHV-1 promoter operably linked to regulatory sequences that can be used to modulate transcription from the AoHV-1 promoter. In certain embodiments thereof, it can for instance be repressed by binding of a repressor to a repressor binding sequence that has been operably linked to the AoHV-1 promoter. In certain embodiments, the AoHV-1 promoter can be induced by removing a repressor or by providing an inducing signal or inducing agent.

In certain embodiments, the present invention provides the AoHV-1 promoter operably linked to one or more tetracycline operator sequences (tetO sites), such that expression can be reversibly controlled.

In another embodiment, the present invention also provides a method of producing a recombinant virus comprising the AoHV-1 promoter, the method comprising: preparing a construct comprising the AoHV-1 promoter operably linked to a transgene, and incorporating said construct into the genome of the recombinant virus.

In certain embodiments of the present invention, the AoHV-1 promoter is operably linked to a transgene encoding a protein of interest, wherein the protein of interest is a therapeutic protein or an antigen.

In certain embodiments, the viruses and viral vectors comprising the AoHV-1 promoter operably linked to a transgene are recombinant adenoviruses (rAd) and rAd vectors.

In certain embodiments, the invention relates to rAd and rAd vectors comprising the AoHV-1 promoter operably linked to a transgene, and to methods of making and/or using the rAd and rAd vectors, wherein the rAd and rAd vectors comprise a AoHV-1 promoter operably linked to a transgene.

In certain embodiments, a recombinant adenovirus of the invention has a deletion in the E1 region, and in certain embodiments comprises the AoHV-1 promoter operably linked to a transgene in this E1 region. Alternatively, other regions of the recombinant adenovirus could also be used. For example, the expression cassette comprising AoHV-1 promoter operably linked to a transgene could also be placed in the E3 region, or at the right end of the genome, between the E4 region and the right ITR of the recombinant adenovirus.

In certain embodiments, a rAd vector according to the invention is deficient in at least one essential gene function of the E1 region, e.g. the Ela region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

In another embodiment, the present invention also provides a recombinant DNA molecule comprising the genome of a recombinant adenovirus comprising the AoHV-1 promoter operably linked to a transgene.

BRIEF DESCRIPTION OF THE DRAWINGS

FIGS. 2A and 2B: Sequence alignments between hCMV and chCMV short or AoHV-1 short performed with CLC workbench. Grey shading indicates the nucleotide differences between the aligned sequences. Alignments were performed with the complete promoter sequence. However, only the region in which the sequences align is shown in the Figure, since these regions are relevant for potential homologous recombination events. Dashes indicate regions of no alignment (gaps). (FIG. 2A) Alignment region of hCMV (SEQ ID NO:35) with chCMV short (SEQ ID NO:36). (FIG. 2B) Alignment region of hCMV (SEQ ID NO:37) with AoHV-1 short (SEQ ID NO:30).

(FIG. 4A) Comparison of the potency of the promoters hCMV, hPGK and AoHV-1 short to induce eGFP expression in transient plasmid transfections. Shown are pictures of eGFP expression taken by an Evos fluorescent microscope. (FIG. 4B) Design and testing of a regulated version of AoHV-1 short. Transient expression of eGFP by AoHV.2xtetO or a standard hCMV promoter (pCDNA) in PER.C6-hCMV.TetR cells. (FIG. 4C) Regulated expression of a GOI by AoHV.2xtetO in a stable cell line. Shown is expression of the GOI in a Western Blot assay. Labelling of the lanes: Lane 1: clone 11, Lane 2: clone 11+Doxycyclin, Lane 3: Clone 73, Lane 4: Clone 73+Doxycyclin, Lane 5: positive expression control, cells transiently transfected with plasmid expressing the GOI under control of AoHV-1 promoter, Lane 6: negative control (untransfected PER.C6 cells).

(FIG. 5A) Schematic representation of Ad26.CMV_GLuc.AoHV1_RFL and Ad26.CMVtetO_GLuc.AoHV1_RFL vector genomes. The open arrows indicate the two transgene cassette insertions: a CMV or CMVtetO promoter-driven Gluc expression cassette inserted at the location of the E1 region deletion, and an AoHV-1 promoter-driven RFL expression cassette inserted in between the E4 region and the RITR. Black arrows represent the promoters driving the transgene cassettes. Grey arrows represent coding sequences. GLuc, *Gaussia* luciferase. RFL, red firefly luciferase. LITR and RITR, left and right inverted terminal repeats. CMV, human cytomegalovirus major immediate early promoter (hCMV MIEp). CMVtetO, hCMV MIEp equipped with two tetracycline operator (TetO) sequences (for TetR-repressible expression). AoHV-1 P, AoHV-1 short promoter. SV40 pA, SV40 virus-derived polyadenylation signal. BGHpA, bovine growth hormone gene-derived polyadenylation signal. E4, E4 region of Ad26. (FIG. 5B) Analysis of transgene (TG) cassette integrity for Ad26.CMV_GLuc.AoHV1_RFL and Ad26.CMVtetO_GLuc.AoHV1_RFL purified batches by identity PCR. PCRs were performed to amplify the TG cassette inserted in E1 ("E1 PCR"), and the TG cassette located in between E4 and the RITR ("E4 PCR1" and "E4 PCR2"). The expected PCR product sizes for the different PCRs are indicated in the figure inset. L, 1 Kb Plus DNA Ladder (Invitrogen), P1=pAdApt26 (Abbink et al., 2007), with an "empty" expression cassette (i.e. consisting of the hCMV promoter and the SV40 polyadenylation signal but without a TG coding sequence). P2, pWE.Ad26.dE3.5orf6 (Abbink et al., 2007), no transgene cassette insertion in between the E4 region and the RITR. W, no DNA template control. V1, Ad26.CMVtetO_GLuc.AoHV1_RFL viral DNA. V2, Ad26.CMV_GLuc.AoHV1_RFL viral DNA. (FIGS. 5C and 5D) Analysis of transgene expression by Ad26.CMV_GLuc.AoHV1_RFL and Ad26.CMVtetO_GLuc.AoHV1_RFL purified batches. A549 cells, seeded in 96-well plates, were infected in triplicates at the indicated viral particle to cell ratio (VP/cell), and GLuc and RFL activities were detected in samples harvested 2 days post infection. RLU, relative light units. Ad26.CMV (empty), a matching control Ad26 viral vector that does not carry GLuc or RFL coding sequences. *, one outlier value of 187 RLU that was seen for the infection with Ad26.CMVtetO_Gluc.AoHV1_RFL at 10 VP/cell was removed (the other two values for this triplicate infection were 14 and 26 RLU).

(FIG. 6A) Plasmid map of pC_AoHV_TetR. The grey arrows indicate coding sequences for the tetracycline repressor (TetR) protein, neomycin phosphotransferase II, and beta-lactamase; black arrows indicate other genetic elements. The open arrow indicates the synthetic sequence that was inserted into pcDNA2004Neo(−) to construct pC_AoHV_TetR. AoHV-1 P, AoHV-1 short promoter. TetR, codon-optimized tetracycline repressor coding sequence. BGH pA, bovine growth hormone gene-derived polyadenylation signal. SV40 P, SV40 virus-derived promoter. pUC ori, pUC origin of replication. bla P, promoter for driving expression of beta-lactamase. (FIG. 6B) Stability of TetR expression by PER.C6/TetR cell clones upon extended passaging by flow cytometry intracellular staining at generations 20, 40, and 60. TetR-positive fractions observed for each clone (grown with and without selection), at each timepoint are shown. PER.C6, control PER.C6 cell line without TetR construct, grown only without antibiotic selection. (FIG. 6C) TetR functionality assay after extended passaging (60 population doublings). PER.C6/TetR cell clones were infected with Ad26.CMV_GLuc.AoHV1_RFL and Ad26.CMVtetO_GLuc.AoHV1_RFL, after which GLuc and RFL activities were determined. Per infection replicate, the CMV or CMVtetO promoter-driven GLuc activities were normalized by the AoHV-1 promoter-driven RFL activities seen for the same sample. The resulting normalized Gluc values are expressed in this figure relative to those found for TetR-negative control cell line (PER.C6). +, cells were grown with antibiotic selection. −, cells were grown without antibiotic selection. Ctrl (+), a previously established TetR-positive control cell line derived from PER.C6 by stable transfection with pCDNA6/TR (Thermo Fisher Scientific, Catalog number: V102520), a plasmid comprising a TetR sequence under control of a human CMV promoter.

(FIG. 7A) Design of truncated and elongated versions of the AoHV-1 promoter. Depicted is a representation of a 2774-bp stretch of the aotine herpesvirus 1 genome corresponding, from left to right, to nucleotide numbers 157077 to 154304 of GenBank accession NC_016447. The labelled bars indicate different AoHV-1 promoter variants that were designed and tested herein. Sequences v00 and v06 represent the AoHV-1 short promoter, respectively with and without its native AvrII site. D and A, predicted splice donor and acceptor sites, respectively. TATA, putative TATA box. Inr, putative initiator sequence (containing the predicted transcription start site). (FIG. 7B) Results of potency testing of different versions of AoHV-1 promoter in transiently transfected PER.C6 cells. Mean results of two experiments are shown relative to v00 AoHV-1 short promoter.

DETAILED DESCRIPTION OF THE INVENTION

Figure 1:
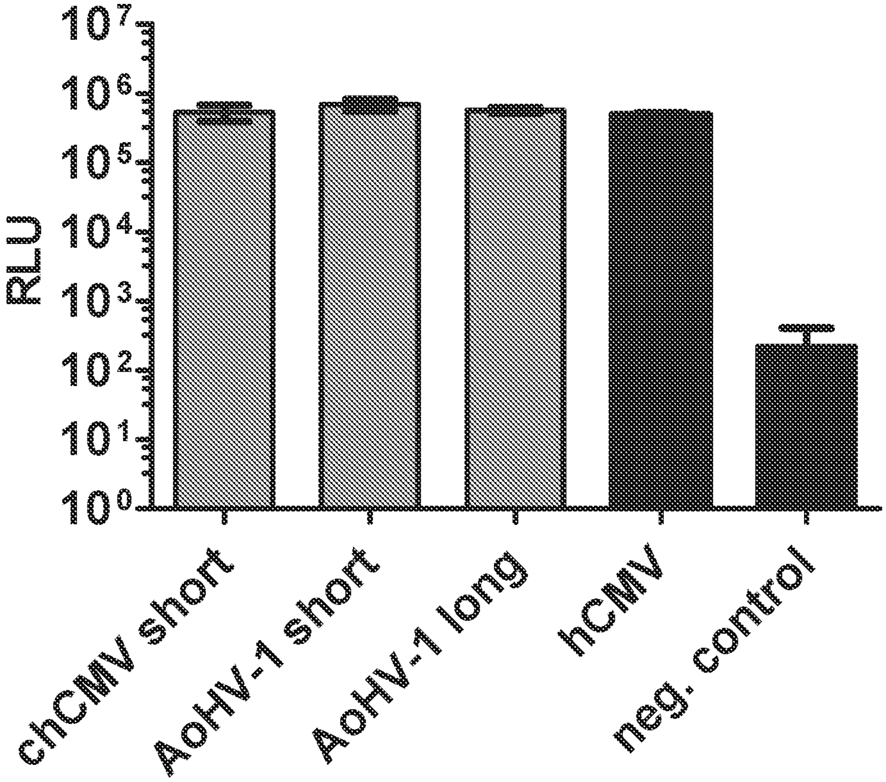
FIG. 1: Expression of Luciferase from different promoter constructs evaluated with transient transfections in HEK293 cells. Luciferase expression was measured as relative light units (RLU) and corrected for transfection efficiency by measuring SEAP levels. Results are shown for the indicated promoters, compared to the positive control of Luciferase under control of a hCMV promoter and a negative control of untransfected cells.

Described herein are experimental results related to the identification, design, and testing of a new promoter derived from the immediate early enhancer/promoter region of Aotine herpesvirus-1 (AoHV-1 promoter). The results show that the AoHV-1 promoter provides potent expression of a transgene to which it is operably linked, based on transient transfection with plasmid vectors in different cell lines and viral infections with viruses comprising the AoHV-1 promoter operably linked to a transgene. The AoHV-1 promoter is also a relatively short promoter so it is suitable for use in many applications where size constraints are a concern. Thus, the AoHV-1 promoter of the present invention is suitable for use in applications where potent expression is a priority and/or where the small size of the AoHV-1 promoter is useful, e.g. to leave more space for transgenes in the limited size of the vector or viral genome, as compared to other, longer promoters. Furthermore, due to low sequence homology with other commonly used promoters like hCMV, the AoHV-1 promoter is also useful in applications where there is a concern about sequence identity between the two promoters being used together at the same time, e.g., when expressing two different transgenes from the same viral vector or when generating viruses with producer cell lines that also contain hCMV promoter sequences. The AoHV-1 promoter is also suitable for use with regulatory sequences that can be used to modulate transcription from the AoHV-1 promoter.

The present invention therefore relates to recombinant nucleic acid molecules comprising an AoHV-1 promoter operably linked to a transgene. In certain embodiments, the invention relates to using vectors and viruses comprising the AoHV-1 promoter operably linked to a transgene for expressing the transgene in a cell. In particular non-limiting embodiments, the vectors of the present invention may comprise a plasmid, a cosmid, a phagemid, a bacteriophage, a bacterial artificial chromosome, a yeast artificial chromosome, a human artificial chromosome, a retrovirus vector, a lentivirus vector, an adenovirus vector, an adeno-associated virus vector, an alphavirus vector, a herpes virus vector, an Epstein-Barr virus vector, a vaccinia virus vector, or combinations or chimerics thereof. Those of ordinary skill in the art will recognize that the AoHV-1 promoter of the present invention also will be useful in other vectors employed in the fields of gene expression and gene transfer, especially those in which potent expression is important and the overall size of the expression cassette is a relevant factor.

The present invention also relates to using vectors for enabling host cells to produce heterologous proteins, or other expression products of interest. For example, plasmid vectors comprising the AoHV-1 promoter operably linked to a transgene could be used for expressing a heterologous protein in the cell. Such plasmid vectors could be DNA sequences containing, for example, (1) the AoHV-1 promoter; (2) a Kozak consensus sequence for the transgene for initiation of translation; (3) a coding region for the transgene, e.g., a sequence of nucleotides which codes for a desired polypeptide; (4) a termination sequence for the transgene which permits translation to be terminated when the entire code for the transgene has been read; polyadenylation signals, and/or or intervening sequences and other elements known to those of ordinary skill in the art to express transgenes from certain vectors; and (6) optionally, if the vector is not directly inserted into the genome, an origin of replication which permits the entire vector to be reproduced once it is within the cell. The vector can be introduced into the host cell, for example by transfection, electroporation, or infection, and the host cells can be cultured to express the transgene.

Plasmid vectors of the present invention in certain embodiments also include one or more multiple cloning sites (MCS), also called polylinkers, which are short segments of DNA containing several restriction sites. These restriction sites within the MCS are typically unique, occurring only once within a given plasmid. MCSs are commonly used during procedures involving molecular cloning or subcloning and are extremely useful in biotechnology, bioengineering, and molecular genetics because they allow for insertion of a piece of DNA or several pieces of DNA into the region of the MCS, e.g., to insert an expression cassette, comprising an AoHV-1 promoter operably linked to a transgene encoding a protein of interest for expression in a cell.

The present invention also provides cells transformed by the vectors described herein and recombinant cell lines comprising the AoHV-1 promoter, wherein the AoHV-1 promoter is operably linked to a transgene. In this context, transformation refers to any process by which heterologous nucleic acid material is introduced into and expressed within a cell. Thus, transformation as used herein includes "transient" and "stable" transfection procedures, including but not limited to those mediated by electroporation, cationic lipid/DNA complexes, protein/DNA complexes, calcium phosphate-mediated pinocytosis, virus vectors, etc., where a nucleic acid introduced into the host cell exists extrachromosomally or wherein the transfected nucleic acids have been integrated into the genome of the host cell. The transfection procedures can also include a second nucleic acid encoding a selectable marker (e.g. resistance to an antibiotic), which enables the positive selection of cells such that the transfected nucleic acid containing the AoHV-1 promoter is maintained. Thus the AoHV-1 promoter operably linked to a transgene may be present in the cell line embodied in e.g. plasmid vectors, viral vectors, and recombinant viruses for expression of the transgene therefrom. In certain embodiments, the AoHV-1 promoter operably linked to a transgene can be integrated into the genome of the recombinant cell line to express the transgene therefrom.

The present invention also provides a method for expressing a transgene in a cell, the transgene comprising, for example, a transgene encoding a protein of interest or a transgene comprising a non-coding sequence (e.g., regulatory RNA such as a microRNA, short interfering RNA (siRNA), or antisense RNA, etc.), the method comprising providing a cell with a vector comprising the AoHV-1 promoter operably linked to a transgene. In particular, in certain embodiments the invention provides a method for producing an expression product of interest in a cell, wherein the AoHV-1 promoter is operably linked to a transgene encoding the expression product of interest, the method comprising providing a cell comprising an AoHV-1 promoter operably linked to a nucleic acid sequence encoding the expression product of interest, and expressing the expression product of interest in the cell. In certain embodiments the expression product is a protein. In certain embodiments, the expression product is tetracycline repressor (TetR) protein. The method can further comprise harvesting the expression product, e.g. protein, of interest, e.g. from the cells or from the culture medium or from the cells and the culture medium. The method may also comprise purifying the protein for various purposes, including for example, diagnostic, therapeutic or prophylactic purposes, research, etc. Further the purified protein of interest can optionally be formulated into a pharmaceutical composition. Therapeutic proteins may include, for example, anticoagulants, blood clotting factors, growth factors, hormones, antibodies, Fc fusion proteins, bone morphogenetic proteins, engineered protein scaffolds, enzymes, and cytokines, e.g., chemokines, interferons, interleukins, lymphokines, and tumour necrosis factors, etc.

The invention also provides a method for producing a virus, comprising propagating the virus in a cell that expresses a gene that has a function in propagating said virus, wherein said gene is under control of an AoHV-1 promoter and wherein said gene encodes a nucleic acid (e.g. regulatory RNA) or protein, e.g. a protein that complements a deficiency in the viral replication cycle or other function of virus (e.g. infection). The virus can be a wild type virus, but preferably is a recombinant virus, e.g. with a deficiency that renders it replication deficient or infection deficient. Furthermore, said gene can be expressed from an extrachromosomal element or preferably from the genome of the cell (which cell then may be from a stable cell line) and the cell can be cultured in culture medium such that virus can be harvested and optionally purified and then used to infect other cells, or to formulate in pharmaceutical composition, etc.

A "cell" or a "host cell" according to the invention can be any cell wherein the AoHV-1 promoter can be active. In certain embodiments the cell is isolated from its normal tissue, and for instance can be cultured in a culture medium (in vitro). In certain embodiments, a cell or host cell according to the invention is an immortalized cell, e.g. from a cell line. In certain embodiments, a cell or host cell according to the invention is a mammalian or an avian cell, preferably a mammalian cell. Some non-limiting examples of cells or host cells according to the invention are rodent cells, human cells, simian cells, dog cells, chicken cells, etc. Some non-limiting examples of cells or host cells according to the invention are a Vero cell, an MDCK cell, a HEK293 cell, a PER.C6 cell, a CHO cell, a chicken embryonic fibroblast cell, a hybridoma cell, a baby hamster kidney (BHK) cell, a HeLa cell, an A549 cell, and the like. The skilled person will recognize that the AoHV-1 promoter can be used in many different cells to direct expression of an expression product of interest, and that the type of cell is not critical to the instant invention.

In certain aspects the invention provides a producer cell wherein an AoHV-1 promoter is operably linked to a nucleic acid sequence encoding a TetR protein, preferably wherein the AoHV-1 promoter and sequence encoding TetR are integrated into the genome of the producer cell, preferably wherein said cell is a mammalian cell, preferably a human cell, and in particularly preferred embodiments the producer cell is derived from a PER.C6 cell (see e.g., U.S. Pat. No. 5,994,128) by integration into the genome thereof of the AoHV-1 promoter and sequence encoding TetR. The invention thus also provides a PER.C6 cell comprising a transgene integrated into the genome of said cell, wherein the transgene comprises nucleic acid comprising an AoHV-1 promoter operably linked to a TetR-encoding sequence. In a non-limiting embodiment thereof, the transgene has a sequence as set forth in SEQ ID NO: 20. Such cells thus express TetR, and can for instance be used to produce recombinant adenovirus that encodes an expression product of interest under control of a promoter that can be regulated by TetR, e.g. a CMV or other promoter operably linked to one or more tetO sites, which can be particularly advantageous if the expression product of interest that is encoded by the adenovirus would be toxic to the producer cell or would reduce the stability or yield of the recombinant adenovirus when it would be produced during propagation of the adenovirus. The TetR can in such systems repress the tetO-regulated promoter, e.g. a tetO-regulated hCMV promoter, during production in the producer cell so that the expression product of interest is not or only at very low levels produced during propagation and production of the recombinant adenovirus, leading to improved yields and/or stability of the recombinant adenovirus during production. In one aspect the invention also provides a combination comprising: (i) a producer cell that comprises an AoHV-1 promoter operably linked to a sequence encoding TetR, and (ii) a recombinant adenovirus that comprises a sequence encoding an expression product of interest operably linked to a promoter that is operably linked to one or more tetO sites.

The present invention also provides methods for treating genetic, metabolic or acquired diseases with vectors and viruses comprising AoHV-1 promoter operably linked to a transgene. The method comprising contacting a cell with a sufficient amount of vector or virus of the present invention comprising the AoHV-1 promoter operably linked to a transgene wherein the cell is transformed such that the transgene is expressed in the cell. The cell can be transformed in vitro, ex vivo, or in vivo.

An important aspect of vectors, be it DNA vectors such as plasmid vectors or viral vectors such as adenoviral vectors, is the capacity of these vectors to accommodate desired transgene sequences. Such capacity may be limited by size constraints of the vectors, which may for instance become unstable or even impossible to produce if certain size limits are exceeded. The space taken up by a promoter is therefore an important consideration when designing new vectors, apart from the functional capabilities such promoters should have. The instant AoHV-1 promoter has the advantage that it is relatively short, meaning that at a certain size limit of a vector, more space remains for the transgene, e.g. allowing more epitopes to be included if a transgene is an immunogen or allowing expression of larger proteins, as compared to other promoters of larger size. A further advantage of the AoHV-1 promoter of the present invention is the possibility to combine it with the hCMV promoter in a system, e.g. both promoters on one nucleic acid molecule such as a vector, or one promoter in a cell line and the other promoter on a nucleic acid molecule such as a vector present in the cell line, with very limited to no risk of homologous recombination between the promoter sequences due to low sequence homology between the AoHV-1 promoter and the hCMV promoter.

As used herein, the terms "low sequence homology" and "low sequence identity" as they relate to the hCMV promoter sequence, refer to promoter sequences having less than about 50% identity with the hCMV promoter, and preferably having less than about 40% identify with the hCMV promoter. In addition, the promoter sequences with "low sequence homology" and "low sequence identity" preferably also do not have stretches of continuous identical alignment longer than about 15 nucleic acids, or more preferably no stretches of identical alignment longer than about 14 nucleic acids. In a certain preferred embodiment, the promoter is the AoHV-1 short promoter (SEQ ID NO:1 or SEQ ID NO:30) and the identity with the hCMV promoter is 36% and there are no stretches of continuous identical alignment longer than 14 nucleic acids. In other preferred embodiments, the promoter comprises a fragment of SEQ ID NO:1 or SEQ ID NO:30 having promoter activity, e.g. SEQ ID NO:25 or SEQ ID NO:26. As used herein, alignment refers to methods well known by those skilled in the art, e.g., using algorithms such as BLAST (Basic Local Alignment Search Tool) to align and compare different nucleotide or protein sequences (Altschul, Gish, Miller, Myers, & Lipman, 1990).

The present invention also provides cells or transgenic organisms transformed by vectors or viruses comprising the hCMV promoter and the AoHV-1 promoter, wherein the hCMV promoter and the AoHV-1 promoter are operably linked to transgenes, such that both transgenes are expressed in the cells or the transgenic organism. The hCMV promoter and the AoHV-1 promoter may be present on separate molecules (e.g. one promoter on a plasmid or in a virus and the other promoter in the genome of the cell, or both promoters on a different plasmid, or both promoters in the genome of the cell), or both promoters may be present in a single molecule (e.g. in one chromosome of the genome, or in one plasmid, or in one genome of a virus).

The invention also provides a method for producing a recombinant virus, wherein a transgene is potently expressed when the virus is introduced into a target cell, the method comprising: preparing a construct comprising an AoHV-1 promoter operably linked to a transgene, and incorporating said construct into the recombinant virus and then introducing the vector into the cell, e.g., by infection with the virus. The preparation of the construct as such encompasses the use of standard molecular cloning methods that are well known (see e.g. (Holterman et al., 2004; Lemckert et al., 2006; Vogels et al., 2003); Sambrook, Fritsch and Maniatis, Molecular Cloning: A Laboratory Manual, 2nd edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995), as known to the skilled person and routinely performed in the field of recombinant vector or recombinant virus technology, and exemplified herein. The AoHV-1 promoter has the features as described above, and in view of this disclosure, can be obtained by routine methods such as PCR or de novo nucleic acid synthesis. For convenience, the skilled person may manipulate a virus genome by cloning into smaller fragments, e.g. a first part for the left part of the genome of an adenovirus up to the E1 region for easy manipulation and introduction of the transgenes in plasmid form and a second, larger, part for the remainder of the genome that can upon recombination with the first part result in a complete adenovirus genome (see e.g. WO 99/55132).

"Heterologous nucleic acid" or a "heterologous gene" (also referred to herein as a "transgene", or "gene of interest"), e.g. in vectors or viruses or cells of the invention is nucleic acid that is not naturally present in the vector or virus or cell, or that is not operably linked to the AoHV-1 promoter in nature. It is introduced into the vector or virus or cell for instance by standard molecular biology techniques. It may in certain embodiments encode a protein of interest or part thereof. In such cases, the protein of interest may be referred to as a "heterologous protein", as it is not naturally encoded by a sequence operably linked to the AoHV-1 promoter in nature. A transgene can for instance be cloned into a plasmid vector or into a deleted E1 or E3 region of an adenoviral vector. In some embodiments of the invention, the expression cassette with an AoHV-1 promoter operably linked to a transgene is placed into the E1 region of an adenoviral genome. In some embodiments of the invention, the expression cassette with an AoHV-1 promoter operably linked to a transgene is placed into the E3 region of an adenoviral genome. In some embodiments of the invention, the expression cassette with an AoHV-1 promoter operably linked to a transgene is placed between the E4 region and the right ITR of an adenoviral genome. In other embodiments the expression cassette with an AoHV-1 promoter operably linked to a transgene is present in a plasmid vector. In other embodiments, the expression cassette with an AoHV-1 promoter operably linked to a transgene is integrated into the genome of a cell. Such cells or cell lines can be used to recombinantly express the transgene, e.g. by culturing the cells under conditions wherein the promoter is active (if the non-regulated version of the promoter is used, i.e. if no regulatory elements are added to the promoter, this expression will automatically happen upon culturing) and drives expression of the transgene.

As used herein, the terms "promoter" or "promoter region" or "promoter element" are used interchangeably, and refer to a segment of a nucleic acid sequence, typically but not limited to DNA, that controls the transcription of the nucleic acid sequence to which it is operatively linked. The promoter region includes specific sequences that are sufficient for RNA polymerase recognition, binding and transcription initiation. In addition, the promoter region can optionally include sequences which modulate this recognition, binding and transcription initiation activity of RNA polymerase. These sequences may be cis-acting or may be responsive to trans-acting factors. Furthermore, the promoters may be constitutive or regulated, depending upon the nature of the regulation.

The skilled person will be aware that promoters are built from stretches of nucleic acid sequences and often comprise elements or functional units in those stretches of nucleic acid sequences, such as a transcription start site, a binding site for RNA polymerase, general transcription factor binding sites, such as a TATA box, specific transcription factor binding sites, and the like. Further regulatory sequences may be present as well, such as enhancers, and sometimes introns at the end of a promoter sequence. Such functional units may be directly adjacent to each other but may also be separated by stretches of nucleic acid that do not have a direct role in the promoter function. The skilled person can refer to the examples herein for testing whether nucleotides in the stretch of nucleic acid are relevant for promoter function, and to test the effect of removing or adding nucleotides into a given promoter sequence by standard molecular biology methods, e.g. to minimize its length while retaining promoter activity or to optimize activity. Also mutations may be introduced into the promoter to reduce (stretches of) identity to other promoters (e.g. hCMV) if these promoters are intended to be present or used simultaneously in the same cell.

As used herein, the term "enhancer" refers to regulatory DNA sequences, e.g., 50-1500 bp, that can be bound by proteins (activator proteins) to stimulate or enhance transcription of a gene or several genes. These activator proteins, (a.k.a., transcription factors) interact with the mediator complex and recruit polymerase II and the general transcription factors which then begin transcribing the genes. Enhancers are generally cis-acting, but can be located either upstream or downstream from the start site of the gene or genes they regulate. Furthermore, an enhancer can be either in the forward or backward direction and doesn't need to be located near the transcription initiation site to affect transcription, as some have been found located several hundred thousand base pairs upstream or downstream of the start site. Enhancers can also be found within introns.

Sequences herein are provided in the 5' to 3' direction, as is customary in the art. Also note that the terms 'upstream' and 'downstream' are with respect to the direction of transcription as commonly used in the art. For example, by convention the terms upstream and downstream relate to the 5' to 3' direction in which RNA transcription takes place. Upstream is toward the 5' end of the RNA molecule and downstream is toward the 3' end. When considering double-stranded DNA, upstream is toward the 5' end of the coding strand for the gene in question and downstream is toward the 3' end. Due to the anti-parallel nature of DNA, this means the 3' end of the template strand is upstream of the gene and the 5' end is downstream.

An AoHV-1 promoter according to the invention preferably contains a TATA box sequence, such as a sequence located at positions 251 to 258 in SEQ ID NO: 25. A "TATA box" as defined herein is a DNA sequence that can be bound by TATA binding protein (TBP) and that has the consensus sequence TATAWAWR (where W is A or T, and R is A or G). It is usually located about 25-35 base pairs upstream of the transcription start site. In certain embodiments, an AoHV-1 promoter of the invention comprises TATA box sequence TATATAAG (positions 251-258 in SEQ ID NO: 25). The skilled person would appreciate that said TATA box sequence (i.e. TATATAAG) of an AoHV-1 promoter could be replaced by a similar canonical TATA box sequence, i.e. one that corresponds to the consensus sequence TATAWAWR (where W is A or T, and R is A or G), without an anticipated significant reduction of promoter activity.

An AoHV-1 promoter according to the invention may also contain a (putative) initiator element (Inr) such as located at positions 280 to 286 in SEQ ID NO: 25 (sequence: CCATTCG). In embodiments where an Inr is present, replacement of said Inr sequence (i.e. CCATTCG) of an AoHV-1 promoter by another sequence largely adhering to the Inr sequence YYANWYY (where Y is C or T; N is A, C, G, or T; and W is A or T) is not expected to significantly affect the activity of said promoter.

In certain embodiments wherein a putative Inr is present, an AoHV-1 promoter comprises a TATA box corresponding to positions 251-258, as well as the sequences up to about nt 286, in SEQ ID NO: 25. Without wishing to be bound by theory, it may be beneficial for certain embodiments of an AoHV-1 promoter of the invention to comprise both a TATA box and an Inr, wherein the Inr sequence is located about 25-40, e.g. about 29-36 nt downstream of the first nt of the TATA box.

Also in embodiments where no Inr is present, it is preferred to include at least about 25-35 base pairs downstream of the TATA box and upstream of the coding sequence of the operatively linked gene of interest. The present application includes at least one example of an AoHV-1 promoter that no longer comprises a consensus Inr sequence at the natural location of about 29-35 nt downstream of the first nt of the TATA-box, yet such promoter is still active, demonstrating that the Inr sequence at that position is not essential for a functional promoter.

An AoHV-1 promoter according to the invention is defined herein as a sequence having promoter activity and comprising a sequence having at least 80%, 81%, 82%, 83%, 84%, 85%, 86%, 87%, 88%, 89%, 90%, 91%, 92%, 93%, 94%, 95%, 96%, 97%, 98%, 99% identity, or being 100% identical, to a fragment of at least 50, 100, 150, 200, 250, 300, or 350 nucleotides of SEQ ID NO:25. Preferably, said fragment includes a fragment of at least 50 nt having at least 80%, 81%, 82%, 83%, 84%, 85%, 86%, 87%, 88%, 89%, 90%, 91% 92%, 93%, 94%, 95%, 96%, 97%, 98%, 99% identity, or being 100% identical, to nt 237-286 of SEQ ID NO: 25, and preferably said at least 50 nt include a sequence TATAWAWR (TATA box consensus sequence) at a position corresponding to about nt 251-258 in SEQ ID NO: 25). In certain preferred embodiments therefore, an AoHV-1 promoter of the invention comprises a sequence having at least 80% identity to nt 237-286 of SEQ ID NO: 25.

3' truncations of AoHV-1 promoters of this invention can likely be made downstream of about nt 286 in SEQ ID NO: 25 (i.e. downstream of the putative Inr, which contains the expected transcription start site, which is expected to be at nucleotide 282 in this sequence) without strong effects on promoter activity, whereas larger 3' truncations that remove the putative Inr/transcription start site or, especially, that remove both said putative Inr/transcription start site and said TATA box, are anticipated to result in significant reductions of promoter activity. Indeed, 3' truncated versions of the AoHV-1 short promoter (SEQ ID NO: 30) that did not comprise AoHV-1 sequences downstream of nucleotide 399 (i.e. including only 1 AoHV-1 nucleotide downstream of the putative Inr, with reference to SEQ ID NO: 30, corresponding to nucleotide 287 in SEQ ID NO: 25) were shown to still be active as promoters.

It is demonstrated herein that a relatively short promoter fragment (SEQ ID NO: 26) comprising only 120 nucleotides upstream of its TATA box still has significant promoter activity, which can be increased somewhat further by addition of some further upstream sequences (as for example in SEQ ID NO: 25). By contrast, extension of the AoHV-1 short promoter (SEQ ID NO: 30) at its 3' end (i.e. downstream of the putative Inr/transcription start site) by inclusion of certain further downstream sequences (as for example in SEQ ID NO: 27, SEQ ID NO:28, and SEQ ID NO:29) does not seem to add much activity.

In preferred embodiments, an AoHV-1 promoter of the invention comprises a fragment that is at least 95%, 96%, 97%, 98%, 99% identical, or is 100% identical, to nucleotides 201 to 286 of SEQ ID NO:25.

In more preferred embodiments, an AoHV-1 promoter of the invention comprises a fragment that is at least 95%, 96%, 97%, 98%, 99% identical, or is 100% identical, to nucleotides 187 to 286 of SEQ ID NO:25.

In more preferred embodiments, an AoHV-1 promoter of the invention comprises a fragment that is at least 95%, 96%, 97%, 98%, 99% identical, or is 100% identical, to nucleotides 137 to 286 of SEQ ID NO:25.

In more preferred embodiments, an AoHV-1 promoter of the invention comprises a fragment that is at least 95%, 96%, 97%, 98%, 99% identical, or is 100% identical, to nucleotides 131 to 286 of SEQ ID NO: 25.

In more preferred embodiments, an AoHV-1 promoter of the invention comprises a fragment that is at least 95%, 96%, 97%, 98%, 99% identical, or is 100% identical, to nucleotides 87 to 286 of SEQ ID NO:25.

In more preferred embodiments, an AoHV-1 promoter of the invention comprises a fragment that is at least 95%, 96%, 97%, 98%, 99% identical, or is 100% identical, to nucleotides 37 to 286 of SEQ ID NO:25.

In more preferred embodiments, an AoHV-1 promoter of the invention comprises a fragment that is at least 95%, 96%, 97%, 98%, 99% identical, or is 100% identical, to nucleotides 1 to 286 of SEQ ID NO:25.

In certain embodiments, an AoHV-1 promoter of the invention preferably comprises a sequence having at least 98% identity to at least 200 nucleotides of SEQ ID NO:26 (again preferably comprising at least the Inr and sequences upstream thereof including TATA box and sequences further upstream, e.g. at least about nt 87-286 of SEQ ID NO: 25), more preferably comprises a nucleotide sequence with at least 99% identity, or being 100% identical, to SEQ ID NO:26, still more preferably comprises a nucleotide sequence with at least 99% identity, or being 100% identical, to SEQ ID NO:25. In certain embodiments, the AoHV-1 promoter comprises a fragment of between 240 and 1500 nucleotides, preferably between 240 and 1000 nucleotides, more preferably between 240 and 500 nucleotides that is at least 90%, 91%, 92%, 93%, 94%, 95%, 96%, 97%, 98%, 99% identical, or is 100% identical, to a fragment of SEQ ID NO: 32, wherein said fragment of SEQ ID NO: 32 includes a fragment that is at least 90%, 91%, 92%, 93%, 94%, 95%, 96%, 97%, 98%, 99% identical, or is 100% identical, to nucleotides 201 to 286 of SEQ ID NO:25 (which correspond to nucleotides 1359 to 1444 of SEQ ID NO: 32).

The present invention provides a potent AoHV-1 promoter with a relatively small size, which can be highly advantageous in the context of size limitations of vectors carrying transgenes (i.e. larger transgenes can be accommodated and/or the vectors could remain more stable). Thus, the AoHV-1 promoter of the present invention is preferably less than 2000 nucleotides (2 kb) in length, preferably less than 1 kb, more preferably less than 0.8 kb. In certain preferred embodiments the AoHV-1 promoter is less than 700, less than 650, less than 600, less than 550, less than 500 nucleotides in length. In certain preferred embodiments, the AoHV-1 promoter is at least 200, at least 240, at least 250, at least 300, at least 350, at least 400 nucleotides in length. In certain preferred embodiments the AoHV-1 promoter is 200 to 500, e.g. 240 to 485, nucleotides in length. As shown herein, despite having a relatively short sequence, this novel AoHV-1 promoter was surprisingly capable of directing potent expression of the transgene to which it is operably linked.

A person skilled in the art will recognize that mutations can be made in the provided sequences and the resulting promoters can be tested for promoter activity by routine methods. Also variants of sequences may exist in nature, e.g. in different isolates of a virus, and thus such variants may have some differences in nucleotide sequence but keep the same functionality. Typically, a sequence having at least 90% identity with the indicated promoter sequences will still have functional activity and hence will be considered an AoHV-1 promoter. Thus, the AoHV-1 promoter of the present invention preferably comprises a sequence that has at least 90%, 91%, 92%, 93%, 94%, 95%, 96%, 97%, 98%, or 99% identity, or is 100% identical, to the preferred AoHV-1 promoter sequences provided herein, such as to any one of SEQ ID NO:1, 30, 25, or 26. The skilled person will also be aware that the length of the sequences of the different portions of the provided promoter sequences could be varied to some degree and essentially similar results could be obtained. Testing whether a fragment or mutant sequence of the promoter sequences exemplified herein still has promoter activity, can be performed without undue burden by a person skilled in the art with the information disclosed herein.

A preferred embodiment of an AoHV-1 promoter of the present invention is the AoHV-1 promoter comprising SEQ ID NO:26. The AoHV-1 promoter of the present invention preferably has at least 90%, 91%, 92%, 93%, 94%, 95%, 96%, 97%, 98%, or 99% identity to SEQ ID NO:26, or to a fragment thereof of at least 50, 100, 150, or 200 nucleotides. In a certain preferred embodiment the AoHV-1 promoter is 100% identical to SEQ ID NO:26 or to a fragment thereof of at least 50, 100, 150, or 200 nucleotides.

A further preferred AoHV-1 promoter of the present invention is the AoHV-1 promoter comprising SEQ ID NO:25. In certain embodiments, the AoHV-1 promoter of the present invention preferably has at least 90%, 91%, 92%, 93%, 94%, 95%, 96%, 97%, 98%, or 99% identity, or is 100% identical, to SEQ ID NO:25, or to a fragment thereof of at least 50, 100, 150, 200, 250, 300, or 350 nucleotides. In a certain preferred embodiment the AoHV-1 promoter is 100% identical to SEQ ID NO:25 or to a fragment thereof of at least 50, 100, 150, 200, 250, 300, or 350 nucleotides.

In a further embodiment, a preferred AoHV-1 promoter of the present invention is the AoHV-1 short promoter comprising SEQ ID NO:1 or SEQ ID NO:30. In certain embodiments, the AoHV-1 promoter of the present invention preferably has at least 90%, 91%, 92%, 93%, 94%, 95%, 96%, 97%, 98%, or 99% identity to SEQ ID NO:1, or to a fragment thereof of at least 50, 100, 150, 200, 250, 300, 350 or 400 nucleotides. In a certain preferred embodiment the AoHV-1 promoter is 100% identical to SEQ ID NO:1 or 100% identical to SEQ ID NO:30, or to a fragment of one of these of at least 50, 100, 150, 200, 250, 300, 350 or 400 nucleotides.

In other embodiments, an AoHV-1 promoter of the invention comprises a sequence having at least 90%, 91%, 92%, 93%, 94%, 95%, 96%, 97%, 98%, 99% identity, or that is 100% identical, to SEQ ID NO:22.

In other embodiments, an AoHV-1 promoter of the invention comprises a sequence having at least 90%, 91%, 92%, 93%, 94%, 95%, 96%, 97%, 98%, 99% identity, or that is 100% identical, to SEQ ID NO:23.

In other embodiments, an AoHV-1 promoter of the invention comprises a sequence having at least 90%, 91%, 92%, 93%, 94%, 95%, 96%, 97%, 98%, 99% identity, or that is 100% identical, to SEQ ID NO:27.

In other embodiments, an AoHV-1 promoter of the invention comprises a sequence having at least 90%, 91%, 92%, 93%, 94%, 95%, 96%, 97%, 98%, 99% identity, or that is 100% identical, to SEQ ID NO:28.

In other embodiments, an AoHV-1 promoter of the invention comprises a sequence having at least 90%, 91%, 92%, 93%, 94%, 95%, 96%, 97%, 98%, 99% identity, or that is 100% identical, to SEQ ID NO:29.

In certain other embodiments, an AoHV-1 promoter of the present invention comprises a core promoter (SEQ ID NO:31) operably linked with one or more operator sequences and/or enhancer sequences to modulate transcription, e.g., tetO sequences, operator sequences from the cumate operon, enhancers from naturally occurring enhancer-promoter pairs like SV40 or hCMV (Foecking & Hofstetter, 1986), synthetic enhancers (Schlabach, Hu, Li, & Elledge, 2010), or other regulatory sequences that are well known to those skilled in the art. As used herein, the term "core promoter" is intended to mean a minimum functional unit of the promoter with very low promoter activity on its own, but that can drive potent expression of a transgene when the core promoter is combined with one or more regulatory sequences to modulate transcription from the core promoter, e.g. tetO sequences that can be bound by tetracycline-controlled transactivator protein (tTA). See, for example (Smale, 2001), for a discussion on core promoter sequences.

A transgene operably linked to the AoHV-1 promoter can be potently expressed. As used herein, "potently expressed" or "potent expression" mean that the expression from the AoHV-1 promoter, as measured for example by one of different protein detection techniques such as Western Blot, FACS analysis, or other assays using luminescence or fluorescence, is at least about 30%, 40%, 50%, 60%, 70%, 80%, 90%, 95%, or preferably about 100%, or more than the expression from the hCMV promoter (having SEQ ID NO:4). Of note, the hCMV promoter is much stronger compared to other commonly used promoters such as hPGK, UBI C or RSV LTR promoters (Powell, Rivera-Soto, & Gray, 2015). The hCMV promoters are derived from the major immediate early (mIE) region of human cytomegalovirus and are frequently used for potent gene expression in vaccine and gene therapy vectors. For example, a hCMV promoter sequence can be derived from the hCMV AD169 strain mIE locus (X03922) and include NF1 binding sites, the enhancer region, TATA box and part of the first exon. Other hCMV promoter sequences are known which can be shorter (e.g. only containing the enhancer and promoter region and lacking NF1 binding sites) or longer (e.g. including additional cellular factor binding sites and the first intron sequence). These hCMV promoters which differ in length were all found to be potent ubiquitously active promoters. Examples of truncated hCMV promoters are disclosed in U.S. Pat. No. 7,407,801, incorporated by reference herein. As used herein, a "hCMV promoter" comprises a sequence having at least 80%, preferably at least 85%, 90%, 91%, 92%, 93%, 94%, 95%, 96%, 97%, 98%, 99%, or 100% sequence identity to nt 578-736, preferably to nt 564-736, of SEQ ID NO: 4. A fragment of nt 578-736 of SEQ ID NO: 4 was shown to have promoter activity in experiments in our laboratory (not shown), and a sequence with some mismatches to nt 564-736 of SEQ ID NO: 4 has been shown to provide good expression levels by others (e.g. U.S. Pat. No. 7,407,801 B2, SEQ ID NO: 1 therein). In certain embodiments, a hCMV promoter comprises a sequence having at least 80%, 90%, 91%, 92%, 93%, 94%, 95%, 96%, 97%, 98%, 99%, or 100% sequence identity to SEQ ID NO: 4. For the comparisons of expression levels as described herein, the hCMV promoter sequence was SEQ ID NO:4. For example, the expression level from the AoHV-1 promoter of the present invention in a vector is preferably at least about 30%, 40%, 50%, 60%, 70%, 80%, 90%, 95%, or preferably about 100%, or more of the expression level from a vector where the transgene is under control of a hCMV promoter of SEQ ID NO:4. Furthermore, it is known from rAd expressing an antigen under the control of an hCMV promoter that the expression is sufficient to generate significant T-cell and B-cell immune responses. Similarly, expression of a transgene expressed by an AoHV-1 promoter of the present invention from a rAd is expected to generate a significant T-cell and B-cell immune response to the transgene. For example, if the transgene encoded an antigen to elicit an immune response when administered to a subject, potent expression of the transgene is expected to generate a measurable immune response against the antigen.

The term 'about' for numerical values as used in the present disclosure means the value±10%.

The terms "coding sequence", "sequence encoding", or "encoding" are used interchangeably herein, and refer to the nucleic acid sequence which is transcribed (DNA) and translated (mRNA) into a polypeptide in vitro or in vivo when operably linked to appropriate regulatory sequences.

A polyadenylation signal, for example the bovine growth hormone polyA signal (U.S. Pat. No. 5,122,458) or an SV40 polyA signal, may be present behind the transgenes.

Further regulatory sequences may also be added to constructs comprising the AoHV-1 promoter of the present invention. The term "regulatory sequence" is used interchangeably with "regulatory element" herein and refers to a segment of nucleic acid, typically but not limited to DNA, that modulate the transcription of the nucleic acid sequence to which it is operatively linked, and thus acts as a transcriptional modulator. This modulation of expression can be especially useful in cases where expression of a protein is toxic to the host cell, e.g., where expression is lethal to a host cell or negatively affects cell growth and/or reduces or eliminates protein production. Furthermore, modulation of expression can also be useful in cases where expression causes vector instability or where timing of expression is a consideration for an experiment done in vitro or in vivo. A regulatory sequence often comprises nucleic acid sequences that are recognized by the nucleic acid-binding domains of transcriptional proteins and/or transcription factors that activate or repress transcription. For example, a regulatory sequence could include one or more (e.g., 1, 2, 3, 4, 5, 6, 7, 8, 9, or 10, etc.) tetracycline operator sequences (tetO sites), such that expression is inhibited in the presence of the tetracycline repressor protein (tetR), see e.g. WO 1999/000510 A1. An example of a single tetO sequence is CCCTATCAGTGATAGAG (SEQ ID NO:14). In the absence of tetracycline, the tetR protein is able to bind to the tetO sites and repress transcription of a gene operably linked to the tetO sites. In the presence of tetracycline, however, a conformational change in the tetR protein prevents it from binding to the operator sequences, allowing transcription of operably linked genes to occur. In certain embodiments, a vector or rAd of the present invention can optionally include one or more tetO sites operatively linked to the AoHV-1 promoter, such that expression of one or more transgenes is inhibited in the vectors that are produced in the producer cell line in which tetR protein is expressed. Subsequently, expression would not be inhibited if the vector is introduced into a subject or into cells that do not express the tetR protein (see e.g., WO 07/073513). In certain other embodiments, vectors of the present invention can optionally include a cumate gene-switch system, in which regulation of expression is mediated by the binding of the repressor (CymR) to the operator site (CuO), operably linked, e.g. by placing it close to the transcription start site of the promoter (see e.g., (Mullick et al., 2006)). In other embodiments, the well-known lac repressor system is combined with the promoter of the invention, wherein one or more lac operator sites are operably linked to the promoter, so that binding of lac repressor protein can be used to regulate expression.

As used herein, the term "repressor" refers to entities (e.g., proteins or other molecules) having the capacity to inhibit, interfere, retard and/or repress the production of heterologous protein product of a recombinant expression vector. For example, by interfering with a binding site at an appropriate location along the expression vector, such as in an expression cassette. Examples of repressors include tetR, CymR, the lac repressor, the trp repressor, the gal repressor, the lambda repressor, and other appropriate repressors known in the art.

The terms "operably linked", or "operatively linked" are used interchangeably herein, and refer to the functional relationship of the nucleic acid sequences with regulatory sequences of nucleotides, such as promoters, enhancers, repressor sequences, transcriptional and translational stop sites, and other signal sequences and indicates that two or more DNA segments are joined together such that they function in concert for their intended purposes. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be possible to modify the regulatory sequence for the expression of the nucleic acid or DNA in the cell type for which it is expressed. The desirability of, or need of, such modification may be empirically determined.

The invention also provides a method for expressing a transgene in a cell, the method comprising providing the cell with a recombinant virus, e.g. a recombinant adenovirus, comprising an AoHV-1 promoter operably linked to a transgene. Providing a cell with a recombinant adenovirus can be done via administration of the adenovirus to a subject, or via introduction (e.g. infection) of the adenovirus in vitro or ex vivo into a cell. In certain embodiments the invention provides a recombinant adenoviral vector for use in expressing a transgene in a cell, e.g. by administering the recombinant adenovirus to a subject.

The present invention also provides a method for expressing a transgene in a cell, the method comprising providing the cell with a recombinant virus, e.g. a recombinant adenovirus, comprising the AoHV-1 promoter operably linked to a transgene encoding an expression product such as a protein of interest, for instance wherein the protein of interest is a therapeutic protein or an antigen.

The invention also provides a method for inducing an immune response against an antigen, comprising administering to a subject a vector, e.g. a recombinant adenovirus comprising an AoHV-1 promoter operably linked to a transgene. The invention also provides a vector or a recombinant adenovirus according to the invention for use in inducing an immune response against an antigen.

The AoHV-1 promoter of the invention can in certain embodiments for instance be used to drive expression of an antigen, with the aim of generating an immune response to the antigens in a vaccine application. The identity of the transgene is not material for the instant invention, which is suitable for example with vectors or adenoviruses comprising any transgene. Suitable transgenes are well known to the skilled person, and for instance may include transgene open reading frames, for instance open reading frames coding for polypeptides that have a therapeutic effect, e.g. for gene therapy purposes, or polypeptides against which an immune response is desired when the vector, e.g. rAd vector, is used for vaccination purposes. Particularly preferred heterologous nucleic acids are genes of interest encoding antigenic determinants towards which an immune response needs to be raised. Such antigenic determinants are also typically referred to as antigens. When the recombinant vector is administered to a subject, an immune response will be raised against the antigen(s). Any desired antigen can be encoded by the vector. In typical embodiments according to the invention, antigens are peptides, polypeptides or proteins from organisms that may cause a disease or condition. Therefore, in a further preferred embodiment, said heterologous nucleic acid of interest encodes an immunogenic (or antigenic) determinant. More preferably, said immunogenic determinant is an antigen from a bacterium, a virus, yeast or a parasite. The diseases caused by such organisms are generally referred to as 'infectious disease' (and are thus not limited to organisms that 'infect' but also include those that enter the host and cause a disease). So-called 'self-antigens', e.g. tumour antigens, also form part of the state of the art, and may be encoded by heterologous nucleic acids in the recombinant vectors according to the present invention. Non-limiting examples from which the antigenic determinants (or antigens) are taken are malaria-causing organisms, such as *Plasmodium falciparum*, tuberculosis-causing organism such as *Mycobacterium tuberculosis*, yeasts, or viruses. In other preferred embodiments, antigens from viruses such as flaviviruses (e.g., West Nile Virus, Hepatitis C Virus, Japanese Encephalitis Virus, Dengue Virus, Zika Virus), Ebola virus, Human Immunodeficiency Virus (HIV), and Marburg virus may be used in compositions according to the present invention. Exemplary non-limiting embodiments of antigens are the CS protein or immunogenic part thereof from *P. falciparum*, a protein of one antigen-, or a fusion protein of several antigens from *M. tuberculosis*, such as the Ag85A, Ag85B and/or the TB10.4 proteins or immunogenic part(s) thereof, a viral glycoprotein or immunogenic part thereof, such as GP from a filovirus, such as Ebola virus or Marburg virus, an HIV protein such as gag, pol, env, nef, or variants thereof, or a HA, NA, M, or NP protein, or immunogenic part of any of these, from influenza virus, or a respiratory syncytial virus (RSV) antigen, e.g. RSV F protein or RSV G protein, or both, or other RSV proteins, a human papillomavirus or other virus antigen, etc. The recombinant vector, e.g. rAd may encode one antigen, but may also optionally encode two different antigens from the same organism, or optionally combinations of antigens from different organisms, e.g. a first antigen from a first organism and second antigen from a second organism. It is also possible to encode an antigen and for instance an adjuvant into the same vector such as rAd vector, e.g. an antigen and a Toll-Like-Receptor (TLR) agonist, such as a TLR3 agonist, such as dsRNA or a mimetic thereof or the like (e.g. WO 2007/100908). In certain embodiments, the recombinant vector, e.g. recombinant adenovirus, encodes two different antigens, one under control of the AoHV-1 promoter and one under the control of a different promoter, e.g., the hCMV promoter. In other embodiments, the vector or recombinant virus encodes an antigen and an immune modulator, one of which is under control of the AoHV-1 promoter and the other is under control of a different promoter, e.g., the hCMV promoter. In certain embodiments, further heterologous sequences or transgenes may be present in the vector or recombinant virus, besides the transgene that is under control of the AoHV-1 promoter.

The invention also provides a recombinant DNA molecule comprising the AoHV-1 promoter of the present invention operably linked to a transgene. The invention also provides the genome of a recombinant adenovirus comprising the AoHV-1 promoter operably linked to a transgene. The skilled person will be aware that this may also be a combination of at least two different recombinant DNA molecules that together can form the single recombinant DNA molecule of the invention. Such molecules are useful in manipulating the genome and creating novel recombinant adenoviruses. The genome encodes the proteins that are required for adenovirus replication and packaging in permissive cells.

The term 'recombinant' for a recombinant adenovirus, as used herein implicates that it has been modified by the hand of man as opposed to wild-type adenoviruses, e.g. it comprises a heterologous gene, genes, or parts thereof and an AoHV-1 promoter operably linked to a transgene.

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, 6,113,913, and 8,932,607, and Thomas Shenk, "Adenoviridae and their Replication" M. S. Horowitz, "Adenoviruses", Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques that are well known in the art, such as those described in, for example, Sambrook et al., *Molecular Cloning, a Laboratory Manual,* 2d ed., Cold Spring Harbor Press, Cold Spring Harbor, N.Y. (1989), Watson et al., *Recombinant DNA,* 2d ed., Scientific American Books (1992), and Ausubel et al., Current Protocols in Molecular Biology, Wiley Interscience Publishers, NY (1995), and other references mentioned herein.

An adenovirus according to the invention belongs to the family of the Adenoviridae and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu; in the present invention a human adenovirus is meant if referred to Ad without indication of species, e.g. the brief notation "Ad5" means the same as HAdV5, which is human adenovirus serotype 5), or a simian adenovirus such as chimpanzee or gorilla adenovirus (ChAd, AdCh, or SAdV), or a rhesus monkey adenovirus (RhAd).

Most advanced studies have been performed using human adenoviruses, and human adenoviruses are preferred according to certain aspects of the invention. In certain preferred embodiments, the recombinant adenovirus according to the invention is based upon a human adenovirus. In preferred embodiments, the recombinant adenovirus is based upon a human adenovirus serotype 5, 11, 26, 34, 35, 48, 49 or 50. According to a particularly preferred embodiment of the invention, an adenovirus is a human adenovirus of one of the serotypes 26 and 35. An advantage of these serotypes is a low seroprevalence and/or low pre-existing neutralizing antibody titers in the human population. Preparation of rAd26 vectors is described, for example, in WO 2007/104792 and in (Abbink et al., 2007). Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in (Vogels et al., 2003). Exemplary genome sequences of Ad35 are found in GenBank Accession AC_000019 and in FIG. 6 of WO 00/70071.

The sequences of most of the human and non-human adenoviruses mentioned above are known, and for others can be obtained using routine procedures.

A recombinant adenovirus according to the invention may be replication-competent or replication-deficient.

In certain embodiments, the adenovirus is replication deficient, e.g. because it contains a deletion in the E1 region of the genome. A "deletion in the E1 region" means a deletion in this region as compared to a wild-type adenovirus, and means a deletion in at least one of the E1A, E1B 55K or E1B 21K coding regions, preferably a deletion of E1A, E1B 55K and E1B21K coding regions. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see, e.g., U.S. Pat. No. 5,994,128), E1-transformed amniocytes (See, e.g., EP 1230354), E1-transformed A549 cells (see e.g. WO 98/39411, U.S. Pat. No. 5,891,690), GH329:HeLa cells (Gao, Engdahl, & Wilson, 2000), 293 cells, and the like. In certain embodiments, the producer cells are for instance HEK293 cells, or PER.C6 cells, or 911 cells, or IT293SF cells, and the like.

In addition to adenoviruses, those skilled in the art will recognize that other viruses are also suitable for use as viral vectors using the AoHV-1 promoter of the present invention. For example, adeno-associated viruses (AAV), herpes simplex virus (HSV), paramyxoviruses such as measles virus, alphaviruses, EBNA virus, retroviruses, poxvirus and lentivirus, and the like, can also be engineered to include the AoHV-1 promoter of the present invention. See, for example, reviews about different vectors as discussed in (Heilbronn & Weger, 2010; Robbins & Ghivizzani, 1998; Walther & Stein, 2000).

For administering to humans, one may employ pharmaceutical compositions for instance comprising a vector, a recombinant virus, or a recombinant protein expressed using methods of the present invention, e.g., rAd or a recombinant protein expressed using AoHV-1 promoter of the present invention, and a pharmaceutically acceptable carrier or excipient. In the present context, the term "Pharmaceutically acceptable" means that the carrier or excipient, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). A purified vector, e.g. rAd, or protein, preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. A vector or rAd or protein typically is in a solution having a suitable buffer, and the solution may also contain a salt. Optionally stabilizing agent may be present, such as albumin. In certain embodiments, detergent is added. In certain embodiments, vector, rAd or protein may be formulated into an injectable preparation. These formulations contain effective amounts of the pharmaceutical ingredient, e.g. vector, rAd, or protein, are either sterile liquid solutions, liquid suspensions or lyophilized versions and optionally contain stabilizers or excipients. The pharmaceutical preparations can be prepared for different routes of administration, e.g. intramuscular or intradermal injection, inhalation, intravenous administration, oral administration, etc.

Examples of adenovirus formulations are the Adenovirus World Standard (Hoganson et al., 2002): 20 mM Tris pH 8, 25 mM NaCl, 2.5% glycerol; or 20 mM Tris, 2 mM $MgCl_2$, 25 mM NaCl, sucrose 10% w/v, polysorbate-80 0.02% w/v; or 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Obviously, many other buffers can be used, and several examples of suitable formulations for the storage and for pharmaceutical administration of purified pharmaceutical preparations are known.

In certain embodiments a composition comprising a vector or recombinant virus of the invention, e.g., rAd, further comprises one or more adjuvants. Adjuvants are known in the art to further increase the immune response to an applied antigenic determinant, and pharmaceutical compositions comprising adenovirus and suitable adjuvants are for instance disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the adenovirus vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; and WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvant, e.g. by using heterologous nucleic acid that encodes a fusion of the oligomerization domain of C4-binding protein (C4 bp) to the antigen of interest (Ogun, Dumon-Seignovert, Marchand, Holder, & Hill, 2008), or heterologous nucleic acid encoding a toll-like receptor (TLR) agonist, such as a TLR3 agonist such as dsRNA (see e.g. WO 2007/100908), or heterologous nucleic acid encoding an immunostimulating cytokine, e.g. an interleukin, e.g. IL-12 (see e.g. U.S. Pat. No. 5,723,127), or the like.

A pharmaceutical composition according to the invention may in certain embodiments be a vaccine.

Administration of a vector or recombinant virus of the invention, e.g., adenovirus compositions, can be performed using standard routes of administration. Non-limiting embodiments include parenteral administration, such as by injection, e.g. intradermal, intramuscular, etc, or subcutaneous or transcutaneous, or mucosal administration, e.g. intranasal, oral, and the like. The skilled person knows the various possibilities to administer a composition, e.g. a vaccine in order to induce an immune response to the antigen(s) in the vaccine.

Adenovirus compositions may be administered to a subject, e.g. a human subject. The total dose of the adenovirus provided to a subject during one administration can be varied as is known to the skilled practitioner, and is generally between $1\times10^7$ viral particles (vp) and $1\times10^{12}$ vp, preferably between $1\times10^8$ vp and $1\times10^{11}$ vp, for instance between $3\times10^8$ and $5\times10^{10}$ vp, for instance between $10^9$ and $3\times10^{10}$ vp.

A subject as used herein preferably is a mammal, for instance a rodent, e.g. a mouse, or a non-human-primate, or a human. Preferably, the subject is a human subject.

It is also possible to provide one or more booster administrations of one or more vaccines. If a boosting vaccination is performed, typically, such a boosting vaccination will be administered to the same subject at a moment between one week and one year, preferably between two weeks and four months, after administering the composition to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject as a priming or boosting vaccination.

Various publications, which may include patents, published applications, technical articles and scholarly articles, are cited throughout the specification in parentheses, and full citations of each may be found at the end of the specification. Each of these cited publications is incorporated by reference herein, in its entirety.

Embodiments

Embodiment 1 is a recombinant nucleic acid molecule comprising an Aotine Herpesvirus major immediate early promoter (AoHV-1 promoter) operably linked to a heterologous transgene.

Embodiment 2 is a plasmid vector comprising an AoHV-1 promoter followed by a multiple cloning site.

Embodiment 3 is the recombinant nucleic acid molecule of embodiment 1 or a plasmid vector of embodiment 2, wherein the AoHV-1 promoter is operably linked to a regulatory sequence that modulates transcription from the AoHV-1 promoter.

Embodiment 4 is the recombinant nucleic acid molecule of embodiment 1 or a plasmid vector of embodiment 2, wherein the AoHV-1 promoter is operably linked to a regulatory sequence comprising one or more tetracycline operator sequences (tetO sites).

Embodiment 5 is a recombinant vector or a recombinant virus, comprising a recombinant nucleic acid molecule according to any one of embodiments 1, 3, or 4.

Embodiment 6 is a recombinant vector according to embodiment 5, wherein the vector is a plasmid vector.

Embodiment 7 is a recombinant virus according to embodiment 5, wherein the virus is an adenovirus.

Embodiment 8 is the recombinant adenovirus according to embodiment 7, wherein the adenovirus has a deletion in a region of its genome.

Embodiment 9 is the recombinant adenovirus of embodiment 8, wherein the deletion is in the E1 region, in the E3 region, or in the E1 region and in the E3 region.

Embodiment 10 is a cell comprising a recombinant nucleic acid molecule according to embodiment 1, 3 or 4, a plasmid vector according to embodiment 2, 3 or 4, or a recombinant vector or recombinant virus according to any one of embodiments 5-9.

Embodiment 11 is a cell comprising a recombinant nucleic acid molecule comprising an AoHV-1 promoter in its genome, preferably wherein said promoter is operably linked to a nucleic acid encoding a protein of interest.

Embodiment 12 is a cell comprising: (i) a recombinant nucleic acid molecule comprising an AoHV-1 promoter operably linked to a first transgene, and (ii) a recombinant nucleic acid molecule comprising a hCMV promoter operably linked to a second transgene.

Embodiment 13 is a vector comprising: (i) a recombinant nucleic acid molecule comprising an AoHV-1 promoter operably linked to a first transgene, and (ii) a recombinant nucleic acid molecule comprising a hCMV promoter operably linked to a second transgene.

Embodiment 14 is a method of producing a recombinant adenovirus comprising an AoHV-1 promoter operably linked to a transgene, wherein the transgene is potently expressed when the adenovirus infects a target cell, the method comprising:

a) preparing a construct comprising the AoHV-1 promoter operably linked to a transgene; and b) incorporating said construct into the genome of the recombinant adenovirus.

Embodiment 15 is a method of producing a recombinant nucleic acid molecule comprising an AoHV-1 promoter operably linked to a transgene encoding a protein of interest, the method comprising molecular cloning of the transgene in operable linkage to an AoHV-1 promoter.

Embodiment 16 is a recombinant DNA molecule comprising the genome of a recombinant adenovirus according to any one of embodiments 7-9.

Embodiment 17 is a method for making the cell of embodiment 11, comprising introducing an AoHV-1 promoter into the cell and integrating the AoHV-1 promoter into the genome, preferably wherein said promoter is operably linked to a nucleic acid encoding a protein of interest.

Embodiment 18 is a method for producing an expression product of interest, comprising expressing a transgene encoding the expression product of interest in a host cell, wherein the transgene is operably linked to an AoHV-1 promoter.

Embodiment 19 is the method of embodiment 18, wherein the expression product is a protein.

Embodiment 20 is a method for expressing a transgene of interest, comprising expressing in a host cell the transgene from the recombinant nucleic acid molecule according to any one of embodiments 1, 3, 4, 5 or 6, Embodiment 21 is the method of embodiment 20, wherein the transgene of interest encodes a protein of interest that is expressed in the host cell.

Embodiment 22 is the method of embodiment 19 or 21, further comprising harvesting the protein of interest from the host cell or from a culture medium wherein the host cell is cultured, or from both the host cell and the culture medium.

Embodiment 24 is a method for producing a virus, comprising propagating the virus in a cell that expresses a gene that has a function in propagating said virus, wherein said gene is under control of an AoHV-1 promoter.

Embodiment 25 is the method of embodiment 24, wherein said virus does not produce said gene in functional form from its own genome, and wherein said gene is essential for replication of said virus.

Embodiment 26 is a pharmaceutical composition comprising a recombinant vector or a recombinant virus according to any one of embodiments 5-9 and a pharmaceutically acceptable carrier or excipient.

Embodiment 27 is a cell according to embodiment 11, wherein the AoHV-1 promoter in the genome is operably linked to nucleic acid that encodes a tetracycline repressor (TetR) protein.

Embodiment 28 is a cell according to embodiment 12, wherein the first transgene encodes TetR.

Embodiment 29 is a cell according to embodiment 28, that further comprises a recombinant adenovirus which comprises the recombinant nucleic acid molecule comprising a hCMV promoter operably linked to the second transgene.

Embodiment 30 is a cell according to embodiment 29, wherein the hCMV promoter can be regulated by TetR, e.g. by being operably linked to one or more tetO sites.

Embodiment 31 is a cell according to embodiment 27, 28, 29, or 30, wherein the cell is a PER.C6 cell.

Embodiment 32 is a method according to embodiment 20, wherein the transgene encodes TetR.

Embodiment 33 is a method according to embodiment 32, wherein the cell is a PER.C6 cell.

Embodiment 34 is a method for propagating a recombinant adenovirus, the method comprising propagating a recombinant adenovirus that encodes a transgene under control of a hCMV promoter that is operably linked to one or more tetO sites in a cell according to embodiment 27, 29, or 31, and preferably isolating the recombinant adenovirus.

Embodiment 35 is any one of the preceding embodiments, wherein the AoHV-1 promoter comprises a sequence having at least 80% identity to nt 237-286 of SEQ ID NO: 25.

Embodiment 36 is any one of the preceding embodiments, wherein the AoHV-1 promoter comprises a sequence having at least 86% identity, preferably at least 90% identity, preferably at least 96% identity, preferably at least 98% identity, more preferably 100% identity, to nt 237-286 of SEQ ID NO: 25.

Embodiment 37 is any one of the preceding embodiments, wherein the AoHV-1 promoter comprises a sequence having at least 90% identity to nt 131-286 of SEQ ID NO: 25.

Embodiment 38 is any one of the preceding embodiments, wherein the AoHV-1 promoter comprises a sequence that is at least 95% identical to SEQ ID NO:31.

Embodiment 39 is any one of the preceding embodiments, wherein the AoHV-1 promoter comprises between 240 and 1500 nucleotides, preferably between 240 and 1000 nucleotides, more preferably between 240 and 500 nucleotides of SEQ ID NO:32.

Embodiment 40 is any one of the preceding embodiments, wherein the AoHV-1 promoter comprises SEQ ID NO:26.

Embodiment 41 is any one of the preceding embodiments, wherein the AoHV-1 promoter comprises a sequence that is at least 95% identical to a fragment of at least 300 nucleotides of SEQ ID NO:25.

Embodiment 42 is any one of the preceding embodiments, wherein the AoHV-1 promoter comprises SEQ ID NO:25.

Embodiment 43 is any of the preceding embodiments, wherein the AoHV-1 promoter comprises a sequence that is at least 95% identical to a fragment of at least 400 nucleotides of SEQ ID NO:1.

Embodiment 44 is embodiment 43, wherein the AoHV-1 promoter comprises SEQ ID NO:1 or SEQ ID NO:30.

Embodiment 45 is a cell comprising a transgene that comprises SEQ ID NO: 20, preferably within the genome of the cell.

Embodiment 46 is a cell according to embodiment 45, wherein the cell is a PER.C6 cell.

EXAMPLES

Without further description, it is believed that one of ordinary skill in the art can, using the preceding description and the following illustrative methods and examples, make and utilize the present invention and practice the claimed methods. The following working examples therefore, specifically point out certain embodiments, features, and advantages of the present invention, and are not to be construed as limiting in any way the remainder of the disclosure. The examples merely serve to clarify the invention.

Methods

Cell Culture:

HEK293 cells were maintained in Dulbecco's modified Eagle's medium (DMEM) with 10% fetal bovine serum (FBS). Vero cells were cultured in Minimal Essential Medium (MEM, Life Technologies) supplemented with 5% fetal bovine serum (FBS). PER.C6 cells (Fallaux et al., 1998) were cultured in DMEM with 10% fetal bovine serum (FBS), supplemented with 10 mM $MgCl_2$.

PER.C6-hCMV.TetR cells (described herein) were cultured in similar medium as described above for PER.C6 cells but supplemented with 2 ug/ml Blasticidin (Gibco A11139-03).

Subculturing of above cells was performed according to standard protocols using TrypLE Select Enzyme (ThermoFisher, Cat. No.: 12563011) to detach cells.

Padapt35 Plasmids:

Different promoter constructs were cloned into pAdApt35 (Vogels et al. 2007) using AvrII and HindIII restriction sites. A gene encoding for firefly luciferase was inserted using HindIII and XbaI restriction sites, resulting in pAdapt plasmids in which the Luc gene is expressed under the different tested promoters (pAdapt35.P.Luc). These plasmids were used in Example 1.

Expression Analysis in Transiently Transfected HEK293 Cells.

HEK293 cells were plated in multiwell 6 Poly-L-Lysine (PLL) coated plates and transfected with 1 μg pAdapt.P.Luc plasmids using Lipofectamine according to the instructions provided by the manufacturer (Life Technologies). Subsequently the plates were incubated 24 hours in 37° C., 10% $CO_2$. Luciferase activity was measured 24 h post transfection in cell lysates in presence with 0.1% DTT (1M), in Luminoskan™ Ascent Microplate Luminometer. As a control of transfection efficiency, a plasmid encoding secreted embryonic Alkaline Phosphatase was co-transfected (80 ng/well). SEAP levels were measured using the Clontech Great EscAPe™ SEAP Chemoluminescence Kit 2.0 and a Trilux Microbeta workstation. Expression analysis in transiently transfected HEK293 cells is used in Example 1.

Expression Analysis of *Gaussia* Luciferase Under Control of the tTA-Responsive Artificial Promoter "7xTetO-AoHV-1" in Transiently Transfected Vero Cells Vero cells were seeded in multiwell 96 plates with a seeding density of $1.25\times10^4$ cells/well. Cells were transfected 1 day post seeding with a pDualLuc-derived plasmid containing the *Gaussia* luciferase gene under control of 7xtetO-AoHV-1. Besides the Luciferase plasmid, cells were co-transfected with a plasmid encoding the tetracycline-controlled transactivator (tTA) protein, or with a negative control plasmid (pBluescript). Cell transfection was performed using Lipofectamine 3000 according to manufacturer's protocol (Life Technologies). Luciferase activity was measured at 24 hours post transfection using the Pierce *Gaussia*-Firefly Luciferase Dual Assay kit (Thermo Scientific) in a Luminoskan™ Ascent Microplate Luminometer. To control for transfection efficiency, the measured *Gaussia* Luciferase units were normalized to levels of Red Firefly luciferase (for which the expression cassette, driven by AoHV-1 short, was located on the same pDualLuc plasmid). Expression analysis in transiently transfected Vero cells was performed in Example 2.

Expression Analysis of *Gaussia* Luciferase Under Control of AoHV-1 Promoter Variants in Transiently Transfected PER.C6 Cells PER.C6 cells were seeded in multiwell 96 plates with a seeding density of $5\times10^4$ cells/well. Cells were transfected 1 day post seeding using the pDualLuc plasmids containing the *Gaussia* luciferase gene under control of different AoHV-1 promoter variants, as described in Example 6. Cell transfection was performed using Lipofectamine 2000 CD according to manufacturer's protocol (Life Technologies). Luciferase activity was measured on cells lysed at 24 hours post transfection using the Pierce *Gaussia*-Firefly Luciferase Dual Assay kit (Thermo Scientific) and a Luminoskan™ Ascent Microplate Luminometer. To control for transfection efficiency, the measured *Gaussia* Luciferase units were normalized to levels of Red Firefly luciferase (for which the expression cassette, driven by AoHV-1 short, was located on the same pDualLuc plasmid). This methods section is applicable for Example 6.

PER.C6-hCMV.TetR and PER.C6-AoHV.TetR Cells

Two types of PER.C6 cells stably expressing TetR were generated and used herein. First, PER.C6-hCMV.TetR cells, which express TetR under control of a hCMV promoter, were generated by stable transfection of PER.C6 cells with plasmid pCDNA6/TR (Thermo Fisher Scientific Cat. No.: V102520) according to standard procedures described in the manufacturer's protocol.

Second, PER.C6-AoHV.TetR cells, which express TetR under control of the AoHV-1 short promoter, were generated by stable transfection of PER.C6 cells with plasmid pC_AoHV_TetR according to procedures described in Example 5 (and the methods section referred to therein).

Cell Clone Generation of PER.C6-hCMV.TetR Cells Expressing an Additional Gene of Interest Under Control of a TetR-Regulated AoHV-1 Short Promoter PER.C6-hCMV.TetR cells were seeded 1 day before transfection in a T80 culture flask. The plasmid used for transfection carried a gene of interest (GOI) under control of the AoHV.2xtetO promoter (SEQ ID NO:7). Additionally it contains a neomycin phosphotransferase II gene expression cassette controlled by the SV40-derived promoter. The plasmid was constructed by replacement, via several cloning steps, of the hCMV promoter-containing MfeI-XbaI fragment of pcDNA2004Neo(−) (GenBank accession FB674876) by a fragment comprising AoHV.2xtetO followed by the coding sequence of the GOI. Transfection was done with Lipofectamin 2000 according to the manufacturer's protocol (Invitrogen). The day after transfection, the cells were subcultured and seeded 1:2, 1:4, 1:8 and 1:16 in 10-cm culture dishes. One day after seeding, the cell culture medium was replaced with PER.C6-hCMV.TetR medium supplemented with 0.5 mg/ml Geneticin (Gibco 10131-019). Medium was replaced 2× per week. Clones were picked 2-3 weeks post transfection. This methods section is applicable for Example 3.

Western Blot to Analyse Expression of a Gene of Interest

Seeded cells were incubated for 2 days with or without Doxycycline (1 g/ml) and harvested in RIPA buffer (150 mM NaCl, 1% triton X100, 0.5% Doxycholate, 0.1% SDS 50 mM tris-HCL).

Samples were loaded on a 10% bis-tris gel (Invitrogen NP0301PK2) and run in MOPS buffer (Invitrogen NP0001). The SDS gel was blotted in a iBlot2 system (Invitrogen) and proteins were transferred to a nitrocellulose membrane (Invitrogen IB23001). The membrane was blocked overnight at 4° C. in blocking buffer (LI-COR 927-40000). The Western blot membrane was incubated with primary antibody (1:200 mouse polyclonal against Ad35 virus (in-house)) in blocking buffer for 2 hours and washed with TBST. Western blot was incubated with secondary antibody (1:5000 Goat anti-mouse-800CW) in blocking buffer for 1 hour and washed multiple times with TBST. Visualization was done on the LI-COR Odessey Imager. This methods section is applicable for Example 3.

Generation of Dual Luciferase Plasmid pDualLuc pDualLuc (SEQ ID NO:21) is a plasmid carrying two expression cassettes: a first expression cassette expressing *Gaussia* luciferase (Gluc) under control of the human cytomegalovirus (hCMV) promoter, and a second cassette expressing red firefly luciferase (RFL) under control the AoHV-1 short promoter. Within pDualLuc, the Gluc and RFL expression cassettes are positioned in a tail-to-tail orientation relative to each other.

pDualLuc was generated by several gene synthesis and subcloning steps performed at GeneArt (Life Technologies). First, synthetic fragments "CMV_GLuc_SV" (SEQ ID NO:17) and "AoHV1_RFL_BGH" (SEQ ID NO:19), which carry the respective expression cassettes, were generated and cloned in a standard GeneArt plasmid (pMK-RQ). Subsequently, synthetic fragment AoHV1_RFL_BGH was further subcloned into the CMV_GLuc_SV-containing construct, using MluI and NsiI restriction sites.

The *Gaussia* luciferase-driving CMV promoter sequence of pDualLuc is flanked by unique restriction sites XhoI and HindIII, allowing for the replacement of this promoter by alternative promoter sequences, as was done herein in Examples 2 and 6.

Generation of Ad26 vector genome plasmid pAd26.dE1.dE3.5orf6 pAd26.dE1.dE3.5orf6 is a plasmid containing a full-length Ad26 vector genome that carries an E1 deletion, an E3 deletion, and a replacement of Ad26 E4 orf6 by that of Ad5, as described for previously generated Ad26-based vectors (Abbink et al., 2007). The plasmid backbone of pAd26.dE1.dE3.5orf6 comprises a pMB1 origin of replication and an ampicillin resistance gene, and is derived from pBR322 (GenBank accession J01749.1). pAd26.dE1.dE3.5orf6 further contains a unique AsiSI restriction site in place of the E1 deletion of the vector genome, and a unique PacI restriction site in between the E4 region and the right inverted terminal repeat (RITR) of the vector genome. These sites can be used to insert transgene cassettes at the respective locations. Finally, the adenovirus vector genome within pAd26.dE1.dE3.5orf6 is flanked at each of its termini by a SwaI restriction site, allowing for its release from the plasmid backbone by SwaI digestion.

Construction of pAd26.dE1.dE3.5orf6 involved several synthesis and cloning steps. A 2-kb sequence (SEQ ID NO:16) containing a left-end and a right-end fragment of the (desired) Ad26 vector genome was synthesized at GeneArt/LifeTechnologies. The left-end vector genome fragment of this sequence spans from the left inverted terminal repeat (LITR) of the vector genome up to and including the SfiI site that corresponds to the SfiI site at positions 3755 to 3767 of the (wild type) Ad26 viral genome (GenBank accession EF153474.1). The right-end viral genome fragment spans from the NheI site corresponding to the NheI site at positions 34079 to 34084 of the wild type Ad26 viral genome up to and including the right ITR (RITR). The synthesized sequence was designed to carry the E1 deletion (from position 472 to 3365 of Ad26, GenBank accession EF153474.1) as well as the restriction sites mentioned above (i.e. the AsiSI site in place of E1 deletion, the PacI site between E4 and RITR, and the two SwaI sites directly flanking the vector genome sequences). The gene synthesis fragment further contained two outer restriction sites to facilitate cloning: an MfeI site was included at the left-end side, while an AseI site was included at the right-end side. The synthesized fragment was ligated, as an MfeI-AseI restriction fragment, into EcoRI- and NdeI-digested pBR322 (GenBank accession J01749.1) (thereby replacing the 2.3-kb, tetracyclin resistance gene-containing EcoRI-NdeI fragment of pBR322), leading to the abolishment of the restriction sites that had been digested to generate the respective ligation fragments. The resulting plasmid, carrying the left and right ends of the vector genome, was finally used to construct pAd26.dE1.dE3.5orf6 by two sequential cloning steps. First, a 12.7-kb SfiI-NheI Ad26 vector genome restriction fragment derived from of pWE.Ad26.dE3.5orf6 (Abbink et al., 2007) was ligated into the "left-end/right-end" plasmid digested by SfiI and NheI. Second, a 13.7-kb SfiI-SfiI Ad26 vector genome restriction fragment derived from pWE.Ad26.dE3.5orf6 was inserted into the SfiI site of the resultant partial vector genome plasmid.

Generation of Ad26 Vector Genome Plasmids pAd26.CMV_GLuc.AoHV1_RFL and Pad26.Cmvteto_Gluc.Aohv1_RFL pAd26.CMV_GLuc.AoHV1_RFL is a plasmid containing the Ad26 vector genome of pAd26.dE1.dE3.5orf6 (see above), modified to carry two transgene expression cassettes: (1) a human cytomegalovirus (hCMV) promoter-driven *Gaussia* luciferase (Gluc) expression cassette inserted in the (deleted) E1 region, and (2) an AoHV-1 promoter-driven red firefly luciferase (RFL) expression cassette inserted in between E4 and the RITR.

pAd26.CMVtetO_GLuc.AoHV1_RFL is identical to pAd26.CMV_GLuc.AoHV1_RFL except that it additionally carries two tetracycline operator (tetO) sequences within the hCMV promoter of the GLuc expression cassette.

Construction of plasmids pAd26.CMV_GLuc.AoHV1_RFL and pAd26.CMVtetO_GLuc.AoHV1_RFL involved the generation of intermediate constructs carrying the required expression cassettes, followed by insertion of these cassettes into the Ad26 vector genome of pAd26.dE1.dE3.5orf6 by Gibson assembly (Gibson et al., 2009). Intermediate constructs carrying synthetic sequences "CMV_GLuc_SV" (SEQ ID NO:17), "CMVtetO_GLuc_SV" (SEQ ID NO:18), and "AoHV1_RFL_BGH" (SEQ ID NO:19) were generated at gene synthesis service provider GeneArt (LifeTechnologies). Sequence CMV_GLuc_SV contains an expression cassette for the expression of GLuc. It comprises a human cytomegalovirus (hCMV) promoter (SEQ ID NO:4), a Gluc coding sequence, and an SV40-derived polyadenylation signal sequence. Sequence CMVtetO_GLuc_SV differs from sequence CMV_GLuc_SV in that it carries, within its hCMV promoter-derived promoter, CMVtetO (SEQ ID NO:15), a 54-bp insertion containing two tetracycline operator (tetO) sequences. Sequence AoHV1_RFL_BGH contains an expression cassette for the expression of RFL. It comprises AoHV-1 short (SEQ ID NO:30), an RFL coding sequence, and a bovine growth hormone gene-derived polyadenylation signal sequence. Sequences CMV_GLuc_SV and CMVtetO_Gluc_SV were designed to additionally contain short flanking sequences corresponding to sequences directly flanking the AsiSI site of pAd26.dE1.dE3.5orf6. These flanking sequences allow for insertion of the concerning expression cassettes into the AsiSI site of pAd26.dE1.dE3.5orf6 (i.e. at the location of the E1 deletion of the Ad vector genome) by way of in vitro assembly (IVA) methods (as for instance described by Gibson et al. (Gibson et al., 2009). Similarly, sequence AoHV1_RFL_BGH contains flanking sequences that allow for the insertion of the concerning expression cassette into the PacI site of pAd26.dE1.dE3.5orf6 (i.e. in between the E4 region and the RITR of the vector genome) by IVA. All three sequences were further equipped with flanking outer restriction sites meant to release these sequences from their respective plasmid backbones (in which they are provided by the gene synthesis service supplier). pAd26.CMV_GLuc.AoHV1_RFL was constructed by performing a 4-fragment Gibson assembly reaction (New England Biolabs) between plasmid pAd26.dE1.dE3.5orf6, digested by both AsiSI and PacI, and synthesized sequences CMV_GLuc_SV and AoHV1_RFL_BGH, which were released from their respective plasmid backbones by digestion by, respectively, PmlI and PshAI. pAd26.CMVtetO_GLuc.AoHV1_RFL was generated in the same way as pAd26.dE1.dE3.5orf6, but using synthesized sequence CMVtetO_GLuc_SV instead of CMV_Gluc_SV in the Gibson assembly reaction.

Primers for Analysis of Transgene Cassette Integrity

"E1 PCR" primer pair sequences:

```
forward
                                    (SEQ ID NO: 9)
TGGCGCGAAAACTGAATGAG -

reverse
                                    (SEQ ID NO: 8)
GCAGGCGGGTTGTCAAATAAG -
```

"E4 PCR1" primer pair sequences:

```
forward
                                    (SEQ ID NO: 10)
GACGGGAGCAATCCCTCCAG -

reverse
                                    (SEQ ID NO: 11)
CCCCACAAAGTAAACAAAAG -
```

"E4 PCR2" primer pair sequences:

```
forward
                                    (SEQ ID NO: 12)
CGTTCTCACTTCCTCGTATC -

reverse
                                    (SEQ ID NO: 13)
CAACGCTGATTGGACGAG -
```

The plasmids described in this sections are used in Example 4.

TetR-Expression Plasmid pC_AoHV_TetR

Figure 6A:
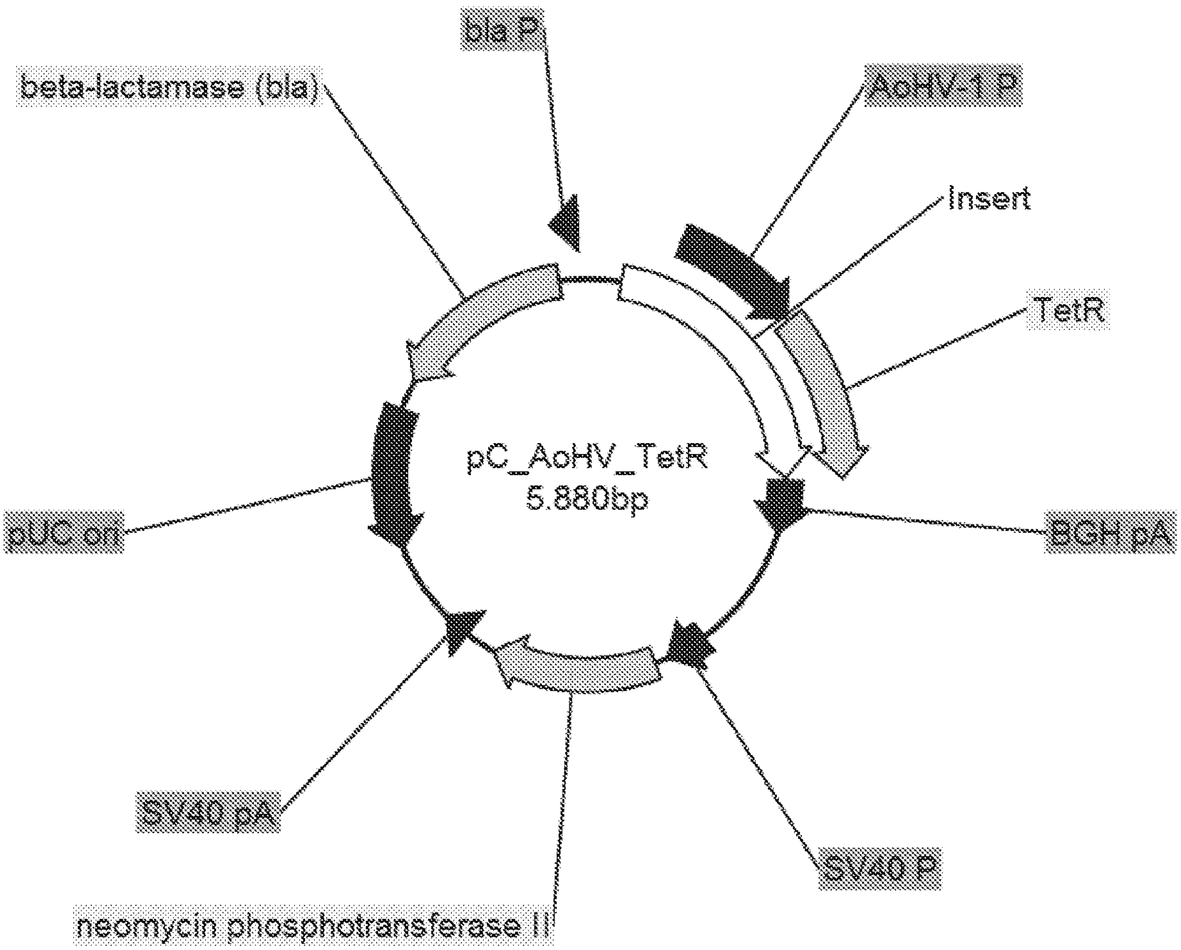
FIGS. 6A, 6B, and 6C.

To construct pC_AoHV_TetR, a 1.3-Kbp DNA (SEQ ID NO:20) fragment comprising AoHV-1 short (SEQ ID NO:30) followed by a codon-optimized TetR-coding sequence was synthesized (at GeneArt/LifeTechnolgies) and subsequently subcloned into pcDNA2004Neo(−) (GenBank accession FB674876) using MfeI and XbaI restriction sites. FIG. 6A shows a map of pC_AoHV_TetR in which the location of the 1.3-Kbp insertion is indicated.

PER.C6-AoHV.TetR Cell Line Generation Procedures

PER.C6-AoHV.TetR stable cell lines were generated by standard cell line generation procedures. Briefly, serum-free grown, suspension-adapted PER.C6 cells (Fallaux et al., 1998) grown in CDM4 PerMAb medium (HyClone) supplemented with 4 mM L-Glutamine (Lonza) were transfected with plasmid pC_AoHV_TetR by electroporation using a BioRad electroporator. After recovery and antibiotic selection in "PerMab selection medium", i.e. CDM4 PerMAb medium supplemented with 4 mM L-Glutamine and 125 ug/mL Geneticin (Gibco), the transfected cells were seeded for single cell cloning in MW96 plates at 1 viable cell per well in MAb medium (SAFC) supplemented with 4 mM L-Glutamine and 125 ug/mL Geneticin. Upon formation of cell colonies, isolated clones were expanded for several passages in static cultures in PerMAb selection medium. 100 clones were subsequently analyzed for ability to express TetR by a flow cytometry intracellular staining procedure using an anti-TetR antibody (Tet03, MoBiTec). In this first screen, 94 of the 100 tested clones were found to be TetR-positive. 47 of these TetR-positive clones were selected and, after adaptation to growth in Permexcis medium (Lonza) supplemented with 4 mM L-Glutamine and 125 ug/mL Geneticin, tested again for TetR expression by flow cytometry intracellular staining procedure, as well as for TetR activity by a TetR functionality assay (described in the methods section herein). 24 TetR-positive clones were then selected that displayed population doubling times of 30 hours or lower, and that represented a broad range of TetR activity levels. These clones, denoted PER.C6-AoHV.TetR clones #1 to #24, were (re-) adapted to growth in shaker flasks after which they were finally cryopreserved in small-scale research cell banks. This methods section is applicable for Example 5.

Stability of TetR Expression from PER.C6-AoHV.TetR Clones

Analysis of the stability of TetR expression by PER.C6-AoHV.TetR cell clones upon extended passaging. PER.C6-AoHV.TetR cell clones were grown in shaker flasks, with and without antibiotic selection, for multiple passages until approximately 60 population doublings (or generations) were reached. TetR expression was analyzed by flow cytometry intracellular staining at generations 20, 40, and 60. At each of these timepoints, cells of each clone were subjected to a flow cytometry intracellular double-staining protocol to detect both TetR and Tubulin. The staining was according to standard flow cytometry intracellular procedures and included two antibody incubation steps: a first with an anti-TetR mouse monoclonal antibody (Tet03, MoBiTec), and a second with an anti-mouse IgG-FITC conjugate (554001, BD Biosciences) in combination with an anti-Tubulin antibody-Alexa Fluor 647 conjugate (ab195884, Abcam). Per clone, the fractions of TetR-positive and -negative cells were determined within a stringent Tubulin-positive gate. This methods section is applicable for Example 5.

TetR Functionality Assay

The TetR functionality assay was performed after extended passaging of the PER.C6-AoHV.TetR cell clones. PER.C6-AoHV.TetR cell clones were grown in shaker flasks, with and without antibiotic selection, for multiple passages until approximately 60 population doublings (or generations) were reached. Then, PER.C6-AoHV.TetR cell clones and control PER.C6 cells were seeded in Poly-L-Lysine-coated multiwell 96plates in Permexcis medium supplemented with 4 mM L-Glutamine, and, after 2 hours of incubation, infected in quadruplicates by the vectors Ad26.CMV_GLuc.AoHV1_RFL and Ad26.CMVtetO_GLuc.AoHV1_RFL (described in Example 4). At one day post infection, the infected cells were harvested in Luciferase Cell Lysis Buffer (Pierce/Thermo Scientific). Using separate aliquots of each cell lysate, GLuc and RFL activities were subsequently measured according the manufacturers' instructions using, respectively, BioLux *Gaussia* Luciferase Assay Kit (NEB) and Luciferase Glow Assay Kit (Pierce/Thermo Scientific) reagents, and the Luminoskan Ascent Microplate Luminometer (Thermo Scientific). Per infection replicate, Gluc activity was normalized by RFL activity. This methods section is applicable for Example 5.

Example 1: Identification of AoHV-1 Short as a Potent Promoter for Heterologous Gene Expression Often, promoters derived from viruses or animal/human genomes are used for heterologous protein expression, e.g. in expression cassettes in plasmid vectors or viral vectors for expressing a gene of interest in cells or a host organism. A promoter commonly used for this purpose is a promoter derived from the immediate early region of human cytomegalovirus (hCMV) (Powell et al., 2015). Several cytomegaloviruses (CMVs) that infect other hosts are also known. They infect, for example, rhesus monkeys (rhCMV) (Barry, Alcendor, Power, Kerr, & Luciw, 1996; Chan, Chiou, Huang, & Hayward, 1996; Chang et al., 1993; Hansen, Strelow, Franchi, Anders, & Wong, 2003), and chimpanzees (chCMV) (Chan et al. 1996).

In order to identify a promoter that is preferably potent and short and also has low sequence identity with the commonly used hCMV promoter, several putative promoter sequences were identified and tested. Several putative promoters that we tested and that were derived from herpesviruses more distantly related to hCMV showed very low or no promoter activity at all. For some other promoters derived from different CMV species and that were known to be potent promoters, we confirmed promoter activity, but unfortunately such promoters often display one of the following disadvantages: either they are characterized by larger size due to e.g. inclusion of enhancer and intron sequences and/or they display considerable homology to the hCMV promoter sequence.

The aotine herpesvirus 1 (AoHV-1) is tentatively classified as a cytomegalovirus. Interestingly, while the complete genome sequence of the AoHV-1 is published and the open reading frames (ORFs) are annotated in the sequence, no major immediate early promoter has been described so far. We tested two different designs of differing length of a region of the AoHV-1 genome, and called the respective putative promoter sequences AoHV-1 long and AoHV-1 short. Based on results described below, where we demonstrate promoter activity for these sequences, we refer to these and their derivatives as the AoHV-1 major immediate early promoter, or briefly to AoHV-1 promoter.

In order to test the identified putative promoter sequences for potency of heterologous gene expression, we had the putative promoter sequences synthesized at GeneArt LifeTechnologies and subcloned into pAdapt35.Luc plasmids via AvrII and HindIII restriction sites upstream of the Firefly Luciferase reporter gene. Firefly luciferase levels were measured in transfected HEK293 cells 24 h post transfection and compared to the Firefly luciferase expression induced by the hCMV promoter (SEQ ID NO:4).

Selecting from a panel of possible promoters, we chose some potent promoters (data not shown), of which chCMV short and AoHV-1 short would be preferred due to their very small size and potency. Results of potency testing for selected promoter AoHV-1 short (SEQ ID NO:1), AoHV-1 long (SEQ ID NO:2), chCMV short (SEQ ID NO:3) and hCMV promoter are shown in FIG. 1. AoHV-1 short, AoHV-1 long, chCMV short and hCMV promoters all show comparable promoter potency in this experiment.

However, as shown in FIG. 2A, chCMV short has a very high sequence identity with hCMV in the alignment region (sequence identity ca. 64%), especially the downstream portion of the chCMV short promoter shows significant alignment and long stretches of sequence identity with hCMV (with several identical stretches of up to 19 nucleotides and a homologous stretch of more than 100 nucleotides with only few nucleotide differences). In contrast, as shown in FIG. 2B, the novel promoter AoHV-1 short has low sequence identity with hCMV in the alignment region (sequence identity ca. 36%) and potency that is comparable to the hCMV control. With respect to potential homologous recombinations between homologous promoter regions, the length of identical stretches in the two sequences is more relevant than the overall sequence homology. Of note, AoHV-1 short promoter shares only few short identical sequence stretches with hCMV with a maximum length of 14 nucleotides, which is believed to result in a very low risk of homologous recombination between hCMV promoters and AoHV-1 short, as compared to promoters sharing more and/or longer stretches of identical nucleotides, e.g., (Rubnitz & Subramani, 1984). Therefore the risk for undesired homologous recombination between hCMV and AoHV-1 short promoters is considered very low. If desired, the already very limited level of sequence identity between these promoters could even be further reduced by making one or more targeted mutations in either promoter and testing by routine methods that this does not abrogate promoter activity.

In conclusion, the AoHV-1 short promoter is preferred because it showed very good potency, in the range of the gold standard hCMV, while at the same time having a very short sequence (484 bp) and low sequence identity with the hCMV promoter.

Example 2: Application of the AoHV-1 Core Promoter in a Small Molecule-Controllable Transactivator-Based System for Inducible Expression of a Gene of Interest in Mammalian Cells Inducible expression of genes can have high applicability in the field of biotechnology, in particular for the transient expression of toxic gene products. Certain well-established systems for heterologous gene regulation in mammalian cells make use of artificial promoters consisting of multiple copies of the Tet operator (TetO) sequence linked to the hCMV core promoter (Gossen & Bujard, 1992; Gossen et al., 1995). In these systems, said artificial promoters, which display no or very low basal transcriptional activity, can become activated by the specific binding to their TetO sequences of certain recombinant transcription factors known as the tetracycline-controlled transactivator protein (tTA) or the reverse tetracycline-controlled transactivator protein (rtTA). Here we tested whether a similar such tTA/rtTA-responsive artificial promoter could be generated using, instead of the hCMV core promoter, a sequence element of the AoHV-1 promoter.

To this end, a promoter was constructed where only the putative minimal (core) AoHV-1 promoter was placed immediately downstream of seven Tet operators (7xTetO-AoHV-1, SEQ ID NO:5). The promoter sequence was synthesized at GeneArt LifeTechnologies and subcloned into plasmid pDualLuc, described in the Methods section herein, via XhoI and HindIII restriction sites, thereby replacing the CMV promoter controlling the *Gaussia* Luciferase reporter gene of this plasmid. *Gaussia* luciferase levels were measured in transfected Vero cells 24 h post transfection and compared to the *Gaussia* luciferase expression by the same promoter in the presence of the transactivator protein tTA.

Figure 3:
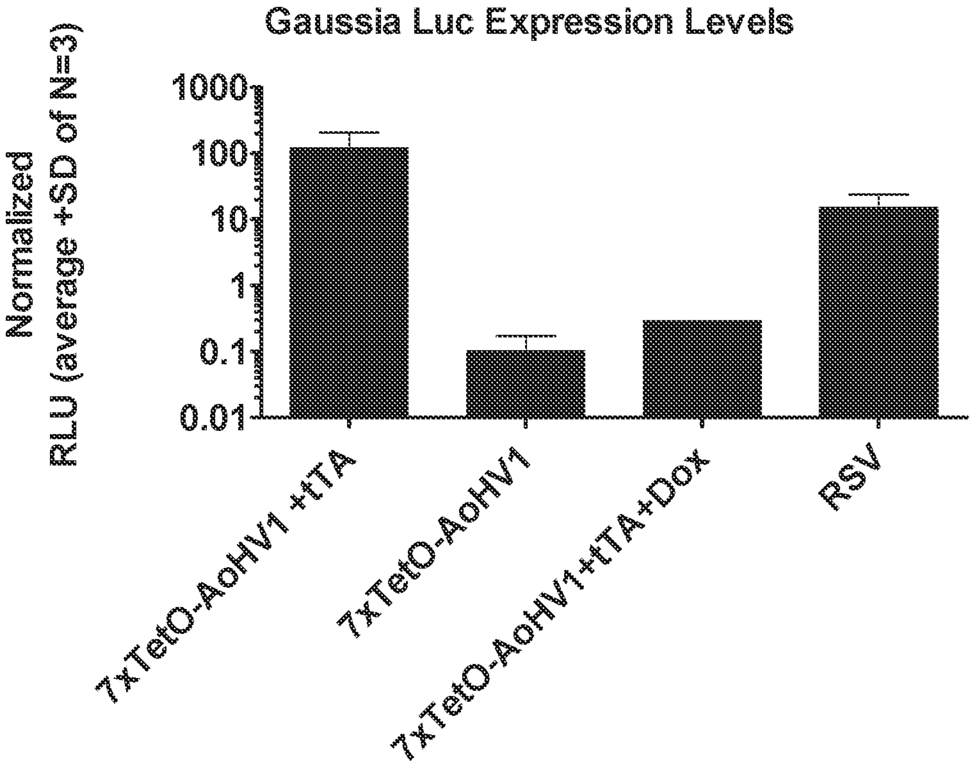
FIG. 3: Testing "7xTetO-AoHV-1" for applicability as a tTA-responsive promoter for regulated expression. Vero cells were transiently transfected with a plasmid in which *Gaussia* luciferase expression is under control of 7xTetO-AoHV-1 (7xTetO placed upstream of the core AoHV-1 promoter), which gives minimal promoter activity. In order to induce promoter activity, a plasmid expressing the tetracyclin transactivator protein (tTA) was co-transfected. Doxycyclin was added to the culture medium of cells co-transfected with the tTA plamid to turn off promoter activity. Rous Sarcoma Virus promoter (RSV) was used as a positive control.

Expression data was normalized for transfection efficiency via measurement of Red Firefly Luciferase (RFL) under control of AoHV-1 short promoter, for which the expression cassette was located on the same pDualLuc plasmid. FIG. 3 depicts the expression of the *Gaussia* luciferase gene under control of the 7xTetO-AoHV-1 promoters. Over four independent experiments (N=4), the basal expression level of the 7xTetO-AoHV-1 promoter was close to background level (cells transfected with medium only, negative control) and on average 1400-fold lower than when co-transfected with a plasmid encoding the transactivator protein tTA (7xTetO-AoHV-1+tTA). Upon addition of Doxycycline (performed twice, N=2), which would inhibit binding of tTA to the tetO sequences of the promoter, the basal levels of expression were again observed. The induced expression level of 7xTetO-AoHV-1 was also compared to the RSV promoter (derived from the LTR of the Rous Sarcoma virus; this being another promoter described for use in biotechnology expression systems), indicating that the induced 7xTetO-AoHV-1 promoter results in ca. 1 log higher *Gaussia* luciferase expression levels than by the RSV promoter.

In conclusion, a putative core promoter-comprising sequence derived from the AoHV-1 promoter can be used to construct an artificial promoter that is responsive to a tetracycline-controlled transactivator protein. Application of this sequence in this context proved to allow for tightly controlled regulation of the expression of a gene of interest. Said sequence therefore represents a true "core promoter" as defined herein as having very low promoter activity on its own, but being able to drive potent gene expression when combined with other regulatory sequences, such as binding sites for natural or artificial transcription factors.

Figure 4A:
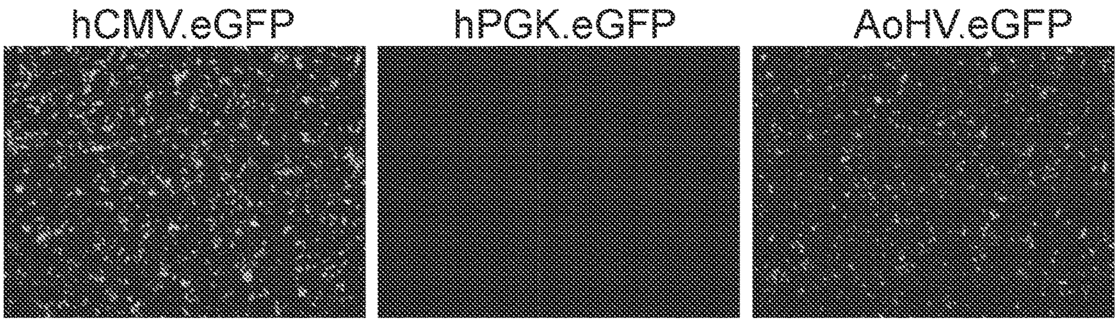
FIGS. 4A, 4B, and 4C: Testing of a TetR-repressible version of AoHV-1 short for regulated expression of a gene of interest (GOI) in cells.

Example 3: Application of the AoHV-1 Promoter in a Small Molecule-Controllable Bacterial Repressor Protein-Based System for Regulated Expression of a Gene of Interest in Mammalian Cells As mentioned in example 2, regulated expression of for instance a toxic gene of interest in a cell line can be essential for recombinant production of proteins or viral vectors. In case a viral vector is used that already contains an expression cassette with an hCMV promoter, it is desirable to use a strong promoter with a different sequence for expression of a gene of interest (GOI) in the production cell line. In order to identify an alternative to the hCMV promoter, AoHV-1 short promoter and the human phosphoglycerate kinase 1 (hPGK) promoter (another promoter described for use in biotechnology expression systems) were tested for transient expression of eGFP in PER.C6 cells. In line with results of example 1, the AoHV-1 short promoter again showed to be a potent promoter for expression of a heterologous gene, driving eGFP expression levels similar to hCMV (of SEQ ID NO:4), and much higher than by the hPGK promoter (SEQ ID NO:6) (FIG. 4A).

Figure 4B:
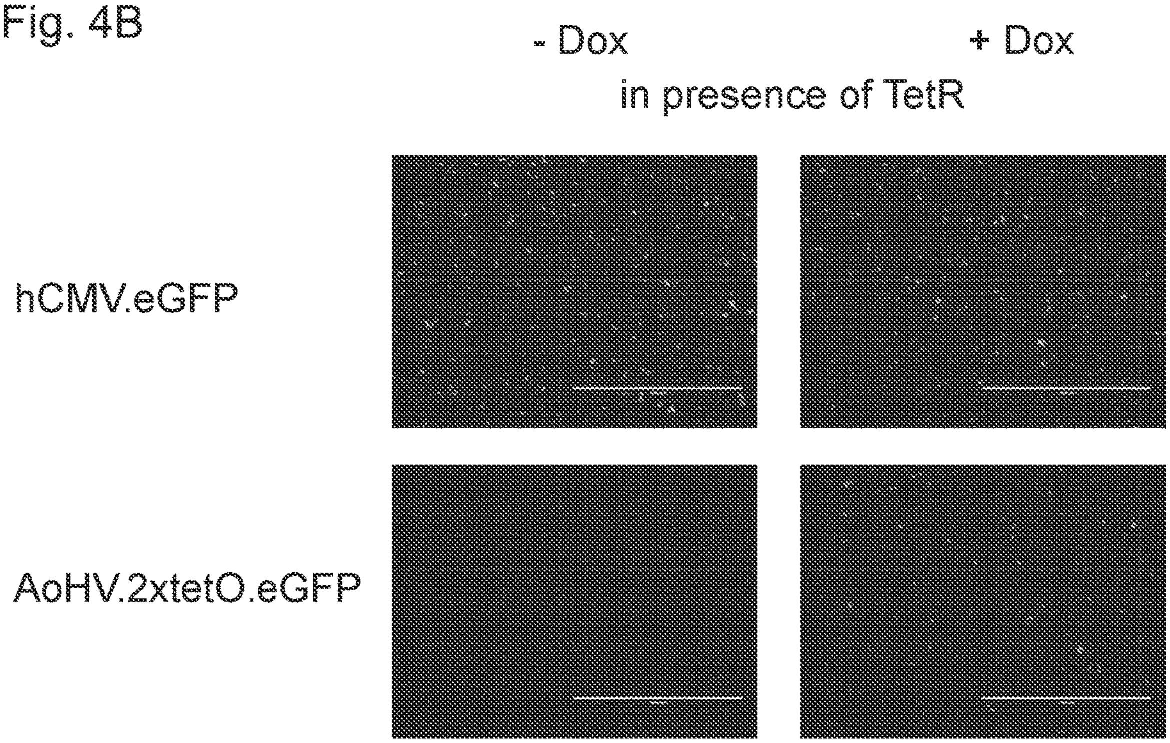

In the following, the AoHV-1 short promoter, which is normally constitutively active (see example 1 and first part of this example), was designed as a tetracycline repressor protein (TetR)-regulated promoter by insertion of two Tet operators downstream of the TATA box and upstream of the transcription start site (TSS) of the AoHV-1 short promoter (AoHV.2xtetO, SEQ ID NO:7). This design was previously shown to work for the hCMV promoter (e.g. see WO 1999/000510 A1). The promoter is active in cells that do not express TetR. In this design, promoter activity is repressed in presence of TetR, e.g. in cell lines expressing TetR. The repression can be alleviated by addition of Doxycyclin (Dox) which has a high affinity for TetR protein. FIG. 4B shows that expression of eGFP cloned downstream of AoHV.2xTetO is indeed repressed in PER.C6-hCMV.TetR cells. Addition of Dox results in increased eGFP protein expression levels, similar to eGFP expression levels driven by hCMV.

Figure 4C:
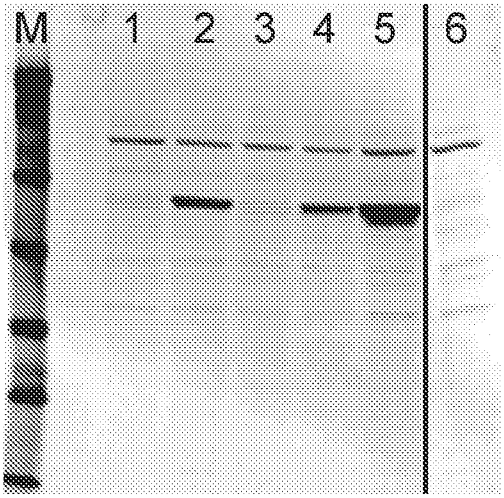

To establish stable cell clones displaying TetR-regulated expression of a gene of interest, PER.C6-hCMV.TetR cells, which express TetR under control of a hCMV promoter, were transfected with a plasmid expressing the gene of interest under control of AoHV.2xtetO. Eighty-five clones were selected using antibiotic selection media. Two clones were selected for testing of inducible expression of the gene of interest (GOI) in this experiment. FIG. 4C shows the testing of the two selected clones for inducible expression of the GOI. As can be seen from the Western Blot, both tested clones show a low background signal in absence of Dox, whereas in presence of Dox, the GOI is potently expressed. As a positive control, cells transiently transfected with a plasmid expressing the GOI under control of the AoHV-1 short promoter was used. The positive control shows higher expression levels of the GOI than the cell clones, which is commonly observed when generating stable cell lines.

An alternative bacterial repressor-regulated promoter in which the cumate operator sequence (CuO) was placed directly downstream of the (putative) initiator element of the AoHV-1 short promoter was also designed and tested, and also proved to be functional (data not shown). In this promoter design, the CymR repressor protein can bind the CuO sequences and thereby inhibit expression.

In addition, analogous to the described TetR- and CymR-regulated AoHV1-promoter-based systems, a Lac operator (LacO)-containing AoHV-1 short promoter was generated and proved to be strongly repressible by the Lac repressor (LacR) (data not shown).

In conclusion, this example confirms the high potency of AoHV-1 short promoter in comparison to other commonly used promoters for heterologous gene expression. Furthermore, TetR-, CymR-, and LacR-regulated versions of the AoHV-1 promoter were generated that allow for regulated expression of GOIs in mammalian cells. This can for instance be used for expression of proteins that are toxic for the cell or for expression of proteins that lead to instability of the cells or vectors.

Figure 5A:
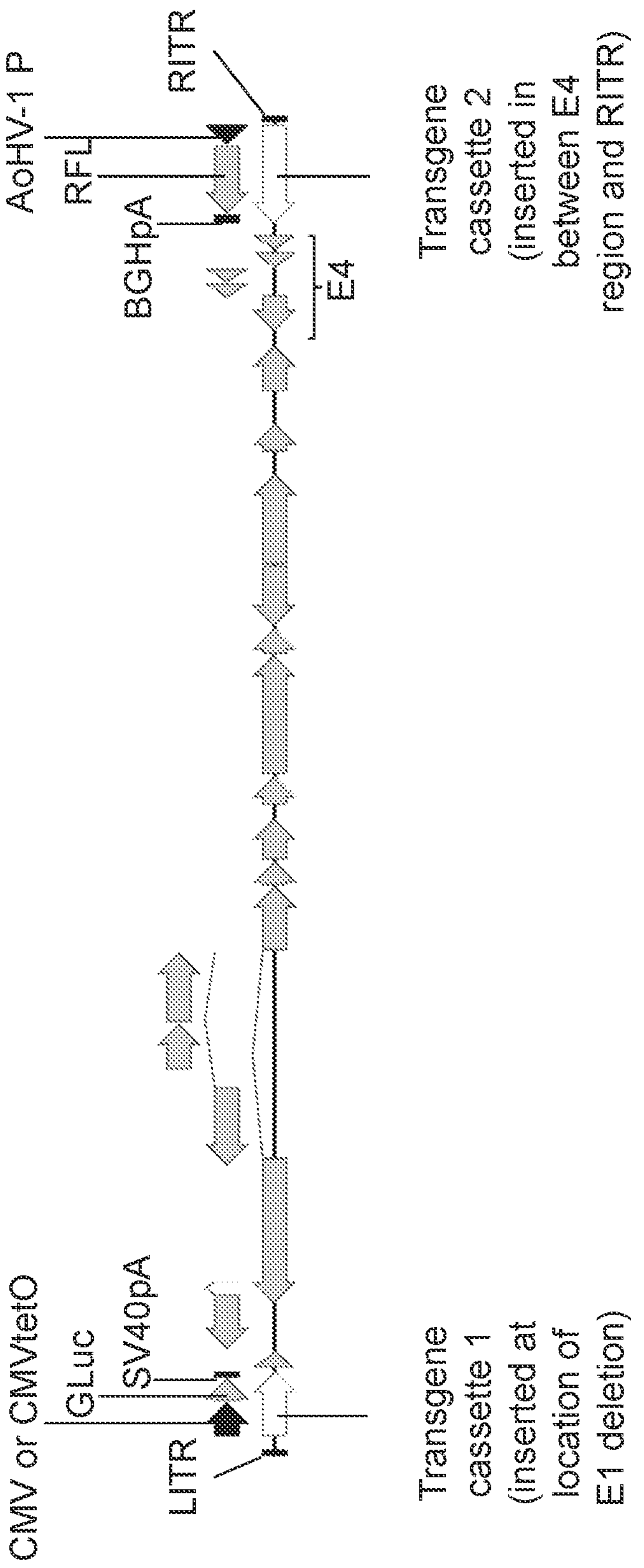
FIGS. 5A, 5B, 5C, and 5D.

Example 4: Application of AoHV-1 Promoter in Viral Vectors with Two Expression Cassettes The AoHV-1 short promoter (AoHV-1 short) can be applied in viral vectors to drive the expression of vaccine antigens or other proteins of interest. This is illustrated herein by the application of AoHV-1 short in the context of adenoviral vectors Ad26.CMV_GLuc.AoHV1_RFL and Ad26.CMVtetO_GLuc.AoHV1_RFL. These are two Ad26-based recombinant adenoviral vectors that both carry two expression cassettes, a first cassette encoding *Gaussia* Luciferase (GLuc) inserted in place of the (deleted) E1 region, and a second cassette encoding red firefly luciferase (RFL) located in between the E4 region and the right inverted terminal repeat (RITR). The Gluc expression cassettes of the two viruses are driven by the hCMV promoter (SEQ ID NO:4) and CMVtetO (SEQ ID NO:15), respectively. CMVtetO differs from the hCMV promoter in that it carries an insertion of a sequence containing two tetracycline operator (TetO) sequence motifs, making that this promoter is repressible by the tetracycline repressor (TetR) protein. In both viruses the RFL expression cassette is under control of AoHV-1 short (SEQ ID NO:30). See FIG. 5A for a schematic representation of the genomes of the two vectors.

The above two vectors were generated by transfection of full-genome plasmids pAd26.CMV_GLuc.AoHV1_RFL and pAd26.CMVtetO_GLuc.AoHV1_RFL, described in the Methods section herein, into PER.C6 cells. These transfections were performed according to standard procedures using Lipofectamine 2000 transfection reagent (Invitrogen) and 4 ug of SwaI-digested plasmid DNA per transfection in a T25 tissue culture flask seeded with $3\times10^6$ PER.C6 cells per flask the day before. (The SwaI digestion serves to release the adenoviral vector genome from the plasmid backbone). After harvesting of the viral rescue transfections, the viruses were further amplified by several successive infection rounds on PER.C6 cells until large-scale virus production infections were performed at viral passage number (VPN) 5 after transfection. The viruses were purified from crude viral harvests using a two-step cesium chloride (CsCl) density gradient ultracentrifugation procedure as described before (Havenga et al., 2006). Viruses were quantified by a spectrophotometry-based procedure to determine the viral particle (VP) titer, and by a TCID50 assay to determine the infectious unit (IU) titer, in both cases as described previously (Maizel, White, & Scharff, 1968).

VP and IU quantification results for the purified batches of Ad26.CMV_GLuc.AoHV1_RFL and Ad26.CMVtetO_GLuc.AoHV1_RFL are shown in Table 1. The viral yields as well as the VP-to-IU ratios obtained for the two batches are in the same range of those that are routinely obtained for standard, single transgene expression cassette-containing Ad26-based vectors. For example, the VP-to-IU ratios obtained for the batches of Ad26.CMV_GLuc.AoHV1_RFL and Ad26.CMVtetO_GLuc.AoHV1_RFL, i.e. 23 and 14, both fall within the range of VP-to-IU ratios of 18, 11, 24, 10, 12, and 26 that were reported previously for a panel of Ad26-based vectors with different (single) transgene expression cassettes (Zahn et al., 2012).

Figure 5B:
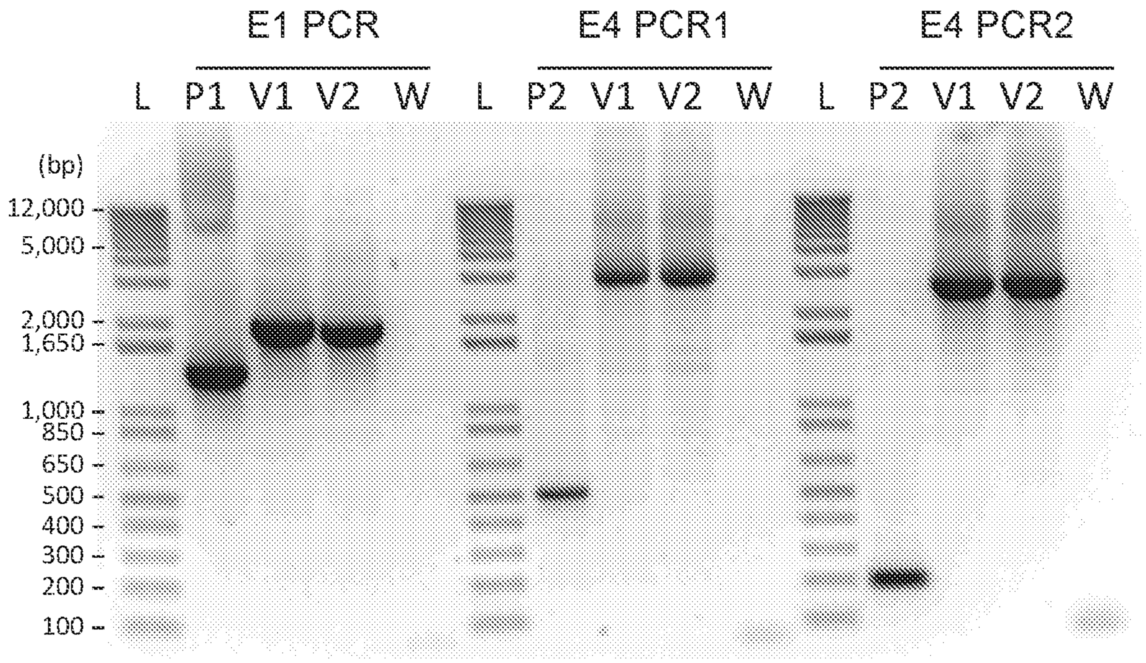

It has been previously reported that use of two identical promoters for expression of two transgenes from the E1 region of an adenovirus can give rise to genetic instability, presumably by homologous recombination (see, e.g. (Belousova et al., 2006) and example 2 of WO2016166088A1). To check whether this can be solved by using a combination of the AoHV-1 promoter of the invention in the same system as the hCMV promoter in the E1 and E4_rITR position respectively, we tested transgene cassette integrity for this combination. Transgene (TG) cassette integrity was confirmed for the two purified batches of Ad26.CMV_GLuc.AoHV1_RFL and Ad26.CMVtetO_GLuc.AoHV1_RFL by PCR-based amplification followed by sequencing of the transgene cassette insertion regions (FIG. 5B). Specifically, a PCR was performed to amplify the TG cassette inserted in E1 ("E1 PCR") and two PCRs were performed targeting the TG cassette in between E4 and the RITR ("E4 PCR1" and "E4 PCR2"). All primers used in these PCRs are complementary to Ad26-specific sequences (i.e. they do not anneal to sequences located within the respective TG cassettes themselves). All PCRs gave products of the expected sizes while no smaller-sized products indicative of deletions could be discerned. Sequencing of the PCR products also did not reveal any mutations. Thus, the combination of the AoHV-1 promoter of the invention and the hCMV promoter in a single vector did yield genetically stable vectors.

Figure 5C:
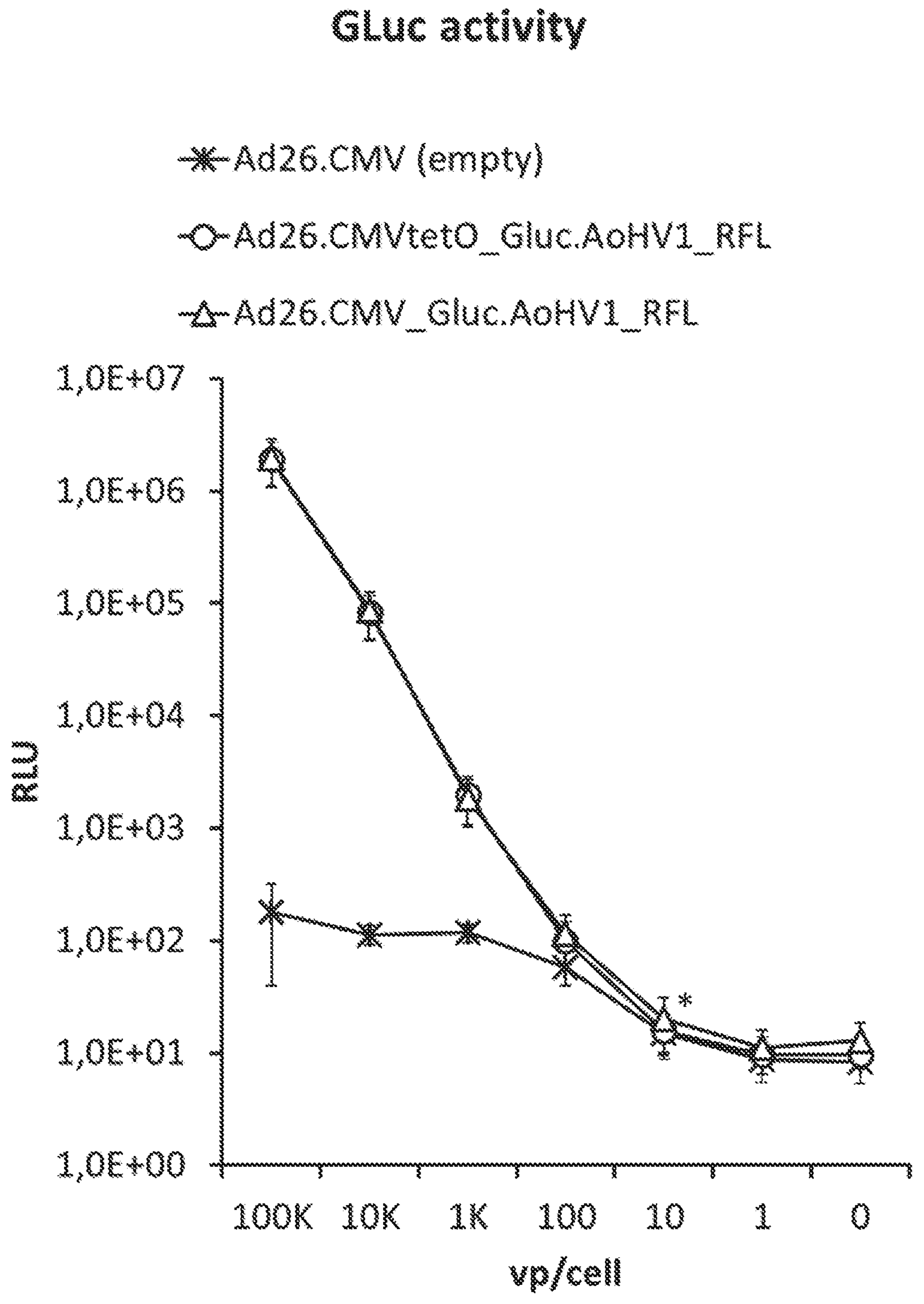
Figure 5D:
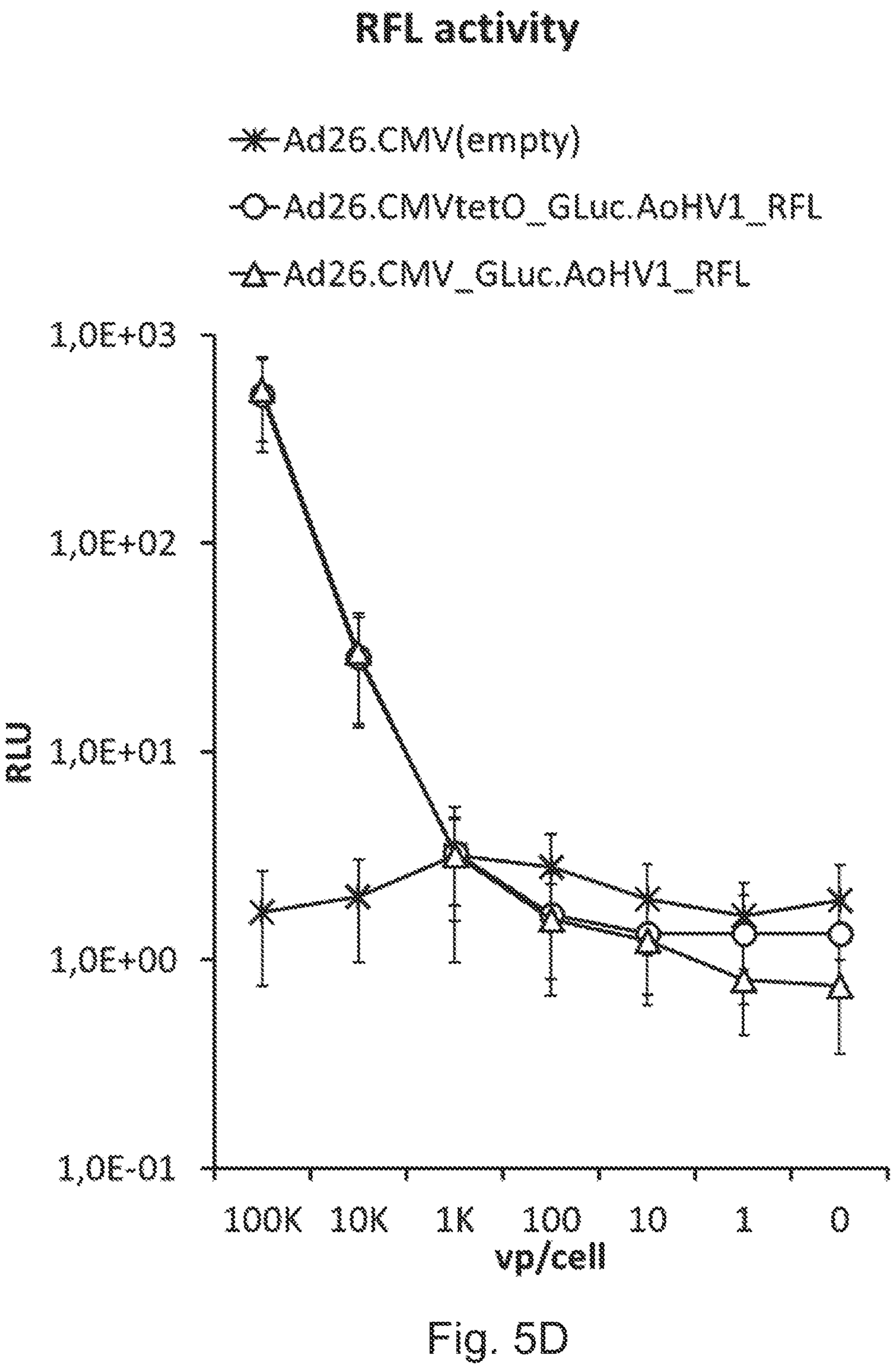

Finally, the Ad26.CMV_GLuc.AoHV1_RFL and Ad26.CMVtetO_GLuc.AoHV1_RFL purified batches were tested for their abilities to express the two luciferases that they encode. To this end, the human cell line A549 was infected at different multiplicities of infections by the two viruses, and GLuc and RFL activities were detected in samples harvested two days later. The results show that both vectors were able to express both GLuc and RFL (FIG. 5C and FIG. 5D). This indicates that the concerning transgene expression cassette configurations are fully functional within the adenoviral genomic contexts in which they were tested.

In conclusion, AoHV-1 short can be applied as a promoter to drive the expression of a protein of interest from transgene expression cassettes inserted in a viral vector. This is exemplified above where AoHV-1 short was employed to express RFL in the context of two adenoviral vectors each comprising two separate transgene expression cassettes inserted at different locations within the adenoviral vector genome. These adenoviral vectors were readily generated and proved producible to high-titer purified vector batches displaying good VP-to-IU ratios and harboring genetically and functionally intact transgene expression cassettes.

Example 5: Application of AoHV-1 Promoter in a Plasmid for Stable Expression of a Gene of Interest in Cells The AoHV-1 promoter can be applied to drive the expression of heterologous genes in stable cell lines. This is illustrated herein by the generation of TetR-expressing cell lines using pC_AoHV_TetR, a plasmid in which TetR gene expression is driven by the AoHV-1 promoter.

pC_AoHV_TetR is depicted in FIG. 6A and is described in the Methods section herein. It comprises a TetR-encoding expression cassette under control of AoHV-1 promoter, and a neomycin phosphotransferase II gene expression cassette under control of an SV40-derived promoter. The latter cassette allows for selection of stably transfected cells by using Geneticin-supplemented cell growth medium.

As further detailed in the Methods section herein under "PER.C6-AoHV.TetR cell line generation procedures", pC_AoHV_TetR was employed for stable transfections into human cell line PER.C6. This resulted, after single cell cloning, in the efficient generation of multiple TetR-expressing "PER.C6-AoHV.TetR" cell clones. It was found that 94 out of the 100 tested Geneticin-resistant clones were positive for TetR expression in a first screening step based on a flow cytometry intracellular staining protocol to detect TetR (data not shown). After a second screening step on 47 of these TetR-positive clones (data not shown), a selection of 24 clones was cryopreserved in small-scale research cell banks.

Figure 6B:
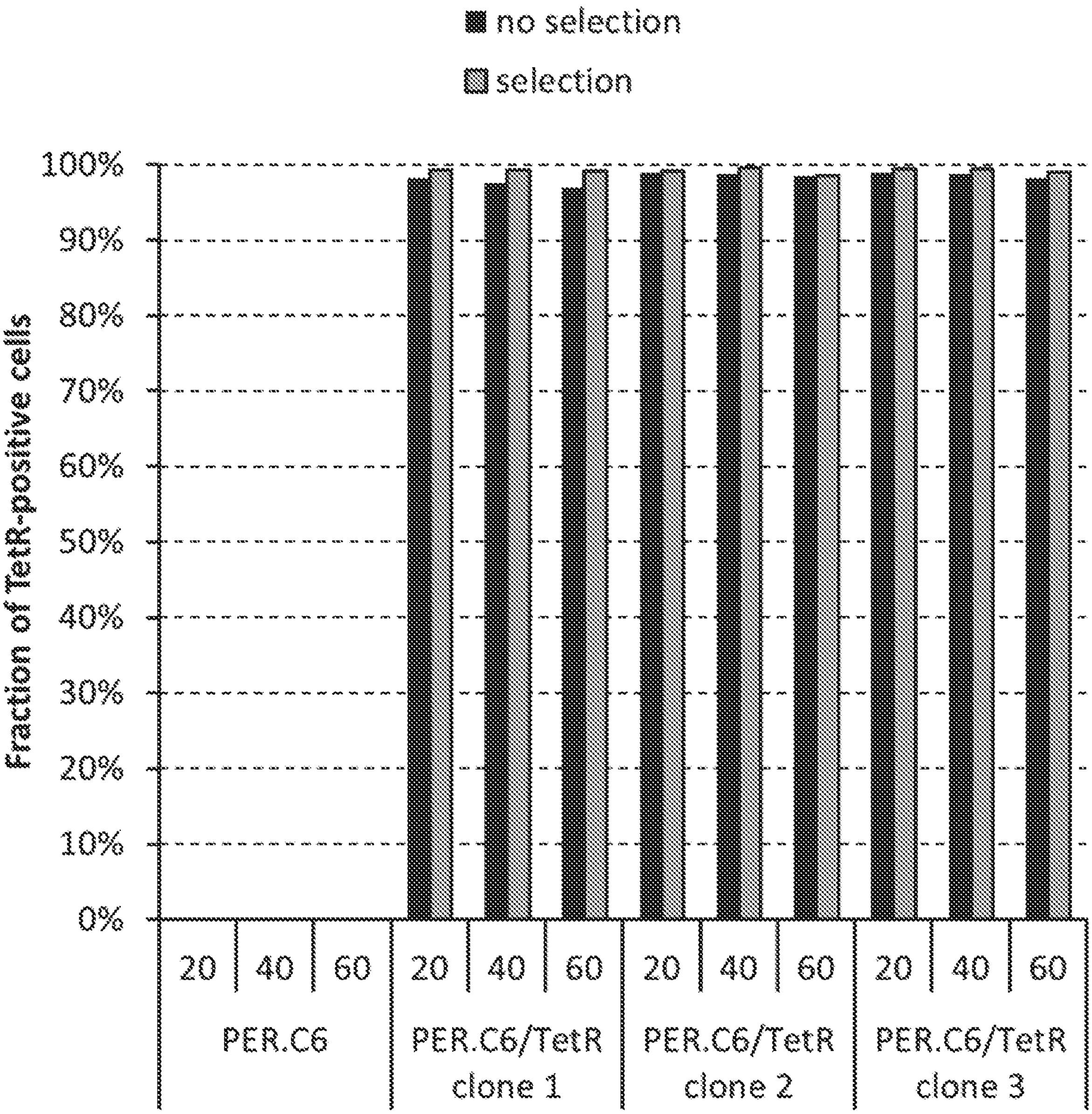
Figure 6C:
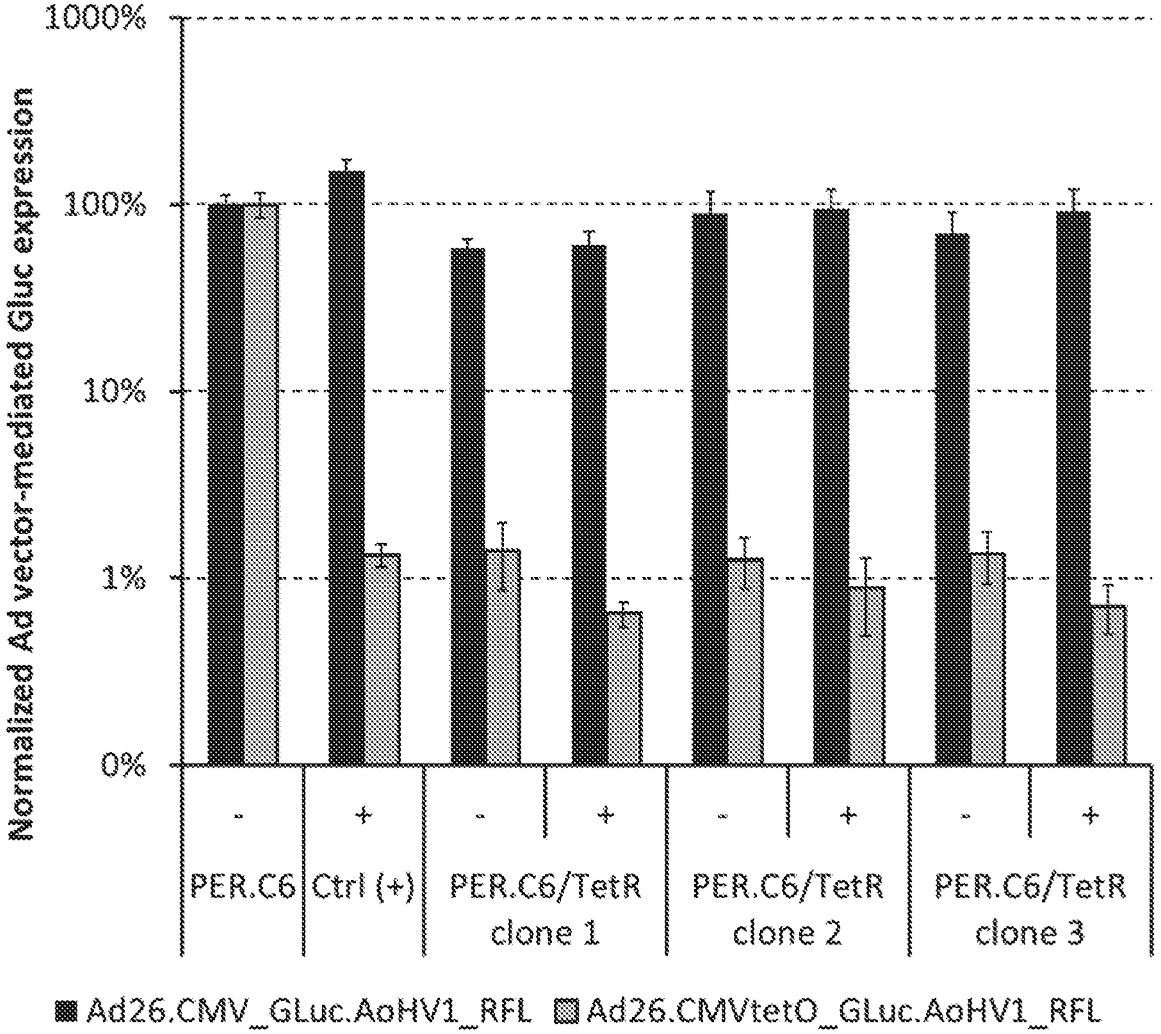

Twelve of the cryopreserved PER.C6-AoHV.TetR clones were subjected to further evaluation of their post-thaw growth performance in shaker flasks and their ability to express (functional) TetR upon extended passaging (up to 60 populations doublings), both in the presence and in the absence of Geneticin selection. It was found that all clones grew at least as efficient, and with similar viabilities, as the parental suspension PER.C6 control cell line (data not shown). Analysis of TetR expression by flow cytometry intracellular staining further demonstrated that the TetR-positive cell fraction remained high (i.e. 97% or higher) throughout the extended passaging experiment. This is shown in FIG. 6B for three representative clones (PER.C6-AoHV.TetR clones 1-3). Finally, a TetR functionality assay demonstrated that the twelve clones all displayed significant TetR-mediated repression activities after their extended passaging, as shown in FIG. 6C for PER.C6-AoHV.TetR clones 1-3. Specifically, at generation 60, all twelve PER.C6-AoHV.TetR clones maintained the ability to repress the expression of an adenoviral vector-encoded reporter gene driven by a TetR-regulated promoter. The levels of repression observed for the 12 different clones were similar to (or higher than) those observed for a positive control cell line (PER.C6-hCMV.TetR) generated using previously described TetR-expressing plasmid pCDNA6/TR, a plasmid comprising a TetR expression cassette controlled by the human CMV promoter.

In conclusion, stable sPER.C6-AoHV.TetR cell lines in which TetR expression is driven by the AoHV1 promoter were successfully generated. This is one, non-limiting, example of the stable expression of a protein of interest after integration of a transgene operably linked to the AoHV-1 promoter according to the invention into the genome of a host cell.

Example 6: Design of Different Versions of the AoHV-1 Promoter

Figure 7A:
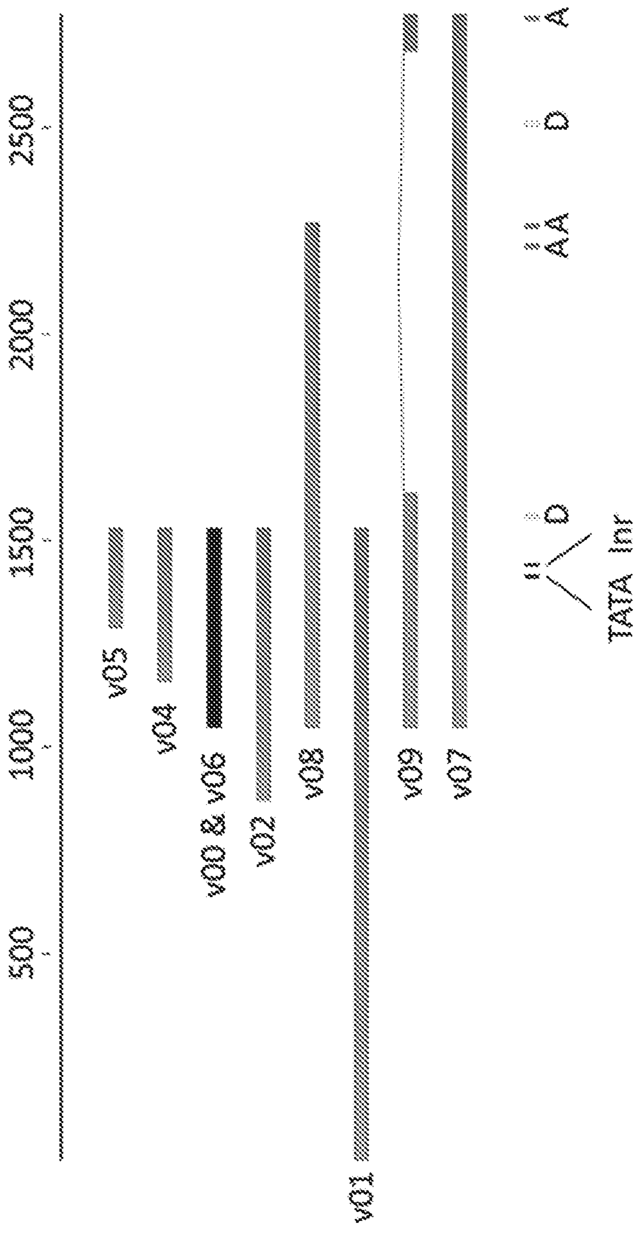
FIGS. 7A and 7B.

In order to map the essential parts of the AoHV-1 major immediate early regulatory region for expression of heterologous genes, a panel of different versions of the AoHV-1 promoter was made. The different designs are presented in FIG. 7A. Two designs were made to truncate the already very short AoHV-1 short sequence in order to map the essential parts of this short promoter sequence. Other designs include additional putative domains and cellular factor binding sites and predicted intron sequences in order to test whether the potency of AoHV-1 short can be increased.

Tested promoter versions are named version v00-v09 and are listed below:

v00: SEQ ID NO:30 (with native AvrII site)
v01: SEQ ID NO:22
v02: SEQ ID NO:23
v03: SEQ ID NO:24
v04: SEQ ID NO:25
v05: SEQ ID NO:26
v06: SEQ ID NO:1 (AvrII site eliminated with single nucleotide insertion of cytosine (c) at nucleotide position 360)
v07: SEQ ID NO:27
v08: SEQ ID NO:28
v09: SEQ ID NO:29

Figure 7B:
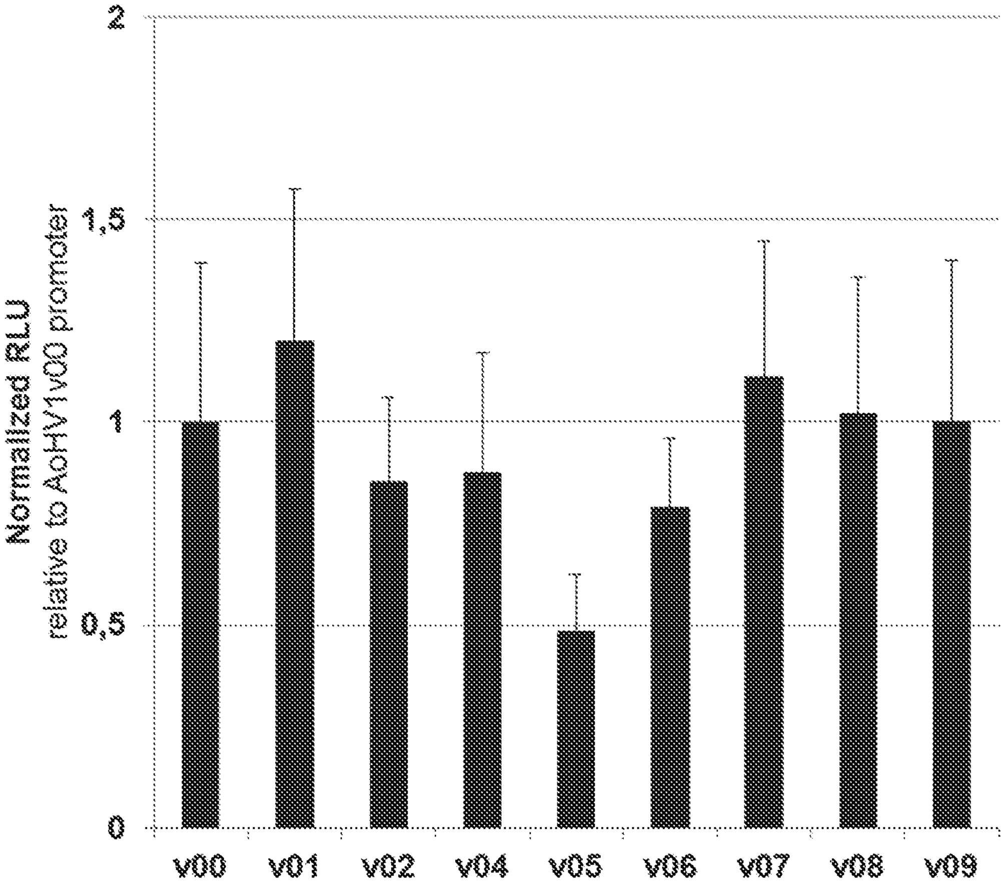

Promoter activity was tested using transient transfection of plasmids into PER.C6 cells. The different promoter versions drive expression of *Gaussia* luciferase in the pDualLuc plasmid described in the methods section herein. FIG. 7B shows the results of promoter potency testing relative to the activity of AoHV-1 short (version 00). The experiment was performed twice. Each individual value was calculated relative to the average of v00 in the same experiment. Values from two experiments were pooled in order to calculate the average and standard deviation, which is displayed relative to AoHV-1 short v00. The activity of v00 and v06 (AoHV-1 short with and without the AvrII site respectively) is considered to be in the same range.

Interestingly, the truncated version 04 shows promoter activity comparable to AoHV-1 short (version 00 and 06). This version 04 has a length of only 371 nucleotides. In contrast, the further truncated version 05 with a length of 241 nucleotides shows reduced activity compared to AoHV-1 short, which may be explained by the absence of several predicted cellular factor binding sites. This promoter version 05 can still be considered a potent promoter. The activity of the promoter is expected to decrease gradually with further truncations.

The potencies of most other promoter versions, which all contain extensions compared to AoHV-1 short promoter, are in the range of AoHV-1 short promoter. Of these extended AoHV-1 promoter variants only v03 (data not shown) shows a major drop in promoter activity compared to AoHV-1 short, but this may be explained by the presence of an incomplete intron sequence in v03: while v03 carries within its extension a predicted splice donor site it lacks any of the predicted splice acceptor sites located further downstream. By contrast, extended AoHV-1 promoter variants v07, v08 and v09, which each do carry at least one predicted splice acceptor site downstream of (any of) their predicted splice donor sites, each showed expression in the range of AoHV-1 short promoter. Sequence v09 is a deletion mutant of v07; compared to v07, v09 carries an internal deletion that leaves intact certain predicted splice donor and acceptor sequences. The data show that v09 is an example of a short but potent AoHV-1 promoter variant harbouring a predicted intron. It can be envisioned that a similarly short but potent, intron-containing promoter can be generated by applying a similar deletion (as said internal deletion applied to v07) to AoHV-1 promoter variant v08.

Two additional AoHV-1 promoter sequences, SEQ ID NO: 33 and SEQ ID NO: 34, were also designed and tested for the ability to drive the expression of a gene of interest. Compared to AoHV-1 short (i.e. SEQ ID NO: 30), these two sequences each carry an 84-bp long 3' truncation and, furthermore, respectively carry 2 and 7 single-nucleotide substitutions within their AoHV-1 promoter core region. Due to said 3' truncation, both SEQ ID NO: 33 and SEQ ID NO: 34 comprise only 1 AoHV-1 nucleotide downstream of the putative initiator sequence of the AoHV-I promoter.

SEQ ID NO: 33 was operably linked to a TetR-encoding sequence by inserting it as part of a synthesized gene fragment into plasmid pC_AoHV_TetR (described in the Methods section herein), replacing the AoHV-1 short promoter of that plasmid. Transient transfections into PER.C6 cells followed by immunoblotting of cell lysates using anti-TetR monoclonal antibody (TetR03, MoBiTec) subsequently demonstrated that promoter activity of SEQ ID NO:33 was similar to that of AoHV-1 short (data not shown).

SEQ ID NO: 34 was operably linked to an RFL-encoding sequence by cloning of a synthesized gene fragment into pDualLuc (described in the Methods section herein) using AvrII and AscI restriction sites. Transient transfection experiments into PER.C6 cells followed by RFL activity measurement in cell lysates subsequently demonstrated that SEQ ID NO:34 is a functional promoter sequence (data not shown).

The activity of these promoter variants demonstrates that for promoter activity, it is not required to include AoHV-1 sequences downstream of the first nucleotide 3' of the putative Inr (i.e., nucleotide 399 in SEQ ID NO: 30, corresponds to nucleotide 287 in SEQ ID NO: 25).

Conclusion

As described supra, a short and potent promoter was identified from Aotine herpesvirus-1. The AoHV-1 promoter has a short sequence and it has potency that is comparable to the hCMV promoter. These features make the AoHV-1 promoter an ideal promoter to use as a substitute in any situation where the hCMV promoter is used. Furthermore, the AoHV-1 promoter has comparatively low sequence identity with the hCMV promoter, which makes it suitable for use in combination with the hCMV promoter when expressing two different transgenes from the same viral vector or when generating viruses with producer cell lines that may also contain similar sequences. The AoHV-1 promoter is also suitable for use with regulatory sequences that can be used to modulate transcription from the AoHV-1 promoter.

TABLE 1

Table showing quantification results for Ad26.CMV_GLuc.AoHV1_RFL and Ad26.CMVtetO_GLuc.AoHV1_RFL purified batches.

| | Viral particle titer (VP/mL) | Infectious unit titer (IU/mL) | VP-to-IU ratio | Total viral yield (VP) * | Relative viral yield (VP/cm$^2$) ** |
|---|---|---|---|---|---|
| Ad26.CMV_GLuc.AoHV1_RFL | 2.2E+12 | 9.8E+10 | 23 | 7.2E+13 | 3.6E+9 |
| Ad26.CMVtetO_GLuc.AoHV1_RFL | 1.4E+12 | 9.8E+10 | 14 | 2.8E+13 | 2.4E9 |

* The Ad26.CMV_GLuc.AoHV1_RFL production was done on 20 PER.C6-seeded T1000 flasks (with surface growth area of 1000 cm$^2$ per flask). The Ad26.CMVtetO_GLuc.AoHV1_RFL production was done on 20 PER.C6-seeded T600 flasks (with surface growth area of 600 cm$^2$ per flask).
** Viral yield relative to the surface growth area

REFERENCES

U.S. Patent Documents:
U.S. Pat. No. 5,057,540A (Oct. 15, 1991). "Saponin adjuvant". Kensil, Charlotte A.; Marciani, Dante J.
U.S. Pat. No. 5,122,458A (Jun. 16, 1992). "Use of a bGH gDNA polyadenylation signal in expression of non-bGH polypeptides in higher eukaryotic cells". Post, Leonard E.; Palermo, Daniel P.; Thomsen, Darrell R.; Rottman, Fritz M.; Goodwin, Edward C.; Woychik, Richard P.
U.S. Pat. No. 5,559,099A (Sep. 24, 1996). "Penton base protein and methods of using same". Wickham, Thomas J.; Kovesdi, Imre; Brough, Douglas E.; McVey, Duncan L.; Brader, Joseph T.
US5837511A (Nov. 17, 1998). "Non-group C adenoviral vectors". Falck Pedersen, Erik S.; Crystal, Ronald G.; Mastrangeli, Andrea; Abrahamson, Karil
U.S. Pat. No. 5,837,520A (Nov. 17, 1998). "Method of purification of viral vectors". Shabram, Paul W.; Huyghe, Bernard G.; Liu, Xiaodong; Shepard, H. Michael
U.S. Pat. No. 5,846,782A (Dec. 8, 1998). "Targeting adenovirus with use of constrained peptide motifs". Wickham, Thomas J.; Roelvink, Petrus W.; Kovesdi, Imre
U.S. Pat. No. 5,851,806A (Dec. 22, 1998). "Complementary adenoviral systems and cell lines". Kovesdi, Imre; Brough, Douglas E.; McVey, Duncan L.; Bruder, Joseph T.; Lizonova, Alena
U.S. Pat. No. 5,891,690A (Apr. 6, 1999). "Adenovirus E1-complementing cell lines". Massie, Bernard
U.S. Pat. No. 5,965,541A (Oct. 12, 1999). "Vectors and methods for gene transfer to cells". Wickham, Thomas J.; Kovesdi, Imre; Brough, Douglas E.
U.S. Pat. No. 5,981,225A (Nov. 9, 1999). "Gene transfer vector, recombinant adenovirus particles containing the same, method for producing the same and method of use of the same". Kochanek, Stefan; Schiedner, Gudrun
U.S. Pat. No. 5,994,106A (Nov. 30, 1999). "Stocks of recombinant, replication-deficient adenovirus free of replication-competent adenovirus". Kovesdi, Imre; Brough, Douglas E.; McVey, Duncan L.; Bruder, Joseph T.; Lizonova, Alena
U.S. Pat. No. 5,994,128A (Nov. 30, 1999). "Packaging systems for human recombinant adenovirus to be used in gene therapy". Fallaux, Frits Jacobus; Hoeben, Robert Cornelis; Van der Eb, Alex Jan; Bout, Abraham; Valerio, Domenico
U.S. Pat. No. 6,020,191A (Feb. 1, 2000). "Adenoviral vectors capable of facilitating increased persistence of transgene expression". Scaria, Abraham; Gregory, Richard J.; Wadsworth, Samuel C.
U.S. Pat. No. 6,040,174A (Mar. 21, 2000). "Defective adenoviruses and corresponding complementation lines". Imler, Jean Luc; Mehtali, Majid; Pavirani, Andrea
U.S. Pat. No. 6,083,716A (Jul. 4, 2000). "Chimpanzee adenovirus vectors". Wilson, James M.; Farina, Steven F.; Fisher, Krishna J.
U.S. Pat. No. 6,113,913A (Sep. 5, 2000). "Recombinant adenovirus". Brough, Douglas E.; Kovesdi, Imre
U.S. Pat. No. 6,225,289B1 (May 1, 2001). "Methods and compositions for preserving adenoviral vectors". Kovesdi, Imre; Ransom, Stephen C.
U.S. Pat. No. 6,261,823B1 (Jul. 17, 2001). "Methods for purifying viruses". Tang, John Chu Tay; Vellekamp, Gary; Bondoc, Jr., Laureano L.
U.S. Pat. No. 6,485,958B2 (Nov. 26, 2002). "Method for producing recombinant adenovirus". Blanche, Francis; Guillaume, Jean Marc
U.S. Pat. No. 7,326,555B2 (Feb. 5, 2008). "Methods of adenovirus purification". Konz, Jr., John O.; Lee, Ann L.; To, Chi Shung Brian; Goerke, Aaron R
U.S. Pat. No. 7,501,129B2 (Mar. 10, 2009). "Vectors comprising guinea pig CMV regulatory elements". Williams, Steven Geraint; Irvine, Alistair Simpson; Gawn, Jonathan
U.S. Pat. No. 8,932,607B2 (Jan. 13, 2015). "Batches of recombinant adenovirus with altered terminal ends". Custers, Jerome H. H. V.; Vellinga, Jort
European Patent Documents:
EP1230354B1 (Jan. 7, 2004). "PERMANENT AMNIOCYTE CELL LINE, THE PRODUCTION THEREOF AND ITS USE FOR PRODUCING GENE TRANSFER VECTORS". KOCHANEK, Stefan; SCHIEDNER, Gudrun
EP1601776B1 (Jul. 2, 2008). "EXPRESSION VECTORS COMPRISING THE MCMV IE2 PROMOTER". CHATELLARD, Philippe; IMHOF, Markus
EP853660B1 (Jan. 22, 2003). "METHOD FOR PRESERVING INFECTIOUS RECOMBINANT VIRUSES, AQUEOUS VIRAL SUSPENSION AND USE AS MEDICINE". SENE, Claude
International Patent Application Publications:
WO1999000510A1 (Jan. 7, 1999). "REGULATION OF TRANSCRIPTION IN MAMMALIAN CELLS AND VIRAL REPLICATION BY A TETRACYCLIN REPRESSOR". Feng Yao WO2003049763A1 (Jun. 19, 2003). "COMPOSITION FOR THE PRESERVATION OF VIRUSES". SETIAWAN, Kerrie; CAMERON, Fiona, Helen
WO2003061708A1 (Jul. 31, 2003). "STABILIZED FORMULATIONS OF ADENOVIRUS". PUNGOR, Erno
WO2003078592A2 (Sep. 25, 2003). "METHOD FOR THE PURIFICATION, PRODUCTION AND FORMULATION OF ONCOLYTIC ADENOVIRUSES". MEMARZADEH, Bahram; PENNATHUR-DAS, Rukmini; WYPYCH, Joseph; YU, De Chao
WO2003104467A1 (Dec. 18, 2003). "MEANS AND METHODS FOR THE PRODUCTION OF ADENOVIRUS VECTORS". VOGELS, Ronald; BOUT, Abraham
WO2004001032A2 (Dec. 31, 2003). "STABLE ADENOVIRAL VECTORS AND METHODS FOR PROPAGATION THEREOF". VOGELS, Ronald; HAVENGA, Menzo, Jans, Emco; ZUIJDGEEST, David, Adrianus, Theodorus
WO2004004762A1 (Jan. 15, 2004). "ISCOM PREPARATION AND USE THEREOF". MOREIN, Bror; LOVGREN BENGTSSON, Karin
WO2004020971A2 (Mar. 11, 2004). "CHROMATOGRAPHIC METHODS FOR ADENOVIRUS PURIFICATION". SENESAC, Joseph
WO2004037294A2 (May 6, 2004). "NEW SETTINGS FOR RECOMBINANT ADENOVIRAL-BASED VACCINES". HAVENGA, Menzo, Jans, Emco; HOLTERMAN, Lennart; KOSTENSE, Stefan; PAU, Maria, Grazia; SPRANGERS, Mieke, Caroline; VOGELS, Ronald
WO2004055187A1 (Jul. 1, 2004). "RECOMBINANT VIRAL-BASED MALARIA VACCINES". PAU, Maria Grazia; HOLTERMAN, Lennart; KASPERS, Jorn; STEGMANN, Antonius, Johannes, Hendrikus
WO2005002620A1 (Jan. 13, 2005). "QUIL A FRACTION WITH LOW TOXICITY AND USE THEREOF". MOREIN, Bror; LOVGREN BENGTSSON, Karin; EKSTROM, Jill; RANLUND, Katarina
WO2005071093A2 (Aug. 4, 2005). "CHIMPANZEE ADENOVIRUS VACCINE CARRIERS". CIRILLO, Agostino; COLLOCA, Stefano; ERCOLE, Bruno, Bruni; MEOLA, Annalisa; NICOSIA, Alfredo; SPORENO, Elisabetta
WO2005080556A2 (Sep. 1, 2005). "VIRUS PURIFICATION METHODS". WEGGEMAN, Miranda; VAN CORVEN, Emile Joannes Josephus Maria
WO2006053871A2 (May 26, 2006). "MULTIVALENT VACCINES COMPRISING RECOMBINANT VIRAL VECTORS". HAVENGA, Menzo, Jans, Emco; VOGELS, Ronald; SADOFF, Jerald; HONE, David; SKEIKY, Yasir Abdul Wahid; RADOSEVIC, Katarina
WO2006108707A1 (Oct. 19, 2006). "VIRUS PURIFICATION USING ULTRAFILTRATION". WEGGEMAN, Miranda
WO2006120034A1 (Nov. 16, 2006). "VACCINE COMPOSITION". ERTL, Peter, Franz; TITE, John, Philip; VAN WELY, Catherine Ann
WO2007073513A2 (Jun. 28, 2007). "METHOD FOR PROPAGATING ADENOVIRAL VECTORS ENCODING INHIBITORY GENE PRODUCTS". GALL, Jason, G., D.; BROUGH, Douglas, E.; RICHTER, King, C.
WO2007100908A2 (Sep. 7, 2007). "CHIMERIC ADENOVIRAL VECTORS". TUCKER, Sean, N.
WO2007104792A2 (Sep. 20, 2007). "RECOMBINANT ADENOVIRUSES BASED ON SEROTYPE 26 AND 48, AND USE THEREOF". BAROUCH, Dan H.; HAVENGA, Menzo Jans Emko
WO2007110409A1 (Oct. 4, 2007). "COMPOSITIONS COMPRISING A RECOMBINANT ADENOVIRUS AND AN ADJUVANT". HAVENGA, Menzo Jans Emko; RADOSEVIC, Katarina
WO2009026183A1 (Feb. 26, 2009). "USE OF CHIMERIC HIV/SIV GAG PROTEINS TO OPTIMIZE VACCINE-INDUCED T CELL RESPONSES AGAINST HIV GAG". NABEL, Gary, J.; YANG, Zhi-Yong; SHI, Wei; BAROUCH, Dan, H.
WO2009117134A2 (Sep. 24, 2009). "AEROSOLIZED GENETIC VACCINES AND METHODS OF USE". ROEDERER, Mario; RAO, Srinivas; NABEL, Gary, J.; ANDREWS, Charla, Anne
WO2010085984A1 (Aug. 5, 2010). "SIMIAN ADENOVIRUS NUCLEIC ACID- AND AMINO ACID-SEQUENCES, VECTORS CONTAINING SAME, AND USES THEREOF". COLLOCA, Stefano; NICOSIA, Alfredo; CORTESE, Riccardo; AMMENDOLA, Virginia; AMBROSIO, Maria
WO2010086189A2 (Aug. 5, 2010). "SIMIAN ADENOVIRUS NUCLEIC ACID- AND AMINO ACID-SEQUENCES, VECTORS CONTAINING SAME, AND USES THEREOF". COLLOCA, Stefano; NICOSIA, Alfredo; CORTESE, Riccardo; AMMENDOLA, Virginia; AMBROSIO, Maria
WO2010096561A1 (Aug. 26, 2010). "SYNTHETIC HIV/SIV GAG PROTEINS AND USES THEREOF". NABEL, Gary J.; YANG, Zhi-yong; SHI, Wei; BAROUCH, Dan H.
WO2011045378A1 (Apr. 21, 2011). "METHOD FOR THE PURIFICATION OF ADENOVIRUS PARTICLES". DE VOCHT, Marcel, Leo; VEENSTRA, Marloes
WO2011045381A1 (Apr. 21, 2011). "PROCESS FOR ADENOVIRUS PURIFICATION FROM HIGH CELL DENSITY CULTURES". DE VOCHT, Marcel, Leo; VEENSTRA, Marloes
WO2013139911A1 (Sep. 26, 2013). "VACCINE AGAINST RSV". RADOSEVIC, Katarina; CUSTERS, Jerôme H. H. V.; VELLINGA, Jort; WIDJOJOATMODJO, Myra N.
WO2013139916A1 (Sep. 26, 2013). "VACCINE AGAINST RSV". RADOSEVIC, Katarina; CUSTERS, Jerôme H. H. V.; VELLINGA, Jort; WIDJOJOATMODJO, Myra, N.
WO 2016166088A1 (Oct. 20, 2016). "RECOMBINANT ADENOVIRUS EXPRESSING TWO TRANSGENES WITH A BIDIRECTIONAL PROMOTER". Kerstin Wunderlich, Jerôme H H V CUSTERS, Jort Vellinga, Barbara Petronella SANDERS.
Other References:
Books
Ausubel et al., Current Protocols in Molecular Biology, Wiley Interscience Publishers, NY (1995)
Ausubel F. M., et al. (editors). Current Protocols in Molecular Biology; the series Methods in Enzymology, Academic Press, Inc. (1987)
Freshney, R. I., Culture of animal cells: A manual of basic technique, fourth edition, Wiley-Liss Inc., ISBN 0-471-34889-9 (2000)
Frokjaer S. and Hovgaard L. (editors), Pharmaceutical Formulation Development of Peptides and Proteins, Taylor & Francis (2000)
Gennaro, A. R. (editor), Remington's Pharmaceutical Sciences, 18th edition, Mack Publishing Company (1990)
Horowitz, M. S., Adenoviruses, Chapter 68, in Virology, (B. N. Fields et al. (editors), 3rd Ed., Raven Press, Ltd., New York (1996)
Kibbe A. (editor), Handbook of Pharmaceutical Excipients, 3rd edition, Pharmaceutical Press (2000)
Kruse and Paterson (editors), Tissue Culture, Academic Press. (1973)
MacPherson M. J., Hams B. D., Taylor G. R. (editors), PCR2: A Practical Approach (1995)
Sambrook et al., Molecular Cloning, a Laboratory Manual, 2nd Ed., Cold Spring Harbor Press, Cold Spring Harbor, N.Y. (1989)
Sambrook, Fritsch and Maniatis, Molecular Cloning: A Laboratory Manual, 2nd Ed., (1989)

Shenk, Thomas, Adenoviridae and their Replication, Chapter 67, in Virology, B. N. Fields et al. (editors), 3rd Ed., Raven Press, Ltd., New York (1996)

Watson et al., Recombinant DNA, 2nd ed., Scientific American Books. (1992)

Journals

Abbink, P., Lemckert, A. A., Ewald, B. A., Lynch, D. M., Denholtz, M., Smits, S., . . . Barouch, D. H. (2007). Comparative seroprevalence and immunogenicity of six rare serotype recombinant adenovirus vaccine vectors from subgroups B and D. *J Virol,* 81(9), 4654-4663. doi: 10.1128/JVI.02696-06

Altschul, S. F., Gish, W., Miller, W., Myers, E. W., & Lipman, D. J. (1990). Basic local alignment search tool. *J Mol Biol,* 215(3), 403-410. doi: 10.1016/50022-2836(05)80360-2

Barry, P. A., Alcendor, D. J., Power, M. D., Kerr, H., & Luciw, P. A. (1996). Nucleotide sequence and molecular analysis of the rhesus cytomegalovirus immediate-early gene and the UL121-117 open reading frames. *Virology,* 215(1), 61-72. doi: 10.1006/viro.1996.0007

Belousova, N., Harris, R., Zinn, K., Rhodes-Selser, M. A., Kotov, A., Kotova, O., . . . Alvarez, R. D. (2006). Circumventing recombination events encountered with production of a clinical-grade adenoviral vector with a double-expression cassette. *Mol Pharmacol,* 70(5), 1488-1493.

Chan, Y. J., Chiou, C. J., Huang, Q., & Hayward, G. S. (1996). Synergistic interactions between overlapping binding sites for the serum response factor and ELK-1 proteins mediate both basal enhancement and phorbol ester responsiveness of primate cytomegalovirus major immediate-early promoters in monocyte and T-lymphocyte cell types. *J Virol,* 70(12), 8590-8605.

Chang, Y. N., Jeang, K. T., Chiou, C. J., Chan, Y. J., Pizzorno, M., & Hayward, G. S. (1993). Identification of a large bent DNA domain and binding sites for serum response factor adjacent to the NFI repeat cluster and enhancer region in the major IE94 promoter from simian cytomegalovirus. *J Virol,* 67(1), 516-529.

Foecking, M. K., & Hofstetter, H. (1986). Powerful and versatile enhancer-promoter unit for mammalian expression vectors. *Gene,* 45(1), 101-105.

Gao, G. P., Engdahl, R. K., & Wilson, J. M. (2000). A cell line for high-yield production of E1-deleted adenovirus vectors without the emergence of replication-competent virus. *Hum Gene Ther,* 11(1), 213-219. doi: 10.1089/10430340050016283

Gibson, D. G., Young, L., Chuang, R. Y., Venter, J. C., Hutchison, C. A., 3rd, & Smith, H. O. (2009). Enzymatic assembly of DNA molecules up to several hundred kilobases. *Nat Methods,* 6(5), 343-345. doi: 10.1038/nmeth.1318

Gossen, M., & Bujard, H. (1992). Tight control of gene expression in mammalian cells by tetracycline-responsive promoters. *Proc Natl Acad Sci USA,* 89(12), 5547-5551.

Gossen, M., Freundlieb, S., Bender, G., Muller, G., Hillen, W., & Bujard, H. (1995). Transcriptional activation by tetracyclines in mammalian cells. *Science,* 268(5218), 1766-1769.

Hansen, S. G., Strelow, L. I., Franchi, D. C., Anders, D. G., & Wong, S. W. (2003). Complete sequence and genomic analysis of rhesus cytomegalovirus. *J Virol,* 77(12), 6620-6636.

Havenga, M., Vogels, R., Zuijdgeest, D., Radosevic, K., Mueller, S., Sieuwerts, M., . . . Goudsmit, J. (2006). Novel replication-incompetent adenoviral B-group vectors: high vector stability and yield in PER.C6 cells. *J Gen Virol,* 87(Pt 8), 2135-2143. doi: 10.1099/vir.0.81956-0

Heilbronn, R., & Weger, S. (2010). Viral vectors for gene transfer: current status of gene therapeutics. *Handb Exp Pharmacol*(197), 143-170. doi: 10.1007/978-3-642-00477-3_5

Hoganson, D. K., Ma, J. C., Asato, L., Ong, M., Printz, M. A., Huyghe, B. G., . . . D'Andrea, M. J. (2002). Development of a Stable Adenoviral Vector Formulation. *BioProcessing J.,* 1(1), 43-48.

Holterman, L., Vogels, R., van der Vlugt, R., Sieuwerts, M., Grimbergen, J., Kaspers, J., . . . Havenga, M. (2004). Novel replication-incompetent vector derived from adenovirus type 11 (Ad11) for vaccination and gene therapy: low seroprevalence and non-cross-reactivity with Ad5. *J Virol,* 78(23), 13207-13215. doi: 10.1128/JVI.78.23.13207-13215.2004

Lemckert, A. A., Grimbergen, J., Smits, S., Hartkoorn, E., Holterman, L., Berkhout, B., . . . Havenga, M. J. (2006). *Generation of a novel replication-incompetent adenoviral vector derived from human adenovirus type* 49: manufacture on PER.C6 cells, tropism and immunogenicity. *J Gen Virol,* 87(Pt 10), 2891-2899. doi: 10.1099/vir.0.82079-0

Maizel, J. V., Jr., White, D. O., & Scharff, M. D. (1968). The polypeptides of adenovirus. I. Evidence for multiple protein components in the virion and a comparison of types 2, 7A, and 12. *Virology,* 36(1), 115-125.

Mullick, A., Xu, Y., Warren, R., Koutroumanis, M., Guilbault, C., Broussau, S., . . . Massie, B. (2006). The cumate gene-switch: a system for regulated expression in mammalian cells. *BMC Biotechnol,* 6, 43. doi: 10.1186/1472-6750-6-43

Ogun, S. A., Dumon-Seignovert, L., Marchand, J. B., Holder, A. A., & Hill, F. (2008). The oligomerization domain of C4-binding protein (C4 bp) acts as an adjuvant, and the fusion protein comprised of the 19-kilodalton merozoite surface protein 1 fused with the murine C4 bp domain protects mice against malaria. *Infect Immun,* 76(8), 3817-3823. doi: 10.1128/IAI.01369-07

Powell, S. K., Rivera-Soto, R., & Gray, S. J. (2015). Viral expression cassette elements to enhance transgene target specificity and expression in gene therapy. *Discov Med,* 19(102), 49-57.

Robbins, P. D., & Ghivizzani, S. C. (1998). Viral vectors for gene therapy. *Pharmacol Ther,* 80(1), 35-47.

Rubnitz, J., & Subramani, S. (1984). The minimum amount of homology required for homologous recombination in mammalian cells. *Mol Cell Biol,* 4(11), 2253-2258.

Schlabach, M. R., Hu, J. K., Li, M., & Elledge, S. J. (2010). Synthetic design of strong promoters. *Proc Natl Acad Sci USA,* 107(6), 2538-2543. doi: 10.1073/pnas.0914803107

Smale, S. T. (2001). Core promoters: active contributors to combinatorial gene regulation. *Genes Dev,* 15(19), 2503-2508. doi: 10.1101/gad.937701

Vogels, R., Zuijdgeest, D., van Rijnsoever, R., Hartkoorn, E., Damen, I., de Bethune, M. P., . . . Havenga, M. (2003). Replication-deficient human adenovirus type 35 vectors for gene transfer and vaccination: efficient human cell infection and bypass of preexisting adenovirus immunity. *J Virol,* 77(15), 8263-8271.

Walther, W., & Stein, U. (2000). Viral vectors for gene transfer: a review of their use in the treatment of human diseases. *Drugs,* 60(2), 249-271.

Zahn, R., Gillisen, G., Roos, A., Koning, M., van der Helm, E., Spek, D., . . . Rodriguez, A. (2012). Ad35 and ad26 vaccine vectors induce potent and cross-reactive antibody and T-cell responses to multiple filovirus species. *PLoS One,* 7(12), e44115. doi: 10.1371/journal.pone.0044115

The invention claimed is:

1. A method for preparing an adenovirus, the method comprising propagating in a cell an adenovirus that encodes a transgene under control of a hCMV promoter that is operably linked to one or more tetO sites, wherein the cell comprises in its genome a nucleic acid molecule comprising an AoHV-1 promoter operably linked to a nucleic acid encoding tetracycline repressor (TetR) protein, and wherein the AoHV-1 promoter comprises a sequence having at least 95% identity to nucleotides 131 to 286 of SEQ ID NO:25.

2. The method of claim 1, wherein the AoHV-1 promoter comprises a sequence having at least 98% identity to nucleotides 131 to 286 of SEQ ID NO: 25.

3. The method of claim 1, wherein the adenovirus has at least one deletion in its genome.

4. The method of claim 1, further comprising isolating the adenovirus.

5. The method of claim 4, further comprising formulating the adenovirus into a pharmaceutically acceptable composition.

6. The method of claim 1, wherein the AoHV-1 promoter comprises a sequence having at least 95% identity to any one of SEQ ID NOs: 1, 26, 30, 22, 23, 27, 28, 29, 33, or 34.

7. The method of claim 6, wherein the AoHV-1 promoter comprises a sequence having at least 95% identity to SEQ ID NO: 26.

8. A method for producing a virus, comprising propagating the virus in a cell that expresses a heterologous gene that has a function in propagating said virus, wherein said heterologous gene is under control of an AoHV-1 promoter, wherein the AoHV-1 promoter comprises a sequence having at least 95% identity to nt 131-286 of SEQ ID NO: 25, and harvesting the virus from said cell or from a culture medium wherein said cell is cultured, or from both the cell and the culture medium.

9. The method of claim 8, wherein the AoHV-1 promoter comprises a sequence having at least 98% identity to nucleotides 131 to 286 of SEQ ID NO: 25.

10. A nucleic acid molecule comprising an Aotine Herpesvirus 1 major immediate early promoter (AoHV-1 promoter) operably linked to a heterologous transgene, wherein the AoHV-1 promoter comprises a sequence having at least 95% identity to nucleotides 131 to 286 of SEQ ID NO:25, and wherein the AoHV-1 promoter comprises a sequence having at least 95% identity to any one of SEQ ID NOs: 1, 26, 30, 22, 23, 27, 28, 29, 33, or 34.

11. A vector or a virus, comprising a nucleic acid molecule according to claim 10.

12. The vector according to claim 11, wherein the vector is a plasmid vector.

13. The virus according to claim 11, wherein the virus is an adenovirus.

14. The adenovirus according to claim 13, wherein the adenovirus has at least one deletion in its genome.

15. An isolated host cell comprising a nucleic acid molecule according to claim 10.

* * * * *

SEQUENCE LISTING

<160> NUMBER OF SEQ ID NOS: 37

<210> SEQ ID NO 1
<211> LENGTH: 484
<212> TYPE: DNA
<213> ORGANISM: Artificial Sequence
<220> FEATURE:
<223> OTHER INFORMATION: AoHV-1 short (AvrII site eliminated with single nucleotide insertion of cytosine (c) at nucleotide position 360)

<400> SEQUENCE: 1

```
aaatcaatga cttggcaagc atatacatcc gtcctggcac cagaataggg gttaaatggg     60
gactttccat aagcccaccg cctcatttgg caccaaaaag gggatttct attattagtc     120
aatgtccttg gccaatagcc agtgacgtca atgggaacgg ggccagttcc cctttcccac    180
cattaccggc aatggtgggt ggggaaattc catattagtc aatgttcttg gcaccaaaac    240
cgcggggact ttccattgac gtcagtggaa aggggcgtaa cggggagtga ccatgggcgt    300
tcccgggcgg agttatgggc gttactgggc ggttcgtggg cggaccatgg gctgtcctac    360
gggtatataa gcagagcccg gttagcagac cgccattcgc cttcaagaca gcgtgaggga    420
cccacgttct ccggaccagc caccgggacc gagcggccta gcctagccgg ggacccttca    480
ctgg                                                                  484
```

<210> SEQ ID NO 2
<211> LENGTH: 1333
<212> TYPE: DNA
<213> ORGANISM: Artificial Sequence
<220> FEATURE:
<223> OTHER INFORMATION: AoHV-1 long

<400> SEQUENCE: 2

```
cctaggtcaa tatactggat gtcagccagc taaaaaaata aacaataaaa tcgtcacctg     60
gcattcagcc aatggatcaa tgtattggct gaatgccata ctattgatat atagataatc    120
tattgccaat taattggcca tatagccaat acaatggcac ggggccaatg tattggctat    180
atatcaatat gatggcgggg ttccagtata ttaatatatt gccaatgtat tggctatata    240
tcaatatggt ggcaaggttc cagtatatta atctattggc aatctattgg ccatatatca    300
atatggtggc aaggttccag tatattaatc tattggcaat ctattggcca tatatcaata    360
tggtggcaag gttccagtat attaatctat tggcaatcta ttggccatat atcaatatgg    420
tggcaaggtt ccagtatatt aatctattgg caatctattg gccatatatc aatatggtgg    480
cagtgaccca agttattaat ctattgccaa tataggccaa tagattggag atgagccagt    540
ctatcaatcc ataatcaata tatatctatc agtattggga catatattga ttagtatggg    600
gtcaaatagg gtatttccgt gttcccatca atacttggca caaacaacac tatgactcaa    660
tgggctatgg gccaagaaca taggtcaaat agggtatttc cgtgttccca tctgtacttg    720
gcacaaacaa cactatgact caataggcta tttgccaaga acataaggtc aatcagggta    780
cttccgcgtt cccaccgccc catttggcaa caaaataggg gttatttggg ggtcttcccc    840
ttgaaatcaa tgacttggca agcatataca tccgtcctgg caccagaata ggggttaaat    900
ggggactttc cataagccca ccgcctcatt tggcaccaaa aaggggggatt tctattatta   960
gtcaatgtcc ttggccaata gccagtgacg tcaatgggaa cggggccagt tcccctttcc   1020
caccattacc ggcaatggtg ggtggggaaa ttccatatta gtcaatgttc ttggcaccaa   1080
aaccgcgggg actttccatt gacgtcagtg gaaaggggcg taacggggag tgaccatggg   1140
```

cgttcccggg cggagttatg ggcgttactg ggcggttcgt gggcggacca tgggctgtcc 1200
tacgggtata taagcagagc ccggttagca gaccgccatt cgccttcaag acagcgtgag 1260
ggacccacgt tctccggacc agccaccggg accgagcggc ctagcctagc cggggaccct 1320
tcactggaag ctt 1333

<210> SEQ ID NO 3
<211> LENGTH: 397
<212> TYPE: DNA
<213> ORGANISM: Artificial Sequence
<220> FEATURE:
<223> OTHER INFORMATION: chCMV short

<400> SEQUENCE: 3
cgccaattgc atcatcctat tgtttttcta tgggaatttc cctattggca gtacatcaac 60
gtattactaa tggggatttc caatgactaa tacaacgggc agtacgccca gtacgtatga 120
ctaatgggac tttccataat cccgccccat tgacgtcaat gggcatccgt tctggcacca 180
aaatgaatgg gaatttccaa tatgagtcat aaaccccgcc ccattgacgc acattacacg 240
tcaatgggcg gtaggcgtgc cctatgggcg gtctatataa gcagagcccg tttagtgaac 300
cgtcacttcg cttggagcca ccgtccacgc tgtttggagc tccatagaag gaaccgggac 360
ccagccagcc tccgtagccg ggaacggtgc attggaa 397

<210> SEQ ID NO 4
<211> LENGTH: 829
<212> TYPE: DNA
<213> ORGANISM: Artificial Sequence
<220> FEATURE:
<223> OTHER INFORMATION: hCMV

<400> SEQUENCE: 4
tcaatattgg ccattagcca tattattcat tggttatata gcataaatca atattggcta 60
ttggccattg catacgttgt atccatatca taatatgtac atttatattg gctcatgtcc 120
aacattaccg ccatgttgac attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtacg ccccctattg acgtcaatga 420
cggtaaatgg cccgcctggc attatgccca gtacatgacc ttatgggact ttcctacttg 480
gcagtacatc tacgtattag tcatcgctat taccatggtg atgcggtttt ggcagtacat 540
caatgggcgt ggatagcggt ttgactcacg gggatttcca agtctccacc ccattgacgt 600
caatgggagt ttgttttggc accaaaatca acgggacttt ccaaaatgtc gtaacaactc 660
cgccccattg acgcaaatgg gcggtaggcg tgtacggtgg gaggtctata taagcagagc 720
tcgtttagtg aaccgtcaga tcgcctggag acgccatcca cgctgttttg acctccatag 780
aagacaccgg gaccgatcca gcctccgcgg ccgggaacgg tgcattgga 829

<210> SEQ ID NO 5
<211> LENGTH: 315
<212> TYPE: DNA
<213> ORGANISM: Artificial Sequence
<220> FEATURE:
<223> OTHER INFORMATION: 7xTetO-AoHV-1

<400> SEQUENCE: 5

-continued

```
ttactcccta tcagtgatag agaacgtatg tcgagtttac tccctatcag tgatagagaa      60

cgatgtcgag tttactccct atcagtgata gagaacgtat gtcgagttta ctccctatca     120

gtgatagaga acgtatgtcg agtttactcc ctatcagtga tagagaacgt atgtcgagtt     180

tatccctatc agtgatagag aacgtatgtc gagtttactc cctatcagtg atagagaacg     240

tatgtcgagg cggaccatgg gctgtcctag ggtatataag cagagcccgg ttagcagacc     300

gccattcgcc ttcaa                                                      315


<210> SEQ ID NO 6
<211> LENGTH: 505
<212> TYPE: DNA
<213> ORGANISM: Artificial Sequence
<220> FEATURE:
<223> OTHER INFORMATION: hPGK

<400> SEQUENCE: 6

aattgcgata attccacggg gttggggttg cgccttttcc aaggcagccc tgggtttgcg      60

cagggacgcg gctgctctgg gcgtggttcc gggaaacgca gcggcgccga ccctgggtct     120

cgcacattct tcacgtccgt tcgcagcgtc acccggatct tcgccgctac ccttgtgggc     180

cccccggcga cgcttcctgc tccgccccta agtcgggaag gttccttgcg gttcgcggcg     240

tgccggacgt gacaaacgga agccgcacgt ctcactagta ccctcgcaga cggacagcgc     300

cagggagcaa tggcagcgcg ccgaccgcga tgggctgtgg ccaatagcgg ctgctcagca     360

gggcgcgccg agagcagcgg ccgggaaggg gcggtgcggg aggcggggtg tggggcggta     420

gtgtgggccc tgttcctgcc cgcgcggtgt tccgcattct gcaagcctcc ggagcgcacg     480

tcggcagtcg gctccctcgt tccga                                           505


<210> SEQ ID NO 7
<211> LENGTH: 538
<212> TYPE: DNA
<213> ORGANISM: Artificial Sequence
<220> FEATURE:
<223> OTHER INFORMATION: AoHV.2xtetO

<400> SEQUENCE: 7

aaatcaatga cttggcaagc atatacatcc gtcctggcac cagaataggg gttaaatggg      60

gactttccat aagcccaccg cctcatttgg caccaaaaag gggatttct attattagtc     120

aatgtccttg gccaatagcc agtgacgtca atgggaacgg ggccagttcc cctttcccac     180

cattaccggc aatggtgggt ggggaaattc catattagtc aatgttcttg gcaccaaaac     240

cgcggggact ttccattgac gtcagtggaa aggggcgtaa cggggagtga ccatgggcgt     300

tcccgggcgg agttatgggc gttactgggc ggttcgtggg cggaccatgg gctgtcctag     360

ggtatataag cagagccctc cctatcagtg atagagatct ccctatcagt gatagagatc     420

gtcgacgagc tcggttagca gaccgccatt cgccttcaag acagcgtgag ggacccacgt     480

tctccggacc agccaccggg accgagcggc ctagcctagc cggggaccct tcactggg       538


<210> SEQ ID NO 8
<211> LENGTH: 20
<212> TYPE: DNA
<213> ORGANISM: Artificial Sequence
<220> FEATURE:
<223> OTHER INFORMATION: E1 PCR - forward

<400> SEQUENCE: 8
```

-continued tggcgcgaaa actgaatgag 20

<210> SEQ ID NO 9
<211> LENGTH: 21
<212> TYPE: DNA
<213> ORGANISM: Artificial Sequence
<220> FEATURE:
<223> OTHER INFORMATION: E1 PCR - reverse

<400> SEQUENCE: 9
gcaggcgggt tgtcaaataa g 21

<210> SEQ ID NO 10
<211> LENGTH: 20
<212> TYPE: DNA
<213> ORGANISM: Artificial Sequence
<220> FEATURE:
<223> OTHER INFORMATION: E4 PCR1 - forward

<400> SEQUENCE: 10
gacgggagca atccctccag 20

<210> SEQ ID NO 11
<211> LENGTH: 20
<212> TYPE: DNA
<213> ORGANISM: Artificial Sequence
<220> FEATURE:
<223> OTHER INFORMATION: E4 PCR1 - reverse

<400> SEQUENCE: 11
ccccacaaag taaacaaaag 20

<210> SEQ ID NO 12
<211> LENGTH: 20
<212> TYPE: DNA
<213> ORGANISM: Artificial Sequence
<220> FEATURE:
<223> OTHER INFORMATION: E4 PCR2 - forward

<400> SEQUENCE: 12
cgttctcact tcctcgtatc 20

<210> SEQ ID NO 13
<211> LENGTH: 18
<212> TYPE: DNA
<213> ORGANISM: Artificial Sequence
<220> FEATURE:
<223> OTHER INFORMATION: E4 PCR2 - reverse

<400> SEQUENCE: 13
caacgctgat tggacgag 18

<210> SEQ ID NO 14
<211> LENGTH: 17
<212> TYPE: DNA
<213> ORGANISM: Artificial Sequence
<220> FEATURE:
<223> OTHER INFORMATION: tetO regulatory sequence

<400> SEQUENCE: 14
ccctatcagt gatagag 17

<210> SEQ ID NO 15
<211> LENGTH: 883
<212> TYPE: DNA
<213> ORGANISM: Artificial Sequence
<220> FEATURE:
<223> OTHER INFORMATION: CMVtetO in Ad26.CMVtetO_GLuc.AoHV1_RFL

<400> SEQUENCE: 15

```
tcaatattgg ccattagcca tattattcat tggttatata gcataaatca atattggcta     60

ttggccattg catacgttgt atccatatca taatatgtac atttatattg gctcatgtcc    120

aacattaccg ccatgttgac attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtacg ccccctattg acgtcaatga    420

cggtaaatgg cccgcctggc attatgccca gtacatgacc ttatgggact ttcctacttg    480

gcagtacatc tacgtattag tcatcgctat taccatggtg atgcggtttt ggcagtacat    540

caatgggcgt ggatagcggt ttgactcacg gggatttcca agtctccacc ccattgacgt    600

caatgggagt ttgttttggc accaaaatca acgggacttt ccaaaatgtc gtaacaactc    660

cgccccattg acgcaaatgg gcggtaggcg tgtacggtgg gaggtctata taagcagagc    720

tctccctatc agtgatagag atctccctat cagtgataga gatcgtcgac gagctcgttt    780

agtgaaccgt cagatcgcct ggagacgcca tccacgctgt tttgacctcc atagaagaca    840

ccgggaccga tccagcctcc gcggccggga acggtgcatt gga                      883
```

<210> SEQ ID NO 16
<211> LENGTH: 2026
<212> TYPE: DNA
<213> ORGANISM: Artificial Sequence
<220> FEATURE:
<223> OTHER INFORMATION: for construction of pAd26.dE1.dE3.5orf6

<400> SEQUENCE: 16

```
caattgattt aaatcatcat caataatata ccccacaaag taaacaaaag ttaatatgca     60

aatgagcttt tgaattttaa cggttttggg gcggagccaa cgctgattgg acgagaaacg    120

gtgatgcaaa tgacgtcacg acgcacggct aacggtcgcc gcggaggcgt ggcctagccc    180

ggaagcaagt cgcggggctg atgacgtata aaaaagcgga ctttagaccc ggaaacggcc    240

gattttcccg cggccacgcc cggatatgag gtaattctgg gcggatgcaa gtgaaattag    300

gtcattttgg cgcgaaaact gaatgaggaa gtgaaaagcg aaaaataccg gtccctccca    360

gggcggaata tttaccgagg gccgagagac tttgaccgat tacgtggggg tttcgattgc    420

ggtgtttttt tcgcgaattt ccgcgtccgt gtcaaagtcc ggtgtttatg tcacagatca    480

gctgagcgat cgcaggtagg tttgagtagt gggcgtggct aaggtgacta taaaggcggg    540

tgtcttacga gggtcttttt gcttttctgc agacatcatg aacgggactg gcggggcctt    600

cgaagggggg ctttttagcc cttatttgac aacccgcctg ccgggatggg ccggagttcg    660

tcagaatgtg atgggatcga cggtggatgg gcgcccagtg cttccagcaa attcctcgac    720

catgacctac gcgaccgtgg ggaactcgtc gctcgacagc accgccgcag ccgcggcagc    780

cgcagccgcc atgacagcga cgagactggc ctcgagctac atgcccagca gcggtagtag    840

cccctctgtg cccagttcca tcatcgccga ggagaaactg ctggccctgc tggccgagct    900

ggaagccctg tgtacatact ttaatgctcc aaagctagca cccaaaaact gcatgctgga    960

ataagctctc tttgtgtcac cggtgatgcc ttccaatagg tgagtgataa agcgaggtag   1020
```

```
tttttcttta atcatttgag taatagaaaa gtcctctaaa taagtcacta ggaccccagg   1080

aaccacaatg tggtagctga cagcgtgtcg ctcaagcatg gttagtagag atgagagtct   1140

gaaaaacaga aagcatgcac taaaccagag ttgccagtct cactgaagga aaaatcactc   1200

tctccagcag caaagtgccc actgggtggc cctctcggac atacaaaaat cgatccgtgt   1260

ggttaaagag cagcacagtt agctcctgtc ttctcccagc aaagatcaca tcggactggg   1320

ttagtatgcc cctggaatgg tagtcattca aggccataaa tctgccttgg tagccattag   1380

gaatcagcac gctcactctc aagtgaacca aaaccacccc atgcggagga atgtggaaag   1440

attctgggca aaaaaaggta tatctattgc tagtcccttc ctggacggga gcaatccctc   1500

cagggctatc tatgaaagca tacagagatt cagccatagc tcagcccgct taccagtaga   1560

cagagagcac agcagtacaa gcgccaacag cagcgactga ctacccactg acccagctcc   1620

ctatttaaag gcaccttaca ctgacgtaat gaccaaaggt ctaaaaaccc cgccaaaaaa   1680

acacacacgc cctgggtgtt tttcgcgaaa acacttccgc gttctcactt cctcgtatcg   1740

atttcgtgac tcaacttccg ggttcccacg ttacgtcact tctgccctta catgttaatt   1800

aactcagccg tagggcgcca tcttgcccac gtccaaaatg gcttccatgt ccggccacgc   1860

ctccgcggcg accgttagcc gtgcgtcgtg acgtcatttg catcaccgtt tctcgtccaa   1920

tcagcgttgg ctccgcccca aaaccgttaa aattcaaaag ctcatttgca tattaacttt   1980

tgtttacttt gtggggtata ttattgatga tgatttaaat attaat                  2026


<210> SEQ ID NO 17
<211> LENGTH: 1813
<212> TYPE: DNA
<213> ORGANISM: Artificial Sequence
<220> FEATURE:
<223> OTHER INFORMATION: CMV_GLuc_SV

<400> SEQUENCE: 17

accggtgacc cgcgtccgtg tcaaagtccg gtgtttatgt cacagatcag ctgagcgatc     60

tcgagtcaat attggccatt agccatatta ttcattggtt atatagcata aatcaatatt    120

ggctattggc cattgcatac gttgtatcca tatcataata tgtacattta tattggctca    180

tgtccaacat taccgccatg ttgacattga ttattgacta gttattaata gtaatcaatt    240

acggggtcat tagttcatag cccatatatg gagttccgcg ttacataact tacggtaaat    300

ggcccgcctg gctgaccgcc caacgacccc cgcccattga cgtcaataat gacgtatgtt    360

cccatagtaa cgccaatagg gactttccat tgacgtcaat gggtggagta tttacggtaa    420

actgcccact tggcagtaca tcaagtgtat catatgccaa gtacgccccc tattgacgtc    480

aatgacggta aatggcccgc ctggcattat gcccagtaca tgaccttatg ggactttcct    540

acttggcagt acatctacgt attagtcatc gctattacca tggtgatgcg gttttggcag    600

tacatcaatg ggcgtggata gcggtttgac tcacggggat ttccaagtct ccaccccatt    660

gacgtcaatg ggagtttgtt ttggcaccaa aatcaacggg actttccaaa atgtcgtaac    720

aactccgccc cattgacgca aatgggcggt aggcgtgtac ggtgggaggt ctatataagc    780

agagctcgtt tagtgaaccg tcagatcgcc tggagacgcc atccacgctg ttttgacctc    840

catagaagac accgggaccg atccagcctc cgcggccggg aacggtgcat tggagcgatc    900

gcaagcttgc caccatgggc gtgaaggtgc tgttcgccct gatctgtatc gccgtggccg    960

aggccaagcc caccgagaac aacgaggact tcaacatcgt ggccgtggcc tccaacttcg   1020

ccaccaccga tctggacgcc gacagaggca agctgcccgg caagaaactg cccctggaag   1080
```

-continued tgctgaaaga gatggaagcc aacgcccgga aggccggctg taccagaggc tgtctgatct 1140
gcctgagcca cattaagtgc acccccaaga tgaagaagtt catccccggc agatgccaca 1200
cctacgaggg cgacaaagag tctgcccagg gcggaatcgg agaggccatc gtggacatcc 1260
ctgagatccc cggcttcaag gacctggaac ccatggaaca gtttatcgcc caggtggacc 1320
tgtgcgtgga ctgcacaaca ggctgcctga agggcctggc caacgtgcag tgtagcgacc 1380
tgctgaagaa gtggctgccc cagagatgcg ccaccttcgc ctctaagatc cagggacagg 1440
tggacaagat caagggcgct ggcggcgact gagtctagag cgatcgcatc cgaacttgtt 1500
tattgcagct tataatggtt acaaataaag caatagcatc acaaatttca caaataaagc 1560
atttttttca ctgcattcta gttgtggttt gtccaaactc atcaatgtat cttatcatgt 1620
ctgctagcat cgcaggtagg tttgagtagt gggcgtggct aaggtgacta taaaggcggg 1680
tgtcttacga gggtcttttt gcttttctgc agacatcagt cccaatgcat tgcactacac 1740
ctctagtcgt ctcacgcgtc tggcctcat gggccttcct ttcactgccc gctttccagt 1800
cgggaaacct gtc 1813

<210> SEQ ID NO 18
<211> LENGTH: 1813
<212> TYPE: DNA
<213> ORGANISM: Artificial Sequence
<220> FEATURE:
<223> OTHER INFORMATION: CMVtetO_GLuc_SV

<400> SEQUENCE: 18
accggtgacc cgcgtccgtg tcaaagtccg gtgtttatgt cacagatcag ctgagcgatc 60
tcgagtcaat attggccatt agccatatta ttcattggtt atatagcata aatcaatatt 120
ggctattggc cattgcatac gttgtatcca tatcataata tgtacattta tattggctca 180
tgtccaacat taccgccatg ttgacattga ttattgacta gttattaata gtaatcaatt 240
acggggtcat tagttcatag cccatatatg gagttccgcg ttacataact tacggtaaat 300
ggcccgcctg gctgaccgcc caacgacccc cgcccattga cgtcaataat gacgtatgtt 360
cccatagtaa cgccaatagg gactttccat tgacgtcaat gggtggagta tttacggtaa 420
actgcccact tggcagtaca tcaagtgtat catatgccaa gtacgccccc tattgacgtc 480
aatgacggta aatggcccgc ctggcattat gcccagtaca tgaccttatg ggactttcct 540
acttggcagt acatctacgt attagtcatc gctattacca tggtgatgcg gttttggcag 600
tacatcaatg ggcgtggata gcggtttgac tcacggggat ttccaagtct ccaccccatt 660
gacgtcaatg ggagtttgtt ttggcaccaa aatcaacggg actttccaaa atgtcgtaac 720
aactccgccc cattgacgca aatgggcggt aggcgtgtac ggtgggaggt ctatataagc 780
agagctctcc ctatcagtga tagagatctc cctatcagtg atagagatcg tcgacgagct 840
cgtttagtga accgtcagat cgcctggaga cgccatccac gctgttttga cctccataga 900
agacaccggg accgatccag cctccgcggc cgggaacggt gcattggagc gatcgcaagc 960
ttgccaccat gggcgtgaag gtgctgttcg ccctgatctg tatcgccgtg gccgaggcca 1020
agcccaccga gaacaacgag gacttcaaca tcgtggccgt ggcctccaac ttcgccacca 1080
ccgatctgga cgccgacaga ggcaagctgc ccggcaagaa actgcccctg gaagtgctga 1140
aagagatgga agccaacgcc cggaaggccg gctgtaccag aggctgtctg atctgcctga 1200
gccacattaa gtgcaccccc aagatgaaga agttcatccc cggcagatgc cacacctacg 1260

-continued

```
agggcgacaa agagtctgcc cagggcggaa tcggagaggc catcgtggac atccctgaga   1320

tccccggctt caaggacctg gaacccatgg aacagtttat cgcccaggtg gacctgtgcg   1380

tggactgcac aacaggctgc ctgaagggcc tggccaacgt gcagtgtagc gacctgctga   1440

agaagtggct gccccagaga tgcgccacct tcgcctctaa gatccaggga caggtggaca   1500

agatcaaggg cgctggcggc gactgagtct agagcgatcg catccgaact tgtttattgc   1560

agcttataat ggttacaaat aaagcaatag catcacaaat ttcacaaata aagcattttt   1620

ttcactgcat tctagttgtg gtttgtccaa actcatcaat gtatcttatc atgtctgcta   1680

gcatcgcagg taggtttgag tagtgggcgt ggctaaggtg actataaagg cgggtgtctt   1740

acgagggtct tttgcttttt ctgcagacat cagtcccaat gcattgcact acacctctag   1800

tcgtctcacg cgt                                                      1813
```

<210> SEQ ID NO 19
<211> LENGTH: 2548
<212> TYPE: DNA
<213> ORGANISM: Artificial Sequence
<220> FEATURE:
<223> OTHER INFORMATION: AoHV1_RFL_BGH

<400> SEQUENCE: 19

```
gacggtctca cgcgtcacgt ggccggacat ggaagccatt ttggacgtgg gcaagatggc     60

gccctacggc tgagttaatg gatccaaatc aatgacttgg caagcatata catccgtcct    120

ggcaccagaa taggggttaa atggggactt tccataagcc caccgcctca tttggcacca    180

aaaaggggga tttctattat tagtcaatgt ccttggccaa tagccagtga cgtcaatggg    240

aacggggcca gttccccttt cccaccatta ccggcaatgg tgggtgggga aattccatat    300

tagtcaatgt tcttggcacc aaaaccgcgg ggactttcca ttgacgtcag tggaaagggg    360

cgtaacgggg agtgaccatg ggcgttcccg ggcggagtta tgggcgttac tgggcggttc    420

gtgggcggac catgggctgt cctagggtat ataagcagag cccggttagc agaccgccat    480

tcgccttcaa gacagcgtga gggacccacg ttctccggac cagccaccgg gaccgagcgg    540

cctagcctag ccggggaccc ttcactggtt aattaaggcg cgccaccatg gagaacatgg    600

aaaacgacga gaacatcgtc gtgggcccca agcccttcta ccccatcgag gaaggctctg    660

ccggcaccca gctgcggaag tacatggaaa gatacgccaa gctgggcgct atcgccttca    720

ccaatgccgt gaccggcgtg gactacagct acgccgagta cctggaaaag agctgctgcc    780

tgggcaaggc cctgcagaac tatggcctgg tggtggacgg cagaatcgcc ctgtgcagcg    840

agaactgcga agagttcttc atccccgtga tcgccggcct gttcatcgga gtgggagtgg    900

cccccaccaa cgagatctac accctgcggg aactggtgca cagcctgggc atcagcaagc    960

ccaccatcgt gttcagcagc aagaaaggcc tggacaaagt gatcaccgtg cagaaaaccg   1020

tgaccaccat caagaccatc gtgatcctgg acagcaaggt ggactaccgg ggctaccagt   1080

gcctggacac cttcatcaag cggaacaccc ccccaggctt ccaggcctcc agcttcaaga   1140

ccgtggaagt ggaccggaaa gaacaggtgg ccctgatcat gaacagcagc ggcagcaccg   1200

gactgcccaa aggcgtgcag ctgacccacg agaacaccgt gacacggttc agccacgccc   1260

gggaccccat ctacggaaac caggtgtccc ctggcaccgc cgtgctgacc gtggtgcctt   1320

ttcaccacgg cttcggcatg ttcaccaccc tgggctacct gatctgcggc ttccgggtcg   1380

tgatgctgac caagttcgac gaggaaacct tcctgaaaac cctgcaggac tacaagtgca   1440

cctatgtgat cctggtgccc accctgttcg ccatcctgaa caagagcgaa ctgctgaaca   1500
```

aatacgacct gagcaacctg gtggaaatcg ccagcggagg cgcccctctg agcaaagaag 1560
tgggagaggc cgtggccaga cggttcaatc tgcctggcgt gcggcagggc tacggcctga 1620
cagaaacaac cagcgccatc atcatcaccc ccgagggcga cgataagcct ggcgcctctg 1680
gaaaggtggt gcccctgttc aaggccaaag tgattgacct ggataccaag aagtccctgg 1740
gccctaacag acggggcgaa gtgtgcgtga agggccccat gctgatgaag ggctacgtga 1800
acaaccccga ggccaccaaa gagctgatcg acgaagaggg ctggctgcac accggcgaca 1860
tcggctacta cgatgaggaa aagcacttct tcatcgtgga ccggctgaag tctctgatca 1920
agtacaaggg ctatcaggtg ccccctgccg agctggaatc tgtgctgctg cagcatccca 1980
gcatcttcga cgctggcgtg gcaggcgtgc cagatcctgt ggctggcgaa ctgccaggcg 2040
ctgtggtggt gctggaaagc ggcaagaaca tgaccgagaa agaagtgatg gactacgtgg 2100
cctctcaggt gtccaacgcc aagagactga gaggcggcgt cagattcgtg gacgaggtgc 2160
caaagggcct gaccggcaag atcgatggca gagccatcag agagatcctg aagaaacccg 2220
tggccaagat gtgaattcct taattaactg tgccttctag ttgccagcca tctgttgttt 2280
gcccctcccc cgtgccttcc ttgaccctgg aaggtgccac tcccactgtc ctttcctaat 2340
aaaatgagga aattgcatcg cattgtctga gtaggtgtca ttctattctg gggggtgggg 2400
tggggcagga cagcaagggg gaggattggg aagacaatag caggcatgct ggggatgcgg 2460
tgggctctat ggtaccatta acatgtaagg gcagaagtga cgtaacgtgg gaacccggaa 2520
gttgagtcac gtgccaatgc attgggtg 2548

<210> SEQ ID NO 20
<211> LENGTH: 1322
<212> TYPE: DNA
<213> ORGANISM: Artificial Sequence
<220> FEATURE:
<223> OTHER INFORMATION: for construction of pC_AoHV_TetR

<400> SEQUENCE: 20
caattgcatg aagaatctgc ttagggttag gcgttttgcg ctgcttcgct aggtggtcaa 60
tattggccat tagccatatt attcattggt tatatagcat aaatcaatat tggctattgg 120
ccattgcata cgttgtatcc atatcataat atgtacattt atattggctc atgtccaaca 180
ttaccgccat gacgcgtaaa tcaatgactt ggcaagcata tacatccgtc ctggcaccag 240
aataggggtt aaatggggac tttccataag cccaccgcct catttggcac caaaaagggg 300
gatttctatt attagtcaat gtccttggcc aatagccagt gacgtcaatg ggaacggggc 360
cagttcccct ttcccaccat taccggcaat ggtgggtggg gaaattccat attagtcaat 420
gttcttggca ccaaaaccgc ggggactttc cattgacgtc agtggaaagg ggcgtaacgg 480
ggagtgacca tgggcgttcc cgggcggagt tatgggcgtt actgggcggt tcgtgggcgg 540
accatgggct gtcctagggt atataagcag agcccggtta gcagaccgcc attcgccttc 600
aagacagcgt gagggaccca cgttctccgg accagccacc gggaccgagc ggcctagcct 660
agccggggac ccttcactgg cgcgccacca tgagccggct ggacaagagc aaagtgatca 720
acagcgccct ggaactgctg aacgaagtgg gcatcgaggg cctgaccacc cggaagctgg 780
cccagaaact gggcgtggaa cagcccaccc tgtactggca cgtgaagaac aagcgggccc 840
tgctggacgc cctggccatc gagatgctgg accggcacca cacccacttt tgcccccctgg 900 aaggcgagag ctggcaggac ttcctgcgga acaacgccaa gagcttcaga tgcgccctgc 960

-continued

```
tgagccacag ggacggcgcc aaggtgcacc tgggcaccag acccaccgag aagcagtacg   1020

agacactgga aaaccagctg gccttcctgt gccagcaggg cttcagcctg gaaaacgccc   1080

tgtacgccct gagcgccgtg ggccacttta ccctgggctg cgtgctggaa gatcaggaac   1140

accaggtcgc caaagaggaa agagagacac ccaccaccga cagcatgccc cccctgctga   1200

gacaggccat cgagctattc gatcaccaag gcgccgagcc cgccttcctg ttcggcctgg   1260

aactgatcat ctgcggcctc gagaagcagc tgaagtgcga gagcggctcc tgataatcta   1320

ga                                                                 1322
```

<210> SEQ ID NO 21
<211> LENGTH: 6535
<212> TYPE: DNA
<213> ORGANISM: Artificial Sequence
<220> FEATURE:
<223> OTHER INFORMATION: pDualLuc

<400> SEQUENCE: 21

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattgaagg aaggccgtca    360

aggccgcata ccggtgaccc gcgtccgtgt caaagtccgg tgtttatgtc acagatcagc    420

tgagcgatct cgagtcaata ttggccatta gccatattat tcattggtta tatagcataa    480

atcaatattg gctattggcc attgcatacg ttgtatccat atcataatat gtacatttat    540

attggctcat gtccaacatt accgccatgt tgacattgat tattgactag ttattaatag    600

taatcaatta cggggtcatt agttcatagc ccatatatgg agttccgcgt tacataactt    660

acggtaaatg gcccgcctgg ctgaccgccc aacgaccccc gcccattgac gtcaataatg    720

acgtatgttc ccatagtaac gccaataggg actttccatt gacgtcaatg ggtggagtat    780

ttacggtaaa ctgcccactt ggcagtacat caagtgtatc atatgccaag tacgccccct    840

attgacgtca atgacggtaa atggcccgcc tggcattatg cccagtacat gaccttatgg    900

gactttccta cttggcagta catctacgta ttagtcatcg ctattaccat ggtgatgcgg    960

ttttggcagt acatcaatgg gcgtggatag cggtttgact cacggggatt tccaagtctc   1020

caccccattg acgtcaatgg gagtttgttt tggcaccaaa atcaacggga ctttccaaaa   1080

tgtcgtaaca actccgcccc attgacgcaa atgggcggta ggcgtgtacg gtgggaggtc   1140

tatataagca gagctcgttt agtgaaccgt cagatcgcct ggagacgcca tccacgctgt   1200

tttgacctcc atagaagaca ccgggaccga tccagcctcc gcggccggga acggtgcatt   1260

ggagcgatcg caagcttgcc accatgggcg tgaaggtgct gttcgccctg atctgtatcg   1320

ccgtggccga ggccaagccc accgagaaca acgaggactt caacatcgtg gccgtggcct   1380

ccaacttcgc caccaccgat ctggacgccg acagaggcaa gctgcccggc aagaaactgc   1440

ccctggaagt gctgaaagag atggaagcca acgcccggaa ggccggctgt accagaggct   1500

gtctgatctg cctgagccac attaagtgca cccccaagat gaagaagttc atccccggca   1560

gatgccacac ctacgagggc gacaaagagt ctgcccaggg cggaatcgga gaggccatcg   1620

tggacatccc tgagatcccc ggcttcaagg acctggaacc catggaacag tttatcgccc   1680
```

-continued aggtggacct gtgcgtggac tgcacaacag gctgcctgaa gggcctggcc aacgtgcagt 1740
gtagcgacct gctgaagaag tggctgcccc agagatgcgc caccttcgcc tctaagatcc 1800
agggacaggt ggacaagatc aagggcgctg gcggcgactg agtctagagc gatcgcatcc 1860
gaacttgttt attgcagctt ataatggtta caaataaagc aatagcatca caaatttcac 1920
aaataaagca tttttttcac tgcattctag ttgtggtttg tccaaactca tcaatgtatc 1980
ttatcatgtc tgctagcatc gcaggtaggt ttgagtagtg ggcgtggcta aggtgactat 2040
aaaggcgggt gtcttacgag ggtctttttg cttttctgca gacatcagtc ccaatgcatt 2100
ggcacgtgac tcaacttccg ggttcccacg ttacgtcact tctgccctta catgttaatg 2160
gtaccataga gcccaccgca tccccagcat gcctgctatt gtcttcccaa tcctccccct 2220
tgctgtcctg ccccacccca ccccccagaa tagaatgaca cctactcaga caatgcgatg 2280
caatttcctc attttattag gaaaggacag tgggagtggc accttccagg gtcaaggaag 2340
gcacggggga ggggcaaaca acagatggct ggcaactaga aggcacagtt aattaaggaa 2400
ttcacatctt ggccacgggt ttcttcagga tctctctgat ggctctgcca tcgatcttgc 2460
cggtcaggcc ctttggcacc tcgtccacga atctgacgcc gcctctcagt ctcttggcgt 2520
tggacacctg agaggccacg tagtccatca cttctttctc ggtcatgttc ttgccgcttt 2580
ccagcaccac cacagcgcct ggcagttcgc cagccacagg atctggcacg cctgccacgc 2640
cagcgtcgaa gatgctggga tgctgcagca gcacagattc cagctcggca gggggcacct 2700
gatagccctt gtacttgatc agagacttca gccggtccac gatgaagaag tgcttttcct 2760
catcgtagta gccgatgtcg ccggtgtgca gccagccctc ttcgtcgatc agctctttgg 2820
tggcctcggg gttgttcacg tagcccttca tcagcatggg gcccttcacg cacacttcgc 2880
cccgtctgtt agggcccagg gacttcttgg tatccaggtc aatcactttg gccttgaaca 2940
ggggcaccac ctttccagag gcgccaggct tatcgtcgcc ctcgggggtg atgatgatgg 3000
cgctggttgt ttctgtcagg ccgtagccct gccgcacgcc aggcagattg aaccgtctgg 3060
ccacggcctc tcccacttct ttgctcagag ggcgcctcc gctggcgatt tccaccaggt 3120
tgctcaggtc gtatttgttc agcagttcgc tcttgttcag gatggcgaac agggtgggca 3180
ccaggatcac ataggtgcac ttgtagtcct gcagggtttt caggaaggtt tcctcgtcga 3240
acttggtcag catcacgacc cggaagccgc agatcaggta gcccagggtg gtgaacatgc 3300
cgaagccgtg gtgaaaaggc accacggtca gcacggcggt gccaggggac acctggtttc 3360
cgtagatggg gtcccgggcg tggctgaacc gtgtcacggt gttctcgtgg gtcagctgca 3420
cgcctttggg cagtccggtg ctgccgctgc tgttcatgat cagggccacc tgttctttcc 3480
ggtccacttc cacggtcttg aagctggagg cctggaagcc tggggggtg ttccgcttga 3540
tgaaggtgtc caggcactgg tagccccggt agtccacctt gctgtccagg atcacgatgg 3600
tcttgatggt ggtcacggtt ttctgcacgg tgatcacttt gtccaggcct ttcttgctgc 3660
tgaacacgat ggtgggcttg ctgatgccca ggctgtgcac cagttcccgc agggtgtaga 3720
tctcgttggt gggggccact cccactccga tgaacaggcc ggcgatcacg gggatgaaga 3780
actcttcgca gttctcgctg cacagggcga ttctgccgtc caccaccagg ccatagttct 3840
gcagggcctt gcccaggcag cagctctttt ccaggtactc ggcgtagctg tagtccacgc 3900
cggtcacggc attggtgaag gcgatagcgc ccagcttggc gtatctttcc atgtacttcc 3960
gcagctgggt gccggcagag ccttcctcga tggggtagaa gggcttgggg cccacgacga 4020

-continued tgttctcgtc gttttccatg ttctccatgg tggcgcgcct taattaacca gtgaagggtc 4080
cccggctagg ctaggccgct cggtcccggt ggctggtccg gagaacgtgg gtccctcacg 4140
ctgtcttgaa ggcgaatggc ggtctgctaa ccgggctctg cttatatacc ctaggacagc 4200
ccatggtccg cccacgaacc gcccagtaac gcccataact ccgcccggga acgcccatgg 4260
tcactccccg ttacgcccct ttccactgac gtcaatggaa agtccccgcg gttttggtgc 4320
caagaacatt gactaatatg gaatttcccc acccaccatt gccggtaatg gtgggaaagg 4380
ggaactggcc ccgttcccat tgacgtcact ggctattggc caaggacatt gactaataat 4440
agaaatcccc ctttttggtg ccaaatgagg cggtgggctt atggaaagtc cccatttaac 4500
ccctattctg gtgccaggac ggatgtatat gcttgccaag tcattgattt ggatccatta 4560
actcagccgt agggcgccat cttgcccacg tccaaaatgg cttccatgtc cggccacgtg 4620
acgcgtctgg gcctcatggg ccttcctttc actgcccgct ttccagtcgg gaaacctgtc 4680
gtgccagctg cattaacatg gtcatagctg tttccttgcg tattgggcgc tctccgcttc 4740
ctcgctcact gactcgctgc gctcggtcgt tcgggtaaag cctggggtgc ctaatgagca 4800
aaaggccagc aaaaggccag gaaccgtaaa aaggccgcgt tgctggcgtt tttccatagg 4860
ctccgccccc ctgacgagca tcacaaaaat cgacgctcaa gtcagaggtg gcgaaacccg 4920
acaggactat aaagatacca ggcgtttccc cctggaagct ccctcgtgcg ctctcctgtt 4980
ccgaccctgc cgcttaccgg atacctgtcc gcctttctcc cttcgggaag cgtggcgctt 5040
tctcatagct cacgctgtag gtatctcagt tcggtgtagg tcgttcgctc caagctgggc 5100
tgtgtgcacg aaccccccgt tcagcccgac cgctgcgcct tatccggtaa ctatcgtctt 5160
gagtccaacc cggtaagaca cgacttatcg ccactggcag cagccactgg taacaggatt 5220
agcagagcga ggtatgtagg cggtgctaca gagttcttga agtggtggcc taactacggc 5280
tacactagaa gaacagtatt tggtatctgc gctctgctga agccagttac cttcggaaaa 5340
agagttggta gctcttgatc cggcaaacaa accaccgctg gtagcggtgg tttttttgtt 5400
tgcaagcagc agattacgcg cagaaaaaaa ggatctcaag aagatccttt gatcttttct 5460
acggggtctg acgctcagtg gaacgaaaac tcacgttaag ggattttggt catgagatta 5520
tcaaaaagga tcttcaccta gatcctttta aattaaaaat gaagttttaa atcaatctaa 5580
agtatatatg agtaaacttg gtctgacagt tattagaaaa attcatccag cagacgataa 5640
aacgcaatac gctggctatc cggtgccgca atgccataca gcaccagaaa acgatccgcc 5700
cattcgccgc ccagttcttc cgcaatatca cgggtggcca gcgcaatatc ctgataacga 5760
tccgccacgc ccagacggcc gcaatcaata aagccgctaa aacggccatt ttccaccata 5820
atgttcggca ggcacgcatc accatgggtc accaccagat cttcgccatc cggcatgctc 5880
gctttcagac gcgcaaacag ctctgccggt gccaggccct gatgttcttc atccagatca 5940
tcctgatcca ccaggcccgc ttccatacgg gtacgcgcac gttcaatacg atgtttcgcc 6000
tgatgatcaa acggacaggt cgccgggtcc agggtatgca gacgacgcat ggcatccgcc 6060
ataatgctca ctttttctgc cggcgccaga tggctagaca gcagatcctg acccggcact 6120
tcgcccagca gcagccaatc acggcccgct tcggtcacca catccagcac cgccgcacac 6180
ggaacaccgg tggtggccag ccagctcaga cgcgccgctt catcctgcag ctcgttcagc 6240
gcaccgctca gatcggtttt cacaaacagc accggacgac cctgcgcgct cagacgaaac 6300
accgccgcat cagagcagcc aatggtctgc tgcgcccaat catagccaaa cagacgttcc 6360
acccacgctg ccgggctacc cgcatgcagg ccatcctgtt caatcatact cttccttttt 6420

-continued

```
caatattatt gaagcattta tcagggttat tgtctcatga gcggatacat atttgaatgt   6480

atttagaaaa ataaacaaat aggggttccg cgcacatttc cccgaaaagt gccac        6535
```

<210> SEQ ID NO 22
<211> LENGTH: 1529
<212> TYPE: DNA
<213> ORGANISM: Artificial Sequence
<220> FEATURE:
<223> OTHER INFORMATION: v01

<400> SEQUENCE: 22

```
tgtggtgtcg tggccttggc ccggtgccaa gtattgcgac tatctggcac tgtgtcaagt     60

tattgatggg tatcattgat gcctgattga catctgtcaa tgcacatcta taatgatcaa    120

taagtttaaa ttgagtcttt gactatgagc cagacatctg tcaccaatac atcaatctga    180

gtgttcaata aaccatattg gaattcatat caatatactg gatgtcagcc agctaaaaaa    240

ataaacaata aaatcgtcac ctggcattca gccaatggat caatgtattg gctgaatgcc    300

atactattga tatatagata atctattgcc aattaattgg ccatatagcc aatacaatgg    360

cacggggcca atgtattggc tatatatcaa tatgatggcg ggttccagt atattaatat     420

attgccaatg tattggctat atatcaatat ggtggcaagg ttccagtata ttaatctatt    480

ggcaatctat tggccatata tcaatatggt ggcaaggttc cagtatatta atctattggc    540

aatctattgg ccatatatca atatggtggc aaggttccag tatattaatc tattggcaat    600

ctattggcca tatatcaata tggtggcaag gttccagtat attaatctat tggcaatcta    660

ttggccatat atcaatatgg tggcagtgac ccaagttatt aatctattgc caatataggc    720

caatagattg gagatgagcc agtctatcaa tccataatca atatatatct atcagtattg    780

ggacatatat tgattagtat ggggtcaaat agggtatttc cgtgttccca tcaatacttg    840

gcacaaacaa cactatgact caatgggcta tgggccaaga acataggtca aatagggtat    900

ttccgtgttc ccatctgtac ttggcacaaa caacactatg actcaatagg ctatttgcca    960

agaacataag gtcaatcagg gtacttccgc gttcccaccg ccccatttgg caacaaaata   1020

ggggttattt gggggtcttc cccttgaaat caatgacttg gcaagcatat acatccgtcc   1080

tggcaccaga ataggggtta aatggggact ttccataagc ccaccgcctc atttggcacc   1140

aaaaaggggg atttctatta ttagtcaatg tccttggcca atagccagtg acgtcaatgg   1200

gaacggggcc agttcccctt tcccaccatt accggcaatg gtgggtgggg aaattccata   1260

ttagtcaatg ttcttggcac caaaaccgcg gggactttcc attgacgtca gtggaaaggg   1320

gcgtaacggg gagtgaccat gggcgttccc gggcggagtt atgggcgtta ctgggcggtt   1380

cgtgggcgga ccatgggctg tcctagggta tataagcaga gcccggttag cagaccgcca   1440

ttcgccttca agacagcgtg agggacccac gttctccgga ccagccaccg ggaccgagcg   1500

gcctagccta gccggggacc cttcactgg                                     1529
```

<210> SEQ ID NO 23
<211> LENGTH: 660
<212> TYPE: DNA
<213> ORGANISM: Artificial Sequence
<220> FEATURE:
<223> OTHER INFORMATION: v02

<400> SEQUENCE: 23

```
atgggccaag aacataggtc aaatagggta tttccgtgtt cccatctgta cttggcacaa     60
```

-continued

```
acaacactat gactcaatag gctatttgcc aagaacataa ggtcaatcag ggtacttccg    120

cgttcccacc gccccatttg gcaacaaaat aggggttatt tgggggtctt ccccttgaaa    180

tcaatgactt ggcaagcata tacatccgtc ctggcaccag aataggggtt aaatggggac    240

tttccataag cccaccgcct catttggcac caaaaagggg gatttctatt attagtcaat    300

gtccttggcc aatagccagt gacgtcaatg ggaacggggc cagttcccct ttcccaccat    360

taccggcaat ggtgggtggg gaaattccat attagtcaat gttcttggca ccaaaaccgc    420

ggggactttc cattgacgtc agtggaaagg ggcgtaacgg ggagtgacca tgggcgttcc    480

cgggcggagt tatgggcgtt actgggcggt tcgtgggcgg accatgggct gtcctagggt    540

atataagcag agcccggtta gcagaccgcc attcgccttc aagacagcgt gagggaccca    600

cgttctccgg accagccacc gggaccgagc ggcctagcct agccggggac ccttcactgg    660
```

```
<210> SEQ ID NO 24
<211> LENGTH: 1157
<212> TYPE: DNA
<213> ORGANISM: Artificial Sequence
<220> FEATURE:
<223> OTHER INFORMATION: v03

<400> SEQUENCE: 24

aaatcaatga cttggcaagc atatacatcc gtcctggcac cagaataggg gttaaatggg     60

gactttccat aagcccaccg cctcatttgg caccaaaaag ggggatttct attattagtc    120

aatgtccttg gccaatagcc agtgacgtca atgggaacgg ggccagttcc cctttcccac    180

cattaccggc aatggtgggt ggggaaattc catattagtc aatgttcttg gcaccaaaac    240

cgcggggact ttccattgac gtcagtggaa aggggcgtaa cggggagtga ccatgggcgt    300

tcccgggcgg agttatgggc gttactgggc ggttcgtggg cggaccatgg gctgtcctag    360

ggtatataag cagagcccgg ttagcagacc gccattcgcc ttcaagacag cgtgagggac    420

ccacgttctc cggaccagcc accgggaccg agcggcctag cctagccggg gacccttcac    480

tggaacgcgg atacagcgtg ccaaattaag gtatggagcg cggatggtat agcttgcatg    540

ctgattggtg gctggtggcg gtatctatag tatataatgt atagcctatt catggtatag    600

gcctccatat tgggggctgt gccgccattt taatgcatgg atgacgtgtg ggcttaatgt    660

atagatattg attattgatt aatcatggca gccatagctt ttatctgcat gttaatgata    720

cagctgccat tactatgtgc ccttatgccc tatatgttac taatttcctt gttggcacag    780

tgcctaacag tgctaatgta tgctttgcta taatgggcgg tgggccaggc ctggcatcgg    840

gccaactttt tgctaattgc tgggggcgct tctccatgtt gttgtggttt attattttgg    900

cacccggcca ttatgcggag cccctgtcag tcgaaacccg ggttttggca ccgtgccaaa    960

ttcacgtcat ccatacatag agctataatg tgatttggtg atggttaaca tatggtgatg   1020

cgtcagtaca ttcatgacaa cacgccacac acactttagg ctgcatgccc tctccacaca   1080

ctcttttctg gacgcttgcc agttttggcc cagtgccaat ttaccgctac agacacagta   1140

aactgagtta gattgtt                                                  1157
```

```
<210> SEQ ID NO 25
<211> LENGTH: 371
<212> TYPE: DNA
<213> ORGANISM: Artificial Sequence
<220> FEATURE:
<223> OTHER INFORMATION: v04

<400> SEQUENCE: 25
```

```
tattagtcaa tgtccttggc caatagccag tgacgtcaat gggaacgggg ccagttcccc     60

tttcccacca ttaccggcaa tggtgggtgg ggaaattcca tattagtcaa tgttcttggc    120

accaaaaccg cggggacttt ccattgacgt cagtggaaag ggcgtaacgg gggagtgacc    180

atgggcgttc ccgggcggag ttatgggcgt tactgggcgg ttcgtgggcg gaccatgggc    240

tgtcctaggg tatataagca gagcccggtt agcagaccgc cattcgcctt caagacagcg    300

tgagggaccc acgttctccg gaccagccac cgggaccgag cggcctagcc tagccgggga    360

cccttcactg g                                                         371
```

<210> SEQ ID NO 26
<211> LENGTH: 241
<212> TYPE: DNA
<213> ORGANISM: Artificial Sequence
<220> FEATURE:
<223> OTHER INFORMATION: v05

<400> SEQUENCE: 26

```
cggggacttt ccattgacgt cagtggaaag ggcgtaacgg gggagtgacc atgggcgttc     60

ccgggcggag ttatgggcgt tactgggcgg ttcgtgggcg gaccatgggc tgtcctaggg    120

tatataagca gagcccggtt agcagaccgc cattcgcctt caagacagcg tgagggaccc    180

acgttctccg gaccagccac cgggaccgag cggcctagcc tagccgggga cccttcactg    240

g                                                                    241
```

<210> SEQ ID NO 27
<211> LENGTH: 1728
<212> TYPE: DNA
<213> ORGANISM: Artificial Sequence
<220> FEATURE:
<223> OTHER INFORMATION: v07

<400> SEQUENCE: 27

```
aaatcaatga cttggcaagc atatacatcc gtcctggcac cagaataggg gttaaatggg     60

gactttccat aagcccaccg cctcatttgg caccaaaaag gggatttct attattagtc    120

aatgtccttg gccaatagcc agtgacgtca atgggaacgg ggccagttcc cctttcccac    180

cattaccggc aatggtgggt ggggaaattc catattagtc aatgttcttg gcaccaaaac    240

cgcggggact ttccattgac gtcagtggaa aggggcgtaa cggggagtga ccatgggcgt    300

tcccgggcgg agttatgggc gttactgggc ggttcgtggg cggaccatgg gctgtcctag    360

ggtatataag cagagcccgg ttagcagacc gccattcgcc ttcaagacag cgtgagggac    420

ccacgttctc cggaccagcc accgggaccg agcggcctag cctagccggg gacccttcac    480

tggaacgcgg atacagcgtg ccaaattaag gtatggagcg cggatggtat agcttgcatg    540

ctgattggtg gctggtggcg gtatctatag tatataatgt atagcctatt catggtatag    600

gcctccatat tgggggctgt gccgccattt taatgcatgg atgacgtgtg ggcttaatgt    660

atagatattg attattgatt aatcatggca gccatagctt ttatctgcat gttaatgata    720

cagctgccat tactatgtgc ccttatgccc tatatgttac taatttcctt gttggcacag    780

tgcctaacag tgctaatgta tgctttgcta taatgggcgg tgggccaggc ctggcatcgg    840

gccaactttt tgctaattgc tgggggcgct tctccatgtt gttgtggttt attattttgg    900

cacccggcca ttatgcggag cccctgtcag tcgaaacccg ggttttggca ccgtgccaaa    960

ttcacgtcat ccatacatag agctataatg tgatttggtg atggttaaca tatggtgatg   1020
```

```
cgtcagtaca ttcatgacaa cacgccacac acactttagg ctgcatgccc tctccacaca   1080

ctcttttctg gacgcttgcc agttttggcc cagtgccaat ttaccgctac agacacagta   1140

aactgagtta gattgtttta ttcacaggga actgttattg acagggctgg tacacagtcc   1200

tctttgccca tctcaggcac atcaatgatg gtgtcctggg ggacccggtt caaggcctct   1260

gcttcctcca tgatctcttg cacagcttcc tccagattct tgtcagtaga gcagaaactg   1320

cacatcatga ctgtgattat aagtccgaac atacacagta tagcgcctat ggagctcacg   1380

gggcgcatcc aggcattatg tgcaaaagat agtacatgcg aacggtcaga gcttctcccg   1440

gtggtagtag gttgacttga ggtaagaatg gtggtgctca cagtagtaga tgagtgatct   1500

agaaatggac attagtctta atatctattt ttagatcaca tgaggggggg taggcttcat   1560

gaatgttgtc tctgtccact tactggtggt ttgagtgaca cttgtggtga cattatcagc   1620

agtggtggcg ttgagcatcc aggcgatggc gcatccacag atgataagtc ccagggggtc   1680

caggtccctg aaggtaacag gtgtttgtgt ttactcacag ctgtaaag                1728
```

```
<210> SEQ ID NO 28
<211> LENGTH: 1224
<212> TYPE: DNA
<213> ORGANISM: Artificial Sequence
<220> FEATURE:
<223> OTHER INFORMATION: v08

<400> SEQUENCE: 28

aaatcaatga cttggcaagc atatacatcc gtcctggcac cagaataggg gttaaatggg     60

gactttccat aagcccaccg cctcatttgg caccaaaaag gggatttct attattagtc     120

aatgtccttg gccaatagcc agtgacgtca atgggaacgg ggccagttcc cctttcccac    180

cattaccggc aatggtgggt ggggaaattc catattagtc aatgttcttg gcaccaaaac    240

cgcggggact ttccattgac gtcagtggaa aggggcgtaa cggggagtga ccatgggcgt    300

tcccgggcgg agttatgggc gttactgggc ggttcgtggg cggaccatgg gctgtcctag    360

ggtatataag cagagcccgg ttagcagacc gccattcgcc ttcaagacag cgtgagggac    420

ccacgttctc cggaccagcc accgggaccg agcggcctag cctagccggg gacccttcac    480

tggaacgcgg atacagcgtg ccaaattaag gtatggagcg cggatggtat agcttgcatg    540

ctgattggtg gctggtggcg gtatctatag tatataatgt atagcctatt catggtatag    600

gcctccatat tgggggctgt gccgccattt taatgcatgg atgacgtgtg ggcttaatgt    660

atagatattg attattgatt aatcatggca gccatagctt ttatctgcat gttaatgata    720

cagctgccat tactatgtgc ccttatgccc tatatgttac taatttcctt gttggcacag    780

tgcctaacag tgctaatgta tgctttgcta taatgggcgg tgggccaggc ctggcatcgg    840

gccaactttt tgctaattgc tgggggcgct tctccatgtt gttgtggttt attattttgg    900

cacccggcca ttatgcggag cccctgtcag tcgaaacccg ggttttggca ccgtgccaaa    960

ttcacgtcat ccatacatag agctataatg tgatttggtg atggttaaca tatggtgatg   1020

cgtcagtaca ttcatgacaa cacgccacac acactttagg ctgcatgccc tctccacaca   1080

ctcttttctg gacgcttgcc agttttggcc cagtgccaat ttaccgctac agacacagta   1140

aactgagtta gattgtttta ttcacaggga actgttattg acagggctgg tacacagtcc   1200

tctttgccca tctcaggcac atca                                          1224

<210> SEQ ID NO 29
<211> LENGTH: 658
```

<212> TYPE: DNA
<213> ORGANISM: Artificial Sequence
<220> FEATURE:
<223> OTHER INFORMATION: v09

<400> SEQUENCE: 29
aaatcaatga cttggcaagc atatacatcc gtcctggcac cagaataggg gttaaatggg 60
gactttccat aagcccaccg cctcatttgg caccaaaaag gggatttct attattagtc 120 aatgtccttg gccaatagcc agtgacgtca atgggaacgg ggccagttcc cctttcccac 180
cattaccggc aatggtgggt ggggaaattc catattagtc aatgttcttg gcaccaaaac 240
cgcggggact ttccattgac gtcagtggaa aggggcgtaa cggggagtga ccatgggcgt 300
tcccgggcgg agttatgggc gttactgggc ggttcgtggg cggaccatgg gctgtcctag 360
ggtatataag cagagcccgg ttagcagacc gccattcgcc ttcaagacag cgtgagggac 420
ccacgttctc cggaccagcc accgggaccg agcggcctag cctagccggg gacccttcac 480
tggaacgcgg atacagcgtg ccaaattaag gtatggagcg cggatggtat agcttgcatg 540
ctgattggtg gctggtggcg gtatctatcc aggcgatggc gcatccacag atgataagtc 600
ccagggggtc caggtccctg aaggtaacag gtgtttgtgt ttactcacag ctgtaaag 658

<210> SEQ ID NO 30
<211> LENGTH: 483
<212> TYPE: DNA
<213> ORGANISM: Artificial Sequence
<220> FEATURE:
<223> OTHER INFORMATION: AoHV-1 short (with native AvrII site)

<400> SEQUENCE: 30
aaatcaatga cttggcaagc atatacatcc gtcctggcac cagaataggg gttaaatggg 60
gactttccat aagcccaccg cctcatttgg caccaaaaag gggatttct attattagtc 120 aatgtccttg gccaatagcc agtgacgtca atgggaacgg ggccagttcc cctttcccac 180
cattaccggc aatggtgggt ggggaaattc catattagtc aatgttcttg gcaccaaaac 240
cgcggggact ttccattgac gtcagtggaa aggggcgtaa cggggagtga ccatgggcgt 300
tcccgggcgg agttatgggc gttactgggc ggttcgtggg cggaccatgg gctgtcctag 360
ggtatataag cagagcccgg ttagcagacc gccattcgcc ttcaagacag cgtgagggac 420
ccacgttctc cggaccagcc accgggaccg agcggcctag cctagccggg gacccttcac 480
tgg 483

<210> SEQ ID NO 31
<211> LENGTH: 67
<212> TYPE: DNA
<213> ORGANISM: Artificial Sequence
<220> FEATURE:
<223> OTHER INFORMATION: AoHV-1 core promoter

<400> SEQUENCE: 31
ggcggaccat gggctgtcct agggtatata agcagagccc ggttagcaga ccgccattcg 60
ccttcaa 67

<210> SEQ ID NO 32
<211> LENGTH: 2774
<212> TYPE: DNA
<213> ORGANISM: Artificial Sequence
<220> FEATURE:
<223> OTHER INFORMATION: AoHV-1 genome fragment

<400> SEQUENCE: 32
tgtggtgtcg tggccttggc ccggtgccaa gtattgcgac tatctggcac tgtgtcaagt 60
tattgatggg tatcattgat gcctgattga catctgtcaa tgcacatcta taatgatcaa 120
taagtttaaa ttgagtcttt gactatgagc cagacatctg tcaccaatac atcaatctga 180
gtgttcaata aaccatattg gaattcatat caatatactg gatgtcagcc agctaaaaaa 240
ataaacaata aaatcgtcac ctggcattca gccaatggat caatgtattg gctgaatgcc 300
atactattga tatatagata atctattgcc aattaattgg ccatatagcc aatacaatgg 360
cacggggcca atgtattggc tatatatcaa tatgatggcg gggttccagt atattaatat 420
attgccaatg tattggctat atatcaatat ggtggcaagg ttccagtata ttaatctatt 480
ggcaatctat tggccatata tcaatatggt ggcaaggttc cagtatatta atctattggc 540
aatctattgg ccatatatca atatggtggc aaggttccag tatattaatc tattggcaat 600
ctattggcca tatatcaata tggtggcaag gttccagtat attaatctat tggcaatcta 660
ttggccatat atcaatatgg tggcagtgac ccaagttatt aatctattgc caatataggc 720
caatagattg gagatgagcc agtctatcaa tccataatca atatatatct atcagtattg 780
ggacatatat tgattagtat ggggtcaaat agggtatttc cgtgttccca tcaatacttg 840
gcacaaacaa cactatgact caatgggcta tgggccaaga acataggtca aatagggtat 900
ttccgtgttc ccatctgtac ttggcacaaa caacactatg actcaatagg ctatttgcca 960
agaacataag gtcaatcagg gtacttccgc gttcccaccg ccccatttgg caacaaaata 1020
ggggttattt gggggtcttc cccttgaaat caatgacttg gcaagcatat acatccgtcc 1080
tggcaccaga ataggggtta aatggggact ttccataagc ccaccgcctc atttggcacc 1140
aaaaaggggg atttctatta ttagtcaatg tccttggcca atagccagtg acgtcaatgg 1200
gaacggggcc agttcccctt tcccaccatt accggcaatg gtgggtgggg aaattccata 1260
ttagtcaatg ttcttggcac caaaaccgcg ggactttcc attgacgtca gtggaaaggg 1320
gcgtaacggg gagtgaccat gggcgttccc gggcggagtt atgggcgtta ctgggcggtt 1380
cgtgggcgga ccatgggctg tcctagggta tataagcaga gcccggttag cagaccgcca 1440
ttcgccttca agacagcgtg agggacccac gttctccgga ccagccaccg ggaccgagcg 1500
gcctagccta gccggggacc cttcactgga acgcggatac agcgtgccaa attaaggtat 1560
ggagcgcgga tggtatagct tgcatgctga ttggtggctg gtggcggtat ctatagtata 1620
taatgtatag cctattcatg gtataggcct ccatattggg ggctgtgccg ccattttaat 1680
gcatggatga cgtgtgggct taatgtatag atattgatta ttgattaatc atggcagcca 1740
tagcttttat ctgcatgtta atgatacagc tgccattact atgtgccctt atgccctata 1800
tgttactaat ttccttgttg gcacagtgcc taacagtgct aatgtatgct ttgctataat 1860
gggcggtggg ccaggcctgg catcgggcca actttttgct aattgctggg ggcgcttctc 1920
catgttgttg tggtttatta ttttggcacc cggccattat gcggagcccc tgtcagtcga 1980
aacccgggtt ttggcaccgt gccaaattca cgtcatccat acatagagct ataatgtgat 2040
ttggtgatgg ttaacatatg gtgatgcgtc agtacattca tgacaacacg ccacacacac 2100
tttaggctgc atgccctctc cacacactct tttctggacg cttgccagtt ttggcccagt 2160
gccaatttac cgctacagac acagtaaact gagttagatt gttttattca cagggaactg 2220
ttattgacag ggctggtaca cagtcctctt tgcccatctc aggcacatca atgatggtgt 2280
cctgggggac ccggttcaag gcctctgctt cctccatgat ctcttgcaca gcttcctcca 2340

```
gattcttgtc agtagagcag aaactgcaca tcatgactgt gattataagt ccgaacatac   2400

acagtatagc gcctatggag ctcacggggc gcatccaggc attatgtgca aaagatagta   2460

catgcgaacg gtcagagctt ctcccggtgg tagtaggttg acttgaggta agaatggtgg   2520

tgctcacagt agtagatgag tgatctagaa atggacatta gtcttaatat ctatttttag   2580

atcacatgag ggggggtagg cttcatgaat gttgtctctg tccacttact ggtggtttga   2640

gtgacacttg tggtgacatt atcagcagtg gtggcgttga gcatccaggc gatggcgcat   2700

ccacagatga taagtcccag gggtccagg tccctgaagg taacaggtgt ttgtgtttac   2760

tcacagctgt aaag                                                     2774
```

<210> SEQ ID NO 33
<211> LENGTH: 399
<212> TYPE: DNA
<213> ORGANISM: Artificial Sequence
<220> FEATURE:
<223> OTHER INFORMATION: first variant AoHV-1 short with 3' trunctation

<400> SEQUENCE: 33

```
aaatcaatga cttggcaagc atatacatcc gtcctggcac cagaataggg gttaaatggg     60

gactttccat aagcccaccg cctcatttgg caccaaaaag gggatttct attattagtc     120

aatgtccttg gccaatagcc agtgacgtca atgggaacgg ggccagttcc cctttcccac    180

cattaccggc aatggtgggt ggggaaattc catattagtc aatgttcttg gcaccaaaac    240

cgcggggact ttccattgac gtcagtggaa aggggcgtaa cggggagtga ccatgggcgt    300

tcccgggcgg agttatgggc gttactgggc ggttcgtggg cggaccatgg gctgtcctag    360

ggtatataag cagagcccgg ttagcagacc gccactctc                           399
```

<210> SEQ ID NO 34
<211> LENGTH: 399
<212> TYPE: DNA
<213> ORGANISM: Artificial Sequence
<220> FEATURE:
<223> OTHER INFORMATION: second variant AoHV-1 short promoter with 3' truncation

<400> SEQUENCE: 34

```
aaatcaatga cttggcaagc atatacatcc gtcctggcac cagaataggg gttaaatggg     60

gactttccat aagcccaccg cctcatttgg caccaaaaag gggatttct attattagtc     120

aatgtccttg gccaatagcc agtgacgtca atgggaacgg ggccagttcc cctttcccac    180

cattaccggc aatggtgggt ggggaaattc catattagtc aatgttcttg gcaccaaaac    240

cgcggggact ttccattgac gtcagtggaa aggggcgtaa cggggagtga ccatgggcgt    300

tcccgggcgg agttatgggc gttactgggc ggttcgtggg cggaccatgg gctgtcctag    360

ggtatataag cagagctctg ttcgcacacc tccactctc                           399
```

<210> SEQ ID NO 35
<211> LENGTH: 456
<212> TYPE: DNA
<213> ORGANISM: Artificial Sequence
<220> FEATURE:
<223> OTHER INFORMATION: hCMV promoter (Fig 2A)

<400> SEQUENCE: 35

```
catcaagtgt atcatatgcc aagtacgccc cctattgacg tcaatgacgg taaatggccc     60

gcctggcatt atgcccagta catgacctta tgggactttc ctacttggca gtacatctac    120
```

-continued

```
gtattagtca tcgctattac catggtgatg cggttttggc agtacatcaa tgggcgtgga    180

tagcggtttg actcacgggg atttccaagt ctccacccca ttgacgtcaa tgggagtttg    240

ttttggcacc aaaatcaacg ggactttcca aaatgtcgta acaactccgc cccattgacg    300

caaatgggcg gtaggcgtgt acggtgggag gtctatataa gcagagctcg tttagtgaac    360

cgtcagatcg cctggagacg ccatccacgc tgttttgacc tccatagaag acaccgggac    420

cgatccagcc tccgcggccg ggaacggtgc attgga                              456
```

<210> SEQ ID NO 36
<211> LENGTH: 398
<212> TYPE: DNA
<213> ORGANISM: Artificial Sequence
<220> FEATURE:
<223> OTHER INFORMATION: chCMV short promoter (Fig 2A)

<400> SEQUENCE: 36

```
cgccaattgc atcatcctat tgtttttcta tgggaatttc cctattggca gtacatcaac     60

gtattactaa tggggatttc caatgactaa tacaacgggc agtacgccca gtacgtatga    120

ctaatgggac tttccataat cccgccccat tgacgtcaat gggcatccgt tctggcacca    180

aaatgaatgg gaatttccaa tatgagtcat aaaccccgcc ccattgacgc acattacacg    240

tcaatgggcg gtaggcgtgc cctatgggcg gtctatataa gcagagcccg tttagtgaac    300

cgtcacttcg cttggagcca ccgtccacgc tgtttggagc tccatagaag gaaccgggac    360

ccagccagcc tccgtagccg ggaacggtgc attggaac                            398
```

<210> SEQ ID NO 37
<211> LENGTH: 785
<212> TYPE: DNA
<213> ORGANISM: Artificial Sequence
<220> FEATURE:
<223> OTHER INFORMATION: hCMV promoter (Fig 2B)

<400> SEQUENCE: 37

```
aaatcaatat tggctattgg ccattgcata cgttgtatcc atatcataat atgtacattt     60

atattggctc atgtccaaca ttaccgccat gttgacattg attattgact agttattaat    120

agtaatcaat tacggggtca ttagttcata gcccatatat ggagttccgc gttacataac    180

ttacggtaaa tggcccgcct ggctgaccgc ccaacgaccc ccgcccattg acgtcaataa    240

tgacgtatgt tcccatagta acgccaatag ggactttcca ttgacgtcaa tgggtggagt    300

atttacggta aactgcccac ttggcagtac atcaagtgta tcatatgcca agtacgcccc    360

ctattgacgt caatgacggt aaatggcccg cctggcatta tgcccagtac atgaccttat    420

gggactttcc tacttggcag tacatctacg tattagtcat cgctattacc atggtgatgc    480

ggttttggca gtacatcaat gggcgtggat agcggtttga ctcacgggga tttccaagtc    540

tccaccccat tgacgtcaat gggagtttgt tttggcacca aaatcaacgg gactttccaa    600

aatgtcgtaa caactccgcc ccattgacgc aaatgggcgg taggcgtgta cggtgggagg    660

tctatataag cagagctcgt ttagtgaacc gtcagatcgc ctggagacgc catccacgct    720

gttttgacct ccatagaaga caccgggacc gatccagcct ccgcggccgg gaacggtgca    780

ttgga                                                                 785
```